US012773565B2

(12) United States Patent
Asleson et al.

(10) Patent No.: US 12,773,565 B2
(45) Date of Patent: Oct. 27, 2026

(54) IMPLANTABLE MEDICAL DEVICES FOR MULTI-CHAMBER PACING

(71) Applicant: MEDTRONIC, INC., Minneapolis, MN (US)

(72) Inventors: Andrea J. Asleson, Maple Grove, MN (US); Wade M. Demmer, Coon Rapids, MN (US); Nathan A. Grenz, North Oaks, MN (US); Ruth N. Klepfer, St. Louis Park, MN (US); Alexander R. Mattson, St. Paul, MN (US); Kevin Seifert, Forest Lake, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 290 days.

(21) Appl. No.: 18/200,406

(22) Filed: May 22, 2023

(65) Prior Publication Data

US 2023/0285758 A1 Sep. 14, 2023

Related U.S. Application Data

(62) Division of application No. 17/105,603, filed on Nov. 26, 2020, now abandoned.

(Continued)

(51) Int. Cl.

*A61N 1/36* (2006.01)
*A61B 17/34* (2006.01)

(Continued)

(52) U.S. Cl.

CPC ........ *A61N 1/3684* (2013.01); *A61B 17/3468* (2013.01); *A61N 1/056* (2013.01);

(Continued)

(58) Field of Classification Search

CPC .............. A61N 1/36843; A61N 1/0592; A61N 1/0587; A61N 1/0573; A61N 1/056; A61B 17/3468

See application file for complete search history.

(56) References Cited

U.S. PATENT DOCUMENTS 3,835,864 A 9/1974 Rasor et al.
3,865,118 A 2/1975 Bures (Continued)

FOREIGN PATENT DOCUMENTS

AU 2008279789 B2 10/2011
AU 2008329620 B2 5/2014

(Continued)

OTHER PUBLICATIONS

US 8,886,318 B2, 11/2014, Jacobson et al. (withdrawn)

(Continued)

*Primary Examiner* — Eric D. Bertram
(74) *Attorney, Agent, or Firm* — Mueting Raasch Group

(57) ABSTRACT

Systems, devices, and methods may be used to deliver and provide cardiac pacing therapy to a patient. Leads or leadlets carrying one or more left ventricular electrodes may be positioned in or near the interventricular septum to sense and pace left ventricular signals of the patient's heart. In one example, a leadlet including one or more left ventricular electrodes may extend in the coronary sinus from a leadless implantable medical device located in the right atrium.

7 Claims, 15 Drawing Sheets

Related U.S. Application Data

(60) Provisional application No. 62/940,711, filed on Nov. 26, 2019.

(51) Int. Cl.
*A61N 1/05* (2006.01)
*A61N 1/362* (2006.01)
*A61N 1/368* (2006.01)
*A61N 1/375* (2006.01)

(52) U.S. Cl.
CPC ......... *A61N 1/0573* (2013.01); *A61N 1/3622* (2013.01); *A61N 1/37512* (2017.08); *A61N 2001/0578* (2013.01); *A61N 2001/0585* (2013.01)

(56) References Cited

U.S. PATENT DOCUMENTS 3,943,936 A 3/1976 Rasor et al.
3,949,757 A 4/1976 Sabel
4,142,530 A 3/1979 Wittkampf
4,151,513 A 4/1979 Menken et al.
4,157,720 A 6/1979 Greatbatch
RE30,366 E 8/1980 Rasor et al.
4,243,045 A 1/1981 Mass
4,250,884 A 2/1981 Hartlaub et al.
4,256,115 A 3/1981 Bilitch
4,263,919 A 4/1981 Levin
4,280,502 A 7/1981 Baker, Jr. et al.
4,289,144 A 9/1981 Gilman
4,310,000 A 1/1982 Lindemans
4,312,354 A 1/1982 Walters
4,323,081 A 4/1982 Wiebusch
4,332,259 A 6/1982 McCorkle, Jr.
4,357,946 A 11/1982 Dutcher et al.
4,365,639 A 12/1982 Goldreyer
4,374,382 A 2/1983 Markowitz et al.
4,393,883 A 7/1983 Smyth et al.
4,440,173 A 4/1984 Hudziak et al.
4,476,868 A 10/1984 Thompson
4,479,500 A 10/1984 Smits
4,522,208 A 6/1985 Buffet
4,537,200 A 8/1985 Widrow
4,546,777 A 10/1985 Groch et al.
4,556,063 A 12/1985 Thompson et al.
4,562,841 A 1/1986 Brockway et al.
4,574,814 A 3/1986 Buffet
4,593,702 A 6/1986 Kepski et al.
4,593,955 A 6/1986 Leiber
4,630,611 A 12/1986 King
4,635,639 A 1/1987 Hakala et al.
4,674,508 A 6/1987 DeCote
4,712,554 A 12/1987 Garson
4,729,376 A 3/1988 DeCote
4,754,753 A 7/1988 King
4,759,366 A 7/1988 Callaghan
4,776,338 A 10/1988 Lekholm et al.
4,787,389 A 11/1988 Tarjan
4,793,353 A 12/1988 Borkan
4,819,662 A 4/1989 Heil et al.
4,830,006 A 5/1989 Haluska et al.
4,858,610 A 8/1989 Callaghan et al.
4,865,037 A 9/1989 Chin et al.
4,886,064 A 12/1989 Strandberg
4,887,609 A 12/1989 Cole, Jr.
4,928,688 A 5/1990 Mower
4,953,564 A 9/1990 Berthelsen
4,967,746 A 11/1990 Vandegriff
4,987,897 A 1/1991 Funke
4,989,602 A 2/1991 Sholder et al.
5,012,806 A 5/1991 De Bellis
5,036,849 A 8/1991 Hauck et al.
5,040,534 A 8/1991 Mann et al.
5,058,581 A 10/1991 Silvian
5,078,134 A 1/1992 Heilman et al.
5,109,845 A 5/1992 Yuuchi et al.
5,113,859 A 5/1992 Funke
5,113,869 A 5/1992 Nappholz et al.
5,117,824 A 6/1992 Keimel et al.
5,127,401 A 7/1992 Grievous et al.
5,133,353 A 7/1992 Hauser
5,144,950 A 9/1992 Stoop et al.
5,154,170 A 10/1992 Bennett et al.
5,170,784 A 12/1992 Ramon et al.
5,174,289 A 12/1992 Cohen
5,179,945 A 1/1993 Van Hofwegen et al.
5,193,539 A 3/1993 Schulman et al.
5,193,540 A 3/1993 Schulman et al.
5,241,961 A 9/1993 Henry
5,243,977 A 9/1993 Trabucco et al.
5,255,692 A 10/1993 Neubauer et al.
5,259,387 A 11/1993 dePinto
5,269,326 A 12/1993 Verrier
5,284,136 A 2/1994 Hauck et al.
5,300,107 A 4/1994 Stokes et al.
5,301,677 A 4/1994 Hsung
5,305,760 A 4/1994 Mckown et al.
5,312,439 A 5/1994 Loeb
5,313,953 A 5/1994 Yomtov et al.
5,314,459 A 5/1994 Swanson et al.
5,318,594 A 6/1994 Limousin et al.
5,318,597 A 6/1994 Hauck et al.
5,324,316 A 6/1994 Schulman et al.
5,331,966 A 7/1994 Bennett et al.
5,334,222 A 8/1994 Salo et al.
5,342,408 A 8/1994 Decoriolis et al.
5,370,667 A 12/1994 Alt
5,372,606 A 12/1994 Lang et al.
5,376,106 A 12/1994 Stahmann et al.
5,383,915 A 1/1995 Adams
5,388,578 A 2/1995 Yomtov et al.
5,404,877 A 4/1995 Nolan et al.
5,405,367 A 4/1995 Schulman et al.
5,411,031 A 5/1995 Yomtov
5,411,525 A 5/1995 Swanson et al.
5,411,535 A 5/1995 Fujii et al.
5,456,691 A 10/1995 Snell
5,458,622 A 10/1995 Alt
5,466,246 A 11/1995 Silvian
5,468,254 A 11/1995 Hahn et al.
5,472,453 A 12/1995 Alt
5,522,866 A 6/1996 Fernald
5,540,727 A 7/1996 Tockman et al.
5,545,186 A 8/1996 Olson et al.
5,545,202 A 8/1996 Dahl et al.
5,554,177 A 9/1996 Kieval et al.
5,562,711 A 10/1996 Yerich et al.
5,571,146 A 11/1996 Jones et al.
5,591,214 A 1/1997 Lu
5,620,466 A 4/1997 Haefner et al.
5,634,938 A 6/1997 Swanson et al.
5,649,968 A 7/1997 Alt et al.
5,662,688 A 9/1997 Haefner et al.
5,674,259 A 10/1997 Gray
5,683,426 A 11/1997 Greenhut et al.
5,683,432 A 11/1997 Goedeke et al.
5,706,823 A 1/1998 Wodlinger
5,709,215 A 1/1998 Perttu et al.
5,720,770 A 2/1998 Nappholz et al.
5,728,140 A * 3/1998 Salo ...................... A61N 1/056 607/9
5,728,154 A 3/1998 Crossett et al.
5,741,314 A 4/1998 Daly et al.
5,741,315 A 4/1998 Lee et al.
5,749,909 A 5/1998 Schroeppel et al.
5,752,976 A 5/1998 Duffin et al.
5,752,977 A 5/1998 Grievous et al.
5,755,736 A 5/1998 Gillberg et al.
5,759,199 A 6/1998 Snell et al.
5,774,501 A 6/1998 Halpern et al.
5,792,195 A 8/1998 Carlson et al.
5,792,202 A 8/1998 Rueter
5,792,203 A 8/1998 Schroeppel

(56) References Cited

U.S. PATENT DOCUMENTS 5,792,205 A 8/1998 Alt et al.
5,792,208 A 8/1998 Gray
5,814,089 A 9/1998 Stokes et al.
5,817,130 A 10/1998 Cox et al.
5,827,216 A 10/1998 Igo et al.
5,836,985 A 11/1998 Goyal et al.
5,836,987 A 11/1998 Baumann et al.
5,842,977 A 12/1998 Lesho et al.
5,855,593 A 1/1999 Olson et al.
5,873,894 A 2/1999 Vandegriff et al.
5,891,184 A 4/1999 Lee et al.
5,897,586 A 4/1999 Molina
5,899,876 A 5/1999 Flower
5,899,928 A 5/1999 Sholder et al.
5,919,214 A 7/1999 Ciciarelli et al.
5,928,271 A 7/1999 Hess et al.
5,935,078 A 8/1999 Feierbach
5,941,906 A 8/1999 Barreras et al.
5,944,744 A 8/1999 Paul et al.
5,954,757 A 9/1999 Gray
5,978,713 A 11/1999 Prutchi et al.
5,991,660 A 11/1999 Goyal
5,991,661 A 11/1999 Park et al.
5,999,848 A 12/1999 Gord et al.
5,999,857 A 12/1999 Weijand et al.
6,016,445 A 1/2000 Baura
6,026,320 A 2/2000 Carlson et al.
6,029,085 A 2/2000 Olson et al.
6,041,250 A 3/2000 dePinto
6,044,298 A 3/2000 Salo et al.
6,044,300 A 3/2000 Gray
6,055,454 A 4/2000 Heemels
6,070,104 A 5/2000 Hine et al.
6,073,050 A 6/2000 Griffith
6,076,016 A 6/2000 Feierbach
6,077,236 A 6/2000 Cunningham
6,080,187 A 6/2000 Alt et al.
6,083,248 A 7/2000 Thompson
6,106,551 A 8/2000 Crossett et al.
6,115,636 A 9/2000 Ryan
6,128,526 A 10/2000 Stadler et al.
6,132,456 A 10/2000 Sommer et al.
6,141,581 A 10/2000 Olson et al.
6,141,588 A 10/2000 Cox et al.
6,141,592 A 10/2000 Pauly
6,144,879 A 11/2000 Gray
6,162,195 A 12/2000 Igo et al.
6,164,284 A 12/2000 Schulman et al.
6,167,310 A 12/2000 Grevious
6,201,993 B1 3/2001 Kruse et al.
6,208,894 B1 3/2001 Schulman et al.
6,211,799 B1 4/2001 Post et al.
6,221,011 B1 4/2001 Bardy
6,240,316 B1 5/2001 Richmond et al.
6,240,317 B1 5/2001 Villaseca et al.
6,256,534 B1 7/2001 Dahl
6,259,947 B1 7/2001 Olson et al.
6,266,558 B1 7/2001 Gozani et al.
6,266,567 B1 7/2001 Ishikawa et al.
6,270,457 B1 8/2001 Bardy
6,272,377 B1 8/2001 Sweeney et al.
6,273,856 B1 8/2001 Sun et al.
6,277,072 B1 8/2001 Bardy
6,280,380 B1 8/2001 Bardy
6,285,903 B1 9/2001 Rosenthal et al.
6,285,907 B1 9/2001 Kramer et al.
6,292,698 B1 9/2001 Duffin et al.
6,295,473 B1 9/2001 Rosar
6,297,943 B1 10/2001 Carson
6,298,271 B1 10/2001 Weijand
6,307,751 B1 10/2001 Bodony et al.
6,312,378 B1 11/2001 Bardy
6,315,721 B2 11/2001 Schulman et al.
6,336,903 B1 1/2002 Bardy
6,345,202 B2 2/2002 Richmond et al.
6,351,667 B1 2/2002 Godie
6,351,669 B1 2/2002 Hartley et al.
6,353,759 B1 3/2002 Hartley et al.
6,358,203 B2 3/2002 Bardy
6,361,780 B1 3/2002 Ley et al.
6,368,284 B1 4/2002 Bardy
6,371,922 B1 4/2002 Baumann et al.
6,393,316 B1 5/2002 Gillberg et al.
6,398,728 B1 6/2002 Bardy
6,400,982 B2 6/2002 Sweeney et al.
6,400,990 B1 6/2002 Silvian
6,408,208 B1 6/2002 Sun
6,409,674 B1 6/2002 Brockway et al.
6,411,848 B2 6/2002 Kramer et al.
6,424,865 B1 7/2002 Ding
6,434,429 B1 8/2002 Kraus et al.
6,438,410 B2 8/2002 Hsu et al.
6,438,417 B1 8/2002 Rockwell et al.
6,438,421 B1 8/2002 Stahmann et al.
6,440,066 B1 8/2002 Bardy
6,441,747 B1 8/2002 Khair et al.
6,442,426 B1 8/2002 Kroll
6,442,432 B2 8/2002 Lee
6,443,891 B1 9/2002 Grevious
6,445,953 B1 9/2002 Bulkes et al.
6,453,200 B1 9/2002 Koslar
6,459,929 B1 10/2002 Hopper et al.
6,470,215 B1 10/2002 Kraus et al.
6,471,645 B1 10/2002 Warkentin et al.
6,480,745 B2 11/2002 Nelson et al.
6,487,443 B2 11/2002 Olson et al.
6,490,487 B1 12/2002 Kraus et al.
6,498,951 B1 12/2002 Larson et al.
6,507,755 B1 1/2003 Gozani et al.
6,507,759 B1 1/2003 Prutchi et al.
6,508,771 B1 1/2003 Padmanabhan et al.
6,512,940 B1 1/2003 Brabec et al.
6,522,915 B1 2/2003 Ceballos et al.
6,526,311 B2 2/2003 Begemann
6,539,253 B2 3/2003 Thompson et al.
6,542,775 B2 4/2003 Ding et al.
6,553,258 B2 4/2003 Stahmann et al.
6,561,975 B1 5/2003 Pool et al.
6,564,807 B1 5/2003 Schulman et al.
6,574,506 B2 6/2003 Kramer et al.
6,584,351 B1 6/2003 Ekwall
6,584,352 B2 6/2003 Combs et al.
6,597,948 B1 7/2003 Rockwell et al.
6,597,951 B2 7/2003 Kramer et al.
6,622,046 B2 9/2003 Fraley et al.
6,623,518 B2 9/2003 Thompson et al.
6,628,985 B2 9/2003 Sweeney et al.
6,647,292 B1 11/2003 Bardy et al.
6,666,844 B1 12/2003 Igo et al.
6,689,117 B2 2/2004 Sweeney et al.
6,690,959 B2 2/2004 Thompson
6,694,189 B2 2/2004 Begemann
6,704,602 B2 3/2004 Berg et al.
6,718,212 B2 4/2004 Parry et al.
6,721,597 B1 4/2004 Bardy et al.
6,738,670 B1 5/2004 Almendinger et al.
6,746,797 B2 6/2004 Benson et al.
6,749,566 B2 6/2004 Russ
6,754,528 B2 6/2004 Bardy et al.
6,758,810 B2 7/2004 Lebel et al.
6,763,269 B2 7/2004 Cox
6,778,860 B2 8/2004 Ostroff et al.
6,788,971 B1 9/2004 Sloman et al.
6,788,974 B2 9/2004 Bardy et al.
6,804,558 B2 10/2004 Haller et al.
6,807,442 B1 10/2004 Myklebust et al.
6,847,844 B2 1/2005 Sun et al.
6,869,404 B2 3/2005 Schulhauser et al.
6,871,095 B2 3/2005 Stahmann et al.
6,871,096 B2 3/2005 Hill
6,878,112 B2 4/2005 Linberg et al.
6,885,889 B2 4/2005 Chinchoy
6,892,094 B2 5/2005 Ousdigian et al.
6,897,788 B2 5/2005 Khair et al.

(56) References Cited

U.S. PATENT DOCUMENTS 6,904,315 B2 6/2005 Panken et al.
6,922,592 B2 7/2005 Thompson et al.
6,931,282 B2 8/2005 Esler
6,931,286 B2 8/2005 Sigg et al.
6,934,585 B1 8/2005 Schloss et al.
6,941,169 B2 9/2005 Pappu
6,957,107 B2 10/2005 Rogers et al.
6,978,176 B2 12/2005 Lattouf
6,980,675 B2 12/2005 Evron et al.
6,985,773 B2 1/2006 Von Arx et al.
6,990,375 B2 1/2006 Kloss et al.
6,993,389 B2 1/2006 Ding et al.
7,001,366 B2 2/2006 Ballard
7,003,350 B2 2/2006 Denker et al.
7,006,864 B2 2/2006 Echt et al.
7,013,176 B2 3/2006 Ding et al.
7,013,178 B2 3/2006 Reinke et al.
7,027,871 B2 4/2006 Burnes et al.
7,031,711 B2 4/2006 Brown et al.
7,031,771 B2 4/2006 Brown et al.
7,035,684 B2 4/2006 Lee et al.
7,050,849 B2 5/2006 Echt et al.
7,060,031 B2 6/2006 Webb et al.
7,063,693 B2 6/2006 Guenst
7,082,336 B2 7/2006 Ransbury et al.
7,085,606 B2 8/2006 Flach et al.
7,092,758 B2 8/2006 Sun et al.
7,110,824 B2 9/2006 Amundson et al.
7,120,504 B2 10/2006 Osypka
7,130,681 B2 10/2006 Gebhardt et al.
7,139,613 B2 11/2006 Reinke et al.
7,142,912 B2 11/2006 Wagner et al.
7,146,225 B2 12/2006 Guenst et al.
7,146,226 B2 12/2006 Lau et al.
7,149,581 B2 12/2006 Goedeke
7,149,588 B2 12/2006 Lau et al.
7,158,839 B2 1/2007 Lau
7,162,307 B2 1/2007 Patrias
7,164,952 B2 1/2007 Lau et al.
7,177,700 B1 2/2007 Cox
7,181,284 B2 2/2007 Burnes et al.
7,181,505 B2 2/2007 Haller et al.
7,184,830 B2 2/2007 Echt et al.
7,186,214 B2 3/2007 Ness
7,191,015 B2 * 3/2007 Lamson ................ A61N 1/056
607/129
7,200,437 B1 4/2007 Nabutovsky et al.
7,200,439 B2 4/2007 Zdeblick et al.
7,206,423 B1 4/2007 Feng et al.
7,209,785 B2 4/2007 Kim et al.
7,209,790 B2 4/2007 Thompson et al.
7,211,884 B1 5/2007 Davis et al.
7,212,871 B1 5/2007 Morgan
7,226,440 B2 6/2007 Gelfand et al.
7,228,183 B2 6/2007 Sun et al.
7,231,248 B2 6/2007 Kramer et al.
7,231,253 B2 6/2007 Tidemand et al.
7,236,821 B2 6/2007 Cates et al.
7,236,829 B1 6/2007 Farazi et al.
7,254,448 B2 8/2007 Almendinger et al.
7,260,436 B2 8/2007 Kilgore et al.
7,270,669 B1 9/2007 Sra
7,272,448 B1 9/2007 Morgan et al.
7,277,755 B1 10/2007 Falkenberg et al.
7,280,872 B1 10/2007 Mosesov et al.
7,286,866 B2 10/2007 Okerlund et al.
7,288,096 B2 10/2007 Chin
7,289,847 B1 10/2007 Gill et al.
7,289,852 B2 10/2007 Helfinstine et al.
7,289,853 B1 10/2007 Campbell et al.
7,289,855 B2 10/2007 Nghiem et al.
7,302,294 B2 11/2007 Kamath et al.
7,305,266 B1 12/2007 Kroll
7,307,321 B1 12/2007 Avanzino
7,308,297 B2 12/2007 Reddy et al.
7,308,299 B2 12/2007 Burrell et al.
7,310,556 B2 12/2007 Bulkes
7,317,950 B2 1/2008 Lee
7,319,905 B1 1/2008 Morgan et al.
7,321,677 B2 1/2008 Evron et al.
7,321,798 B2 1/2008 Muhlenberg et al.
7,333,853 B2 2/2008 Mazar et al.
7,336,994 B2 2/2008 Hettrick et al.
7,346,381 B2 3/2008 Okerlund et al.
7,346,393 B2 3/2008 Spinelli et al.
7,347,819 B2 3/2008 Lebel et al.
7,366,572 B2 4/2008 Heruth et al.
7,373,207 B2 5/2008 Lattouf
7,384,403 B2 6/2008 Sherman
7,386,342 B1 6/2008 Falkenberg et al.
7,386,351 B2 6/2008 Hine et al.
7,392,090 B2 6/2008 Sweeney et al.
7,406,105 B2 7/2008 DelMain et al.
7,406,349 B2 7/2008 Seeberger et al.
7,410,497 B2 8/2008 Hastings et al.
7,425,200 B2 9/2008 Brockway et al.
7,433,739 B1 10/2008 Salys et al.
7,454,248 B2 11/2008 Burrell et al.
7,496,409 B2 2/2009 Greenhut et al.
7,496,410 B2 2/2009 Heil
7,499,743 B2 3/2009 Vass et al.
7,502,652 B2 3/2009 Gaunt et al.
7,512,448 B2 3/2009 Malick et al.
7,515,969 B2 4/2009 Tockman et al.
7,526,342 B2 4/2009 Chin et al.
7,529,589 B2 5/2009 Williams et al.
7,532,933 B2 5/2009 Hastings et al.
7,536,222 B2 5/2009 Bardy et al.
7,536,224 B2 5/2009 Ritscher et al.
7,539,541 B2 5/2009 Quiles et al.
7,544,197 B2 6/2009 Kelsch et al.
7,546,166 B2 * 6/2009 Michels ............... A61N 1/0573
607/125
7,558,626 B2 7/2009 Corbucci
7,558,631 B2 7/2009 Cowan et al.
7,565,190 B2 7/2009 Okerlund et al.
7,565,195 B1 7/2009 Kroll et al.
7,584,002 B2 9/2009 Burnes et al.
7,587,074 B2 9/2009 Zarkh et al.
7,590,455 B2 9/2009 Heruth et al.
7,599,730 B2 10/2009 Hunter et al.
7,606,621 B2 10/2009 Brisken et al.
7,610,088 B2 10/2009 Chinchoy
7,610,092 B2 10/2009 Cowan et al.
7,610,099 B2 10/2009 Almendinger et al.
7,610,104 B2 10/2009 Kaplan et al.
7,613,500 B2 11/2009 Vass et al.
7,616,991 B2 11/2009 Mann et al.
7,617,001 B2 11/2009 Penner et al.
7,617,007 B2 11/2009 Williams et al.
7,630,764 B2 12/2009 Ding et al.
7,630,767 B1 12/2009 Poore et al.
7,634,313 B1 12/2009 Kroll et al.
7,635,541 B2 12/2009 Scott et al.
7,637,867 B2 12/2009 Zdeblick
7,640,057 B2 12/2009 Libbus et al.
7,640,060 B2 12/2009 Zdeblick
7,647,109 B2 1/2010 Hastings et al.
7,650,186 B2 1/2010 Hastings et al.
7,657,311 B2 2/2010 Bardy et al.
7,657,313 B2 2/2010 Rom
7,668,596 B2 2/2010 Von Arx et al.
7,682,316 B2 3/2010 Anderson et al.
7,691,047 B2 4/2010 Ferrari
7,702,392 B2 4/2010 Echt et al.
7,706,879 B2 4/2010 Burnes et al.
7,713,194 B2 5/2010 Zdeblick
7,713,195 B2 5/2010 Zdeblick
7,729,783 B2 6/2010 Michels et al.
7,734,333 B2 6/2010 Ghanem et al.
7,734,343 B2 6/2010 Ransbury et al.
7,738,958 B2 6/2010 Zdeblick et al.
7,738,964 B2 6/2010 Von Arx et al.
7,742,629 B2 6/2010 Zarkh et al.

(56) References Cited

U.S. PATENT DOCUMENTS

| | | | |
|---|---|---|---|
| 7,742,812 | B2 | 6/2010 | Ghanem et al. |
| 7,742,816 | B2 | 6/2010 | Masoud et al. |
| 7,742,822 | B2 | 6/2010 | Masoud et al. |
| 7,743,151 | B2 | 6/2010 | Vallapureddy et al. |
| 7,747,047 | B2 | 6/2010 | Okerlund et al. |
| 7,747,335 | B2 | 6/2010 | Williams |
| 7,751,881 | B2 | 7/2010 | Cowan et al. |
| 7,758,521 | B2 | 7/2010 | Morris et al. |
| 7,761,150 | B2 | 7/2010 | Ghanem et al. |
| 7,761,164 | B2 | 7/2010 | Verhoef et al. |
| 7,765,001 | B2 | 7/2010 | Echt et al. |
| 7,769,452 | B2 | 8/2010 | Ghanem et al. |
| 7,778,685 | B2 | 8/2010 | Evron et al. |
| 7,778,686 | B2 | 8/2010 | Vass et al. |
| 7,783,362 | B2 | 8/2010 | Whitehurst et al. |
| 7,792,588 | B2 | 9/2010 | Harding |
| 7,797,059 | B1 | 9/2010 | Bornzin et al. |
| 7,801,596 | B2 | 9/2010 | Fischell et al. |
| 7,809,438 | B2 | 10/2010 | Echt et al. |
| 7,813,785 | B2 | 10/2010 | Okerlund et al. |
| 7,840,281 | B2 | 11/2010 | Kveen et al. |
| 7,844,331 | B2 | 11/2010 | Li et al. |
| 7,844,348 | B2 | 11/2010 | Swoyer et al. |
| 7,846,088 | B2 | 12/2010 | Ness |
| 7,848,815 | B2 | 12/2010 | Brisken et al. |
| 7,848,823 | B2 | 12/2010 | Drasler et al. |
| 7,860,455 | B2 | 12/2010 | Fukumoto et al. |
| 7,871,433 | B2 | 1/2011 | Lattouf |
| 7,877,136 | B1 | 1/2011 | Moffitt et al. |
| 7,877,142 | B2 | 1/2011 | Moaddeb et al. |
| 7,877,144 | B2 | 1/2011 | Coles, Jr. et al. |
| 7,881,786 | B2 | 2/2011 | Jackson |
| 7,881,791 | B2 | 2/2011 | Sambelashvili et al. |
| 7,881,798 | B2 | 2/2011 | Miesel et al. |
| 7,881,806 | B2 | 2/2011 | Horrigan et al. |
| 7,881,810 | B1 | 2/2011 | Chitre et al. |
| 7,890,173 | B2 | 2/2011 | Brisken et al. |
| 7,890,181 | B2 | 2/2011 | Denzene et al. |
| 7,890,192 | B1 | 2/2011 | Kelsch et al. |
| 7,894,885 | B2 | 2/2011 | Bartal et al. |
| 7,894,894 | B2 | 2/2011 | Stadler et al. |
| 7,894,902 | B2 | 2/2011 | Rom |
| 7,894,907 | B2 | 2/2011 | Cowan et al. |
| 7,894,910 | B2 | 2/2011 | Cowan et al. |
| 7,894,915 | B1 | 2/2011 | Chitre et al. |
| 7,899,537 | B1 | 3/2011 | Kroll et al. |
| 7,899,541 | B2 | 3/2011 | Cowan et al. |
| 7,899,542 | B2 | 3/2011 | Cowan et al. |
| 7,899,554 | B2 | 3/2011 | Williams et al. |
| 7,901,360 | B1 | 3/2011 | Yang et al. |
| 7,904,170 | B2 | 3/2011 | Harding |
| 7,907,993 | B2 | 3/2011 | Ghanem et al. |
| 7,912,544 | B1 | 3/2011 | Min et al. |
| 7,920,928 | B1 | 4/2011 | Yang et al. |
| 7,925,343 | B1 | 4/2011 | Min et al. |
| 7,930,022 | B2 | 4/2011 | Zhang et al. |
| 7,930,027 | B2 | 4/2011 | Prakash et al. |
| 7,930,040 | B1 | 4/2011 | Kelsch et al. |
| 7,937,135 | B2 | 5/2011 | Ghanem et al. |
| 7,937,148 | B2 | 5/2011 | Jacobson |
| 7,937,161 | B2 | 5/2011 | Hastings et al. |
| 7,941,214 | B2 | 5/2011 | Kleckner et al. |
| 7,941,218 | B2 | 5/2011 | Sambelashvili et al. |
| 7,945,333 | B2 | 5/2011 | Jacobson |
| 7,946,997 | B2 | 5/2011 | Hubinette |
| 7,949,404 | B2 | 5/2011 | Hill |
| 7,949,405 | B2 | 5/2011 | Feher |
| 7,953,486 | B2 | 5/2011 | Daum et al. |
| 7,953,493 | B2 | 5/2011 | Fowler et al. |
| 7,962,202 | B2 | 6/2011 | Bhunia |
| 7,974,702 | B1 | 7/2011 | Fain et al. |
| 7,979,136 | B2 | 7/2011 | Young et al. |
| 7,983,753 | B2 | 7/2011 | Severin |
| 7,991,467 | B2 | 8/2011 | Markowitz et al. |
| 7,991,471 | B2 | 8/2011 | Ghanem et al. |
| 7,996,063 | B2 | 8/2011 | Vass et al. |
| 7,996,087 | B2 | 8/2011 | Cowan et al. |
| 8,000,791 | B2 | 8/2011 | Sunagawa et al. |
| 8,000,807 | B2 | 8/2011 | Morris et al. |
| 8,001,975 | B2 | 8/2011 | DiSilvestro et al. |
| 8,002,700 | B2 | 8/2011 | Ferek-Petric et al. |
| 8,002,718 | B2 | 8/2011 | Buchholtz et al. |
| 8,010,209 | B2 | 8/2011 | Jacobson |
| 8,019,419 | B1 | 9/2011 | Panescu et al. |
| 8,019,434 | B2 | 9/2011 | Quiles et al. |
| 8,027,727 | B2 | 9/2011 | Freeberg |
| 8,027,729 | B2 | 9/2011 | Sunagawa et al. |
| 8,032,219 | B2 | 10/2011 | Neumann et al. |
| 8,036,743 | B2 | 10/2011 | Savage et al. |
| 8,046,065 | B2 | 10/2011 | Burnes et al. |
| 8,046,079 | B2 | 10/2011 | Bange et al. |
| 8,046,080 | B2 | 10/2011 | Von Arx et al. |
| 8,050,297 | B2 | 11/2011 | Delmain et al. |
| 8,050,759 | B2 | 11/2011 | Stegemann et al. |
| 8,050,774 | B2 | 11/2011 | Kveen et al. |
| 8,055,345 | B2 | 11/2011 | Li et al. |
| 8,055,350 | B2 | 11/2011 | Roberts |
| 8,060,185 | B2 | 11/2011 | Hunter et al. |
| 8,060,212 | B1 | 11/2011 | Rios et al. |
| 8,065,018 | B2 | 11/2011 | Haubrich et al. |
| 8,068,920 | B2 | 11/2011 | Gaudiani |
| 8,073,542 | B2 | 12/2011 | Doerr |
| 8,078,278 | B2 | 12/2011 | Penner |
| 8,078,283 | B2 | 12/2011 | Cowan et al. |
| 8,095,123 | B2 | 1/2012 | Gray |
| 8,102,789 | B2 | 1/2012 | Rosar et al. |
| 8,103,359 | B2 | 1/2012 | Reddy |
| 8,103,361 | B2 | 1/2012 | Moser |
| 8,105,714 | B2 | 1/2012 | Schmidt et al. |
| 8,112,148 | B2 | 2/2012 | Giftakis et al. |
| 8,114,021 | B2 | 2/2012 | Robertson et al. |
| 8,121,680 | B2 | 2/2012 | Falkenberg et al. |
| 8,123,684 | B2 | 2/2012 | Zdeblick |
| 8,126,545 | B2 | 2/2012 | Flach et al. |
| 8,131,334 | B2 | 3/2012 | Lu et al. |
| 8,140,161 | B2 | 3/2012 | Willerton et al. |
| 8,145,308 | B2 | 3/2012 | Sambelashvili et al. |
| 8,150,521 | B2 | 4/2012 | Crowley et al. |
| 8,160,672 | B2 | 4/2012 | Kim et al. |
| 8,160,702 | B2 | 4/2012 | Mann et al. |
| 8,160,704 | B2 | 4/2012 | Freeberg |
| 8,165,694 | B2 | 4/2012 | Carbanaru et al. |
| 8,175,715 | B1 | 5/2012 | Cox |
| 8,180,428 | B2 | 5/2012 | Kaiser et al. |
| 8,180,451 | B2 | 5/2012 | Hickman et al. |
| 8,185,213 | B2 | 5/2012 | Kveen et al. |
| 8,187,161 | B2 | 5/2012 | Li et al. |
| 8,195,293 | B2 | 6/2012 | Limousin et al. |
| 8,204,590 | B2 | 6/2012 | Sambelashvili et al. |
| 8,204,595 | B2 | 6/2012 | Pianca et al. |
| 8,204,605 | B2 | 6/2012 | Hastings et al. |
| 8,209,014 | B2 | 6/2012 | Doerr |
| 8,214,041 | B2 | 7/2012 | Van Gelder et al. |
| 8,214,043 | B2 | 7/2012 | Matos |
| 8,224,244 | B2 | 7/2012 | Kim et al. |
| 8,229,556 | B2 | 7/2012 | Li |
| 8,233,985 | B2 | 7/2012 | Bulkes et al. |
| 8,262,578 | B1 | 9/2012 | Bharmi et al. |
| 8,265,748 | B2 | 9/2012 | Liu et al. |
| 8,265,757 | B2 | 9/2012 | Mass et al. |
| 8,280,521 | B2 | 10/2012 | Haubrich et al. |
| 8,285,387 | B2 | 10/2012 | Utsi et al. |
| 8,290,598 | B2 | 10/2012 | Boon et al. |
| 8,290,600 | B2 | 10/2012 | Hastings et al. |
| 8,295,939 | B2 | 10/2012 | Jacobson |
| 8,295,947 | B2 * | 10/2012 | Lamson ............... A61N 1/0573 607/129 |
| 8,301,254 | B2 | 10/2012 | Mosesov et al. |
| 8,315,701 | B2 | 11/2012 | Cowan et al. |
| 8,315,708 | B2 | 11/2012 | Berthelsdorf et al. |
| 8,321,014 | B2 | 11/2012 | Maskara et al. |
| 8,321,021 | B2 | 11/2012 | Kisker et al. |
| 8,321,036 | B2 | 11/2012 | Brockway et al. |
| 8,332,036 | B2 | 12/2012 | Hastings et al. |

(56) References Cited

U.S. PATENT DOCUMENTS

| | | | |
|---|---|---|---|
| 8,335,563 | B2 | 12/2012 | Stessman |
| 8,335,568 | B2 | 12/2012 | Heruth et al. |
| 8,340,750 | B2 | 12/2012 | Prakash et al. |
| 8,340,780 | B2 | 12/2012 | Hastings et al. |
| 8,352,025 | B2 | 1/2013 | Jacobson |
| 8,352,027 | B2 | 1/2013 | Spinelli et al. |
| 8,352,028 | B2 | 1/2013 | Wenger |
| 8,352,038 | B2 | 1/2013 | Mao et al. |
| 8,359,098 | B2 | 1/2013 | Lund et al. |
| 8,364,261 | B2 | 1/2013 | Stubbs et al. |
| 8,364,276 | B2 | 1/2013 | Willis |
| 8,369,959 | B2 | 2/2013 | Meskens |
| 8,369,962 | B2 | 2/2013 | Abrahamson |
| 8,380,320 | B2 | 2/2013 | Spital |
| 8,383,269 | B2 | 2/2013 | Scott et al. |
| 8,386,051 | B2 | 2/2013 | Rys |
| 8,391,964 | B2 | 3/2013 | Musley et al. |
| 8,391,981 | B2 | 3/2013 | Mosesov |
| 8,391,990 | B2 | 3/2013 | Smith et al. |
| 8,401,616 | B2 | 3/2013 | Verard et al. |
| 8,406,874 | B2 | 3/2013 | Liu et al. |
| 8,406,879 | B2 | 3/2013 | Shuros et al. |
| 8,406,886 | B2 | 3/2013 | Gaunt et al. |
| 8,406,899 | B2 | 3/2013 | Reddy et al. |
| 8,412,352 | B2 | 4/2013 | Griswold et al. |
| 8,417,340 | B2 | 4/2013 | Goossen |
| 8,417,341 | B2 | 4/2013 | Freeberg |
| 8,423,149 | B2 | 4/2013 | Hennig |
| 8,428,716 | B2 | 4/2013 | Mullen et al. |
| 8,428,722 | B2 | 4/2013 | Verhoef et al. |
| 8,433,402 | B2 | 4/2013 | Ruben et al. |
| 8,433,409 | B2 | 4/2013 | Johnson et al. |
| 8,433,420 | B2 | 4/2013 | Bange et al. |
| 8,447,412 | B2 | 5/2013 | Dal Molin et al. |
| 8,452,413 | B2 | 5/2013 | Young et al. |
| 8,457,740 | B2 | 6/2013 | Osche |
| 8,457,742 | B2 | 6/2013 | Jacobson |
| 8,457,744 | B2 | 6/2013 | Janzig et al. |
| 8,457,761 | B2 | 6/2013 | Wariar |
| 8,467,871 | B2 | 6/2013 | Maskara |
| 8,478,407 | B2 | 7/2013 | Demmer et al. |
| 8,478,408 | B2 | 7/2013 | Hastings et al. |
| 8,478,431 | B2 | 7/2013 | Griswold et al. |
| 8,494,632 | B2 | 7/2013 | Sun et al. |
| 8,504,156 | B2 | 8/2013 | Bonner et al. |
| 8,509,910 | B2 | 8/2013 | Sowder et al. |
| 8,509,916 | B2 | 8/2013 | Byrd et al. |
| 8,515,559 | B2 | 8/2013 | Roberts et al. |
| 8,521,268 | B2 | 8/2013 | Zhang et al. |
| 8,525,340 | B2 | 9/2013 | Eckhardt et al. |
| 8,527,068 | B2 | 9/2013 | Ostroff |
| 8,532,790 | B2 | 9/2013 | Griswold |
| 8,538,526 | B2 | 9/2013 | Stahmann et al. |
| 8,541,131 | B2 | 9/2013 | Lund |
| 8,543,205 | B2 | 9/2013 | Ostroff |
| 8,547,248 | B2 | 10/2013 | Zdeblick et al. |
| 8,548,605 | B2 | 10/2013 | Ollivier |
| 8,554,333 | B2 | 10/2013 | Wu et al. |
| 8,565,882 | B2 | 10/2013 | Matoes |
| 8,565,897 | B2 | 10/2013 | Regnier et al. |
| 8,571,678 | B2 | 10/2013 | Wang |
| 8,577,327 | B2 | 11/2013 | Makdissi et al. |
| 8,588,926 | B2 | 11/2013 | Moore et al. |
| 8,594,775 | B2 | 11/2013 | Ghosh et al. |
| 8,612,002 | B2 | 12/2013 | Faltys et al. |
| 8,615,310 | B2 | 12/2013 | Khairkhahan et al. |
| 8,617,082 | B2 | 12/2013 | Zhang et al. |
| 8,626,280 | B2 | 1/2014 | Allavatam et al. |
| 8,626,294 | B2 | 1/2014 | Sheldon et al. |
| 8,634,908 | B2 | 1/2014 | Cowan |
| 8,634,912 | B2 | 1/2014 | Bornzin et al. |
| 8,634,919 | B1 | 1/2014 | Hou et al. |
| 8,639,333 | B2 | 1/2014 | Stadler et al. |
| 8,639,335 | B2 | 1/2014 | Peichel et al. |
| 8,644,934 | B2 | 2/2014 | Hastings et al. |
| 8,649,859 | B2 | 2/2014 | Smith et al. |
| 8,670,842 | B1 | 3/2014 | Bornzin et al. |
| 8,676,314 | B2 | 3/2014 | Maskara et al. |
| 8,676,319 | B2 | 3/2014 | Knoll |
| 8,676,335 | B2 | 3/2014 | Katoozi et al. |
| 8,700,173 | B2 | 4/2014 | Edlund |
| 8,700,181 | B2 | 4/2014 | Bornzin et al. |
| 8,705,599 | B2 | 4/2014 | Dal Molin et al. |
| 8,718,766 | B2 | 5/2014 | Wahlberg |
| 8,718,773 | B2 | 5/2014 | Willis et al. |
| 8,725,260 | B2 | 5/2014 | Shuros et al. |
| 8,731,642 | B2 | 5/2014 | Zarkh et al. |
| 8,738,133 | B2 | 5/2014 | Shuros et al. |
| 8,738,147 | B2 | 5/2014 | Hastings et al. |
| 8,744,555 | B2 | 6/2014 | Allavatam et al. |
| 8,744,572 | B1 | 6/2014 | Greenhut et al. |
| 8,747,314 | B2 | 6/2014 | Stahmann et al. |
| 8,750,994 | B2 | 6/2014 | Ghosh et al. |
| 8,750,998 | B1 | 6/2014 | Ghosh et al. |
| 8,755,884 | B2 | 6/2014 | Demmer et al. |
| 8,758,365 | B2 | 6/2014 | Bonner et al. |
| 8,768,459 | B2 | 7/2014 | Ghosh et al. |
| 8,768,483 | B2 | 7/2014 | Schmitt et al. |
| 8,774,572 | B2 | 7/2014 | Hamamoto |
| 8,781,605 | B2 | 7/2014 | Bornzin et al. |
| 8,788,035 | B2 | 7/2014 | Jacobson |
| 8,788,053 | B2 | 7/2014 | Jacobson |
| 8,798,740 | B2 | 8/2014 | Samade et al. |
| 8,798,745 | B2 | 8/2014 | Jacobson |
| 8,798,762 | B2 | 8/2014 | Fain et al. |
| 8,798,770 | B2 | 8/2014 | Reddy |
| 8,805,505 | B1 | 8/2014 | Roberts |
| 8,805,528 | B2 | 8/2014 | Corndorf |
| 8,812,109 | B2 | 8/2014 | Blomqvist et al. |
| 8,818,504 | B2 | 8/2014 | Bodner et al. |
| 8,827,913 | B2 | 9/2014 | Havel et al. |
| 8,831,747 | B1 | 9/2014 | Min et al. |
| 8,855,789 | B2 | 10/2014 | Jacobson |
| 8,861,830 | B2 | 10/2014 | Brada et al. |
| 8,868,186 | B2 | 10/2014 | Kroll |
| 8,886,307 | B2 | 11/2014 | Sambelashvili et al. |
| 8,886,311 | B2 | 11/2014 | Anderson et al. |
| 8,886,339 | B2 | 11/2014 | Faltys et al. |
| 8,903,473 | B2 | 12/2014 | Rogers et al. |
| 8,903,513 | B2 | 12/2014 | Ollivier |
| 8,909,336 | B2 | 12/2014 | Navarro-Paredes et al. |
| 8,914,131 | B2 | 12/2014 | Bornzin et al. |
| 8,923,795 | B2 | 12/2014 | Makdissi et al. |
| 8,923,963 | B2 | 12/2014 | Bonner et al. |
| 8,938,300 | B2 | 1/2015 | Rosero |
| 8,942,806 | B2 | 1/2015 | Sheldon et al. |
| 8,948,883 | B2 | 2/2015 | Eggen et al. |
| 8,958,892 | B2 | 2/2015 | Khairkhahan et al. |
| 8,977,358 | B2 | 3/2015 | Ewert et al. |
| 8,989,873 | B2 | 3/2015 | Locsin |
| 8,996,109 | B2 | 3/2015 | Karst et al. |
| 9,002,467 | B2 | 4/2015 | Smith et al. |
| 9,008,776 | B2 | 4/2015 | Cowan et al. |
| 9,008,777 | B2 | 4/2015 | Dianaty et al. |
| 9,014,818 | B2 | 4/2015 | Deterre et al. |
| 9,017,341 | B2 | 4/2015 | Bornzin et al. |
| 9,020,611 | B2 | 4/2015 | Khairkhahan et al. |
| 9,033,996 | B1 | 5/2015 | West |
| 9,037,262 | B2 | 5/2015 | Regnier et al. |
| 9,042,984 | B2 | 5/2015 | Demmer et al. |
| 9,072,872 | B2 | 7/2015 | Asleson et al. |
| 9,072,911 | B2 | 7/2015 | Hastings et al. |
| 9,072,913 | B2 | 7/2015 | Jacobson |
| 9,101,281 | B2 | 8/2015 | Reinert et al. |
| 9,119,959 | B2 | 9/2015 | Rys et al. |
| 9,155,882 | B2 | 10/2015 | Grubac et al. |
| 9,168,372 | B2 | 10/2015 | Fain |
| 9,168,380 | B1 | 10/2015 | Greenhut et al. |
| 9,168,383 | B2 | 10/2015 | Jacobson et al. |
| 9,180,285 | B2 | 11/2015 | Moore et al. |
| 9,192,774 | B2 | 11/2015 | Jacobson |
| 9,205,225 | B2 | 12/2015 | Khairkhahan et al. |
| 9,216,285 | B1 | 12/2015 | Boling et al. |
| 9,216,293 | B2 | 12/2015 | Berthiaume et al. |

(56) References Cited

U.S. PATENT DOCUMENTS

| | | | |
|---|---|---|---|
| 9,216,298 | B2 | 12/2015 | Jacobson |
| 9,227,077 | B2 | 1/2016 | Jacobson |
| 9,238,145 | B2 | 1/2016 | Wenzel et al. |
| 9,242,102 | B2 | 1/2016 | Khairkhahan et al. |
| 9,242,113 | B2 | 1/2016 | Smith et al. |
| 9,248,300 | B2 | 2/2016 | Rys et al. |
| 9,265,436 | B2 | 2/2016 | Min et al. |
| 9,265,962 | B2 | 2/2016 | Dianaty et al. |
| 9,272,155 | B2 | 3/2016 | Ostroff |
| 9,278,218 | B2 | 3/2016 | Karst et al. |
| 9,278,229 | B1 | 3/2016 | Reinke et al. |
| 9,283,381 | B2 | 3/2016 | Grubac et al. |
| 9,283,382 | B2 | 3/2016 | Berthiaume et al. |
| 9,289,612 | B1 | 3/2016 | Sambelashbili et al. |
| 9,302,115 | B2 | 4/2016 | Molin et al. |
| 9,320,446 | B2 | 4/2016 | Gillberg et al. |
| 9,333,364 | B2 | 5/2016 | Echt et al. |
| 9,358,387 | B2 | 6/2016 | Suwito et al. |
| 9,358,400 | B2 | 6/2016 | Jacobson |
| 9,364,675 | B2 | 6/2016 | Deterre et al. |
| 9,370,663 | B2 | 6/2016 | Moulder |
| 9,375,580 | B2 | 6/2016 | Bonner et al. |
| 9,375,581 | B2 | 6/2016 | Baru et al. |
| 9,381,365 | B2 | 7/2016 | Kibler et al. |
| 9,393,424 | B2 | 7/2016 | Demmer et al. |
| 9,393,436 | B2 | 7/2016 | Doerr |
| 9,399,139 | B2 | 7/2016 | Demmer et al. |
| 9,399,140 | B2 | 7/2016 | Cho et al. |
| 9,409,033 | B2 | 8/2016 | Jacobson |
| 9,427,594 | B1 | 8/2016 | Bornzin et al. |
| 9,433,368 | B2 | 9/2016 | Stahmann et al. |
| 9,433,780 | B2 | 9/2016 | Regnier et al. |
| 9,457,193 | B2 | 10/2016 | Klimovitch et al. |
| 9,474,457 | B2 | 10/2016 | Ghosh et al. |
| 9,486,151 | B2 | 11/2016 | Ghosh et al. |
| 9,492,668 | B2 | 11/2016 | Sheldon et al. |
| 9,492,669 | B2 | 11/2016 | Demmer et al. |
| 9,492,674 | B2 | 11/2016 | Schmidt et al. |
| 9,492,677 | B2 | 11/2016 | Greenhut et al. |
| 9,511,233 | B2 | 12/2016 | Sambelashvili |
| 9,511,236 | B2 | 12/2016 | Varady et al. |
| 9,511,237 | B2 | 12/2016 | Deterre et al. |
| 9,517,336 | B2 | 12/2016 | Eggen et al. |
| 9,522,276 | B2 | 12/2016 | Shen et al. |
| 9,522,280 | B2 | 12/2016 | Fishler et al. |
| 9,526,522 | B2 | 12/2016 | Wood et al. |
| 9,526,891 | B2 | 12/2016 | Eggen et al. |
| 9,526,909 | B2 | 12/2016 | Stahmann et al. |
| 9,533,163 | B2 | 1/2017 | Klimovitch et al. |
| 9,561,382 | B2 | 2/2017 | Persson et al. |
| 9,566,012 | B2 | 2/2017 | Greenhut et al. |
| 9,579,500 | B2 | 2/2017 | Rys et al. |
| 9,623,234 | B2 | 4/2017 | Anderson |
| 9,636,511 | B2 | 5/2017 | Carney et al. |
| 9,643,014 | B2 | 5/2017 | Zhang et al. |
| 9,675,579 | B2 | 6/2017 | Rock et al. |
| 9,707,399 | B2 | 7/2017 | Zielinski et al. |
| 9,724,519 | B2 | 8/2017 | Demmer et al. |
| 9,789,319 | B2 | 10/2017 | Sambelashvili |
| 9,808,628 | B2 | 11/2017 | Sheldon et al. |
| 9,808,633 | B2 | 11/2017 | Bonner et al. |
| 9,877,789 | B2 | 1/2018 | Ghosh |
| 9,901,732 | B2 | 2/2018 | Sommer et al. |
| 9,924,884 | B2 | 3/2018 | Ghosh et al. |
| 10,004,467 | B2 | 6/2018 | Lahm et al. |
| 10,064,567 | B2 | 9/2018 | Ghosh et al. |
| 10,092,744 | B2 | 10/2018 | Sommer et al. |
| 10,099,050 | B2 | 10/2018 | Chen et al. |
| 10,166,396 | B2 | 1/2019 | Schrock et al. |
| 10,251,555 | B2 | 4/2019 | Ghosh et al. |
| 10,315,028 | B2 | 6/2019 | Sommer et al. |
| 10,406,370 | B1 | 9/2019 | Makharinsky |
| 10,456,581 | B2 | 10/2019 | Liu et al. |
| 10,463,853 | B2 * | 11/2019 | Drake .................... A61N 1/057 |
| 10,478,627 | B2 | 11/2019 | Muessig |
| 2002/0032470 | A1 | 3/2002 | Linberg |
| 2002/0035376 | A1 | 3/2002 | Bardy et al. |
| 2002/0035377 | A1 | 3/2002 | Bardy et al. |
| 2002/0035378 | A1 | 3/2002 | Bardy et al. |
| 2002/0035380 | A1 | 3/2002 | Rissmann et al. |
| 2002/0035381 | A1 | 3/2002 | Bardy et al. |
| 2002/0042629 | A1 | 4/2002 | Bardy et al. |
| 2002/0042630 | A1 | 4/2002 | Bardy et al. |
| 2002/0042634 | A1 | 4/2002 | Bardy et al. |
| 2002/0049475 | A1 | 4/2002 | Bardy et al. |
| 2002/0049476 | A1 | 4/2002 | Bardy et al. |
| 2002/0052636 | A1 | 5/2002 | Bardy et al. |
| 2002/0068958 | A1 | 6/2002 | Bardy et al. |
| 2002/0072773 | A1 | 6/2002 | Bardy et al. |
| 2002/0082665 | A1 | 6/2002 | Haller et al. |
| 2002/0091414 | A1 | 7/2002 | Bardy et al. |
| 2002/0095196 | A1 | 7/2002 | Linberg |
| 2002/0099423 | A1 | 7/2002 | Berg et al. |
| 2002/0103510 | A1 | 8/2002 | Bardy et al. |
| 2002/0107545 | A1 | 8/2002 | Rissmann et al. |
| 2002/0107546 | A1 | 8/2002 | Ostroff et al. |
| 2002/0107547 | A1 | 8/2002 | Erlinger et al. |
| 2002/0107548 | A1 | 8/2002 | Bardy et al. |
| 2002/0107549 | A1 | 8/2002 | Bardy et al. |
| 2002/0107559 | A1 | 8/2002 | Sanders et al. |
| 2002/0120299 | A1 | 8/2002 | Ostroff et al. |
| 2002/0173830 | A1 | 11/2002 | Starkweather et al. |
| 2002/0193846 | A1 | 12/2002 | Pool et al. |
| 2003/0004549 | A1 | 1/2003 | Hill et al. |
| 2003/0009203 | A1 | 1/2003 | Lebel et al. |
| 2003/0028082 | A1 | 2/2003 | Thompson |
| 2003/0040779 | A1 | 2/2003 | Engmark et al. |
| 2003/0041866 | A1 | 3/2003 | Linberg et al. |
| 2003/0045805 | A1 | 3/2003 | Sheldon et al. |
| 2003/0083104 | A1 | 5/2003 | Bonner et al. |
| 2003/0088278 | A1 | 5/2003 | Bardy et al. |
| 2003/0097153 | A1 | 5/2003 | Bardy et al. |
| 2003/0105497 | A1 | 6/2003 | Zhu et al. |
| 2003/0114908 | A1 | 6/2003 | Flach |
| 2003/0144701 | A1 | 7/2003 | Mehra et al. |
| 2003/0187460 | A1 | 10/2003 | Chin et al. |
| 2003/0187461 | A1 | 10/2003 | Chin |
| 2004/0015193 | A1 * | 1/2004 | Lamson ............... A61N 1/0573 607/9 |
| 2004/0024435 | A1 | 2/2004 | Leckrone et al. |
| 2004/0068302 | A1 | 4/2004 | Rodgers et al. |
| 2004/0087938 | A1 | 5/2004 | Leckrone et al. |
| 2004/0088035 | A1 | 5/2004 | Guenst et al. |
| 2004/0102830 | A1 | 5/2004 | Williams |
| 2004/0127959 | A1 | 7/2004 | Amundson et al. |
| 2004/0133242 | A1 | 7/2004 | Chapman et al. |
| 2004/0147969 | A1 | 7/2004 | Mann et al. |
| 2004/0147973 | A1 | 7/2004 | Hauser |
| 2004/0167558 | A1 | 8/2004 | Igo et al. |
| 2004/0167587 | A1 | 8/2004 | Thompson |
| 2004/0172071 | A1 | 9/2004 | Bardy et al. |
| 2004/0172077 | A1 | 9/2004 | Chinchoy |
| 2004/0172104 | A1 | 9/2004 | Berg et al. |
| 2004/0176817 | A1 | 9/2004 | Wahlstrand et al. |
| 2004/0176818 | A1 | 9/2004 | Wahlstrand et al. |
| 2004/0176830 | A1 | 9/2004 | Fang |
| 2004/0186529 | A1 | 9/2004 | Bardy et al. |
| 2004/0204673 | A1 | 10/2004 | Flaherty |
| 2004/0210292 | A1 | 10/2004 | Bardy et al. |
| 2004/0210293 | A1 | 10/2004 | Bardy et al. |
| 2004/0210294 | A1 | 10/2004 | Bardy et al. |
| 2004/0215308 | A1 | 10/2004 | Bardy et al. |
| 2004/0220624 | A1 | 11/2004 | Ritscher et al. |
| 2004/0220626 | A1 | 11/2004 | Wagner |
| 2004/0220639 | A1 | 11/2004 | Mulligan et al. |
| 2004/0230236 | A1 | 11/2004 | Struble |
| 2004/0230283 | A1 | 11/2004 | Prinzen et al. |
| 2004/0249431 | A1 | 12/2004 | Ransbury et al. |
| 2004/0260348 | A1 | 12/2004 | Bakken et al. |
| 2004/0267303 | A1 | 12/2004 | Guenst |
| 2005/0008210 | A1 | 1/2005 | Evron et al. |
| 2005/0038477 | A1 | 2/2005 | Kramer et al. |
| 2005/0061320 | A1 | 3/2005 | Lee et al. |
| 2005/0070962 | A1 | 3/2005 | Echt et al. |

(56) References Cited

U.S. PATENT DOCUMENTS

2005/0102003 A1 5/2005 Grabek et al.
2005/0137629 A1 6/2005 Dyjach et al.
2005/0149138 A1 7/2005 Min et al.
2005/0165466 A1 7/2005 Morris et al.
2005/0182465 A1 8/2005 Ness
2005/0203410 A1 9/2005 Jenkins
2005/0277990 A1 12/2005 Ostroff et al.
2005/0283208 A1 12/2005 Von Arx et al.
2005/0288743 A1 12/2005 Ahn et al.
2006/0042830 A1 3/2006 Maghribi et al.
2006/0052829 A1 3/2006 Sun et al.
2006/0052830 A1 3/2006 Spinelli et al.
2006/0064135 A1 3/2006 Brockway
2006/0064149 A1 3/2006 Belacazar et al.
2006/0074285 A1 4/2006 Zarkh et al.
2006/0085039 A1 4/2006 Hastings et al.
2006/0085041 A1 4/2006 Hastings et al.
2006/0085042 A1 4/2006 Hastings et al.
2006/0095078 A1 5/2006 Tronnes
2006/0106442 A1 5/2006 Richardson et al.
2006/0116746 A1 6/2006 Chin
2006/0135999 A1 6/2006 Bodner et al.
2006/0136004 A1 6/2006 Cowan et al.
2006/0161061 A1 7/2006 Echt et al.
2006/0161205 A1 7/2006 Mitrani et al.
2006/0200002 A1 9/2006 Guenst
2006/0206151 A1 9/2006 Lu
2006/0212079 A1 9/2006 Routh et al.
2006/0235478 A1 10/2006 Van Gelder et al.
2006/0241701 A1 10/2006 Markowitz et al.
2006/0241705 A1 10/2006 Neumann et al.
2006/0247672 A1 11/2006 Vidlund et al.
2006/0259088 A1 11/2006 Pastore et al.
2006/0265018 A1 11/2006 Smith et al.
2007/0004979 A1 1/2007 Wojciechowicz et al.
2007/0016098 A1 1/2007 Kim et al.
2007/0027508 A1 2/2007 Cowan
2007/0049975 A1 3/2007 Cates et al.
2007/0078490 A1 4/2007 Cowan et al.
2007/0088394 A1 4/2007 Jacobson
2007/0088396 A1 4/2007 Jacobson
2007/0088397 A1 4/2007 Jacobson
2007/0088398 A1 4/2007 Jacobson
2007/0088405 A1 4/2007 Jaconson
2007/0135882 A1 6/2007 Drasler et al.
2007/0135883 A1 6/2007 Drasler et al.
2007/0150037 A1 6/2007 Hastings et al.
2007/0150038 A1 6/2007 Hastings et al.
2007/0156190 A1 7/2007 Cinbis
2007/0219525 A1 9/2007 Gelfand et al.
2007/0219590 A1 9/2007 Hastings et al.
2007/0225545 A1 9/2007 Ferrari
2007/0233206 A1 10/2007 Frikart et al.
2007/0239244 A1 10/2007 Morgan et al.
2007/0255376 A1 11/2007 Michels et al.
2007/0276444 A1 11/2007 Gelbart et al.
2007/0293900 A1 12/2007 Sheldon et al.
2007/0293904 A1 12/2007 Gelbart et al.
2007/0299475 A1 12/2007 Levin et al.
2008/0004663 A1 1/2008 Jorgenson
2008/0021505 A1 1/2008 Hastings et al.
2008/0021519 A1 1/2008 De Geest et al.
2008/0021532 A1 1/2008 Kveen et al.
2008/0065183 A1 3/2008 Whitehurst et al.
2008/0065185 A1 3/2008 Worley
2008/0071318 A1 3/2008 Brooke et al.
2008/0103539 A1 5/2008 Stegemann et al.
2008/0109054 A1* 5/2008 Hastings ............ A61N 1/37229 607/127
2008/0119911 A1 5/2008 Rosero
2008/0130670 A1 6/2008 Kim et al.
2008/0154139 A1 6/2008 Shuros et al.
2008/0154322 A1 6/2008 Jackson et al.
2008/0228234 A1 9/2008 Stancer
2008/0234771 A1 9/2008 Chinchoy et al.
2008/0243217 A1 10/2008 Wildon
2008/0269814 A1 10/2008 Rosero
2008/0269816 A1 10/2008 Prakash et al.
2008/0269823 A1 10/2008 Burnes et al.
2008/0269825 A1 10/2008 Chinchoy et al.
2008/0275518 A1 11/2008 Ghanem et al.
2008/0275519 A1 11/2008 Ghanem et al.
2008/0288008 A1 11/2008 Lee
2008/0288039 A1 11/2008 Reddy
2008/0294208 A1 11/2008 Willis et al.
2008/0294210 A1 11/2008 Rosero
2008/0294229 A1 11/2008 Friedman et al.
2008/0306359 A1 12/2008 Zdeblick et al.
2009/0018599 A1 1/2009 Hastings et al.
2009/0024180 A1 1/2009 Kisker et al.
2009/0036941 A1 2/2009 Corbucci
2009/0048646 A1 2/2009 Katoozi et al.
2009/0062895 A1 3/2009 Stahmann et al.
2009/0082827 A1 3/2009 Kveen et al.
2009/0082828 A1 3/2009 Ostroff
2009/0088813 A1 4/2009 Brockway et al.
2009/0099619 A1 4/2009 Lessmeier et al.
2009/0131907 A1 5/2009 Chin et al.
2009/0135886 A1 5/2009 Robertson et al.
2009/0143835 A1 6/2009 Pastore et al.
2009/0171408 A1 7/2009 Solem
2009/0171414 A1 7/2009 Kelly et al.
2009/0204163 A1 8/2009 Shuros et al.
2009/0204170 A1 8/2009 Hastings et al.
2009/0210024 A1 8/2009 Jason
2009/0216292 A1 8/2009 Pless et al.
2009/0234407 A1 9/2009 Hastings et al.
2009/0234411 A1 9/2009 Sambelashvili et al.
2009/0234412 A1 9/2009 Sambelashvili
2009/0234413 A1 9/2009 Sambelashvili et al.
2009/0234414 A1 9/2009 Sambelashvili et al.
2009/0234415 A1 9/2009 Sambelashvili et al.
2009/0248103 A1 10/2009 Sambelashvili et al.
2009/0266573 A1 10/2009 Engmark et al.
2009/0275998 A1 11/2009 Burnes et al.
2009/0275999 A1 11/2009 Burnes et al.
2009/0299447 A1 12/2009 Jensen et al.
2010/0013668 A1 1/2010 Kantervik
2010/0016911 A1 1/2010 Willis et al.
2010/0016914 A1 1/2010 Mullen et al.
2010/0023078 A1 1/2010 Dong et al.
2010/0023085 A1 1/2010 Wu et al.
2010/0030061 A1 2/2010 Canfield et al.
2010/0030327 A1 2/2010 Chatel
2010/0042108 A1 2/2010 Hibino
2010/0063375 A1 3/2010 Kassab et al.
2010/0063562 A1 3/2010 Cowan et al.
2010/0065871 A1 3/2010 Govari et al.
2010/0094367 A1 4/2010 Sen
2010/0114209 A1 5/2010 Krause et al.
2010/0114214 A1 5/2010 Morelli et al.
2010/0125281 A1 5/2010 Jacobson et al.
2010/0152798 A1 6/2010 Sanghera et al.
2010/0168761 A1 7/2010 Kassab et al.
2010/0168777 A1 7/2010 Stangenes
2010/0168819 A1 7/2010 Freeberg
2010/0185250 A1 7/2010 Rom
2010/0198288 A1 8/2010 Ostroff
2010/0198291 A1 8/2010 Sambelashvili et al.
2010/0198304 A1 8/2010 Wang
2010/0217367 A1 8/2010 Belson
2010/0228308 A1 9/2010 Cowan et al.
2010/0234906 A1 9/2010 Koh
2010/0234924 A1 9/2010 Willis
2010/0241185 A1 9/2010 Mahapatra et al.
2010/0249729 A1 9/2010 Morris et al.
2010/0286541 A1 11/2010 Musley et al.
2010/0286626 A1 11/2010 Petersen
2010/0286744 A1 11/2010 Echt et al.
2010/0298841 A1 11/2010 Prinzen et al.
2010/0312309 A1 12/2010 Harding
2011/0022113 A1 1/2011 Zdeblick et al.
2011/0071586 A1 3/2011 Jacobson
2011/0077708 A1 3/2011 Ostroff

(56) References Cited

U.S. PATENT DOCUMENTS

2011/0106202 A1 5/2011 Ding et al.
2011/0112398 A1 5/2011 Zarkh et al.
2011/0112600 A1 5/2011 Cowan et al.
2011/0118588 A1 5/2011 Komblau et al.
2011/0118810 A1 5/2011 Cowan et al.
2011/0137187 A1 6/2011 Yang et al.
2011/0144720 A1 6/2011 Cowan et al.
2011/0152970 A1 6/2011 Jollota et al.
2011/0160558 A1 6/2011 Rassatt et al.
2011/0160565 A1 6/2011 Stubbs
2011/0160801 A1 6/2011 Markowitz et al.
2011/0160806 A1 6/2011 Lyden et al.
2011/0166620 A1 7/2011 Cowan et al.
2011/0166621 A1 7/2011 Cowan et al.
2011/0184491 A1 7/2011 Kivi
2011/0190835 A1 8/2011 Brockway et al.
2011/0190841 A1 8/2011 Sambelashvili et al.
2011/0196444 A1 8/2011 Prakash et al.
2011/0208260 A1 8/2011 Jacobson
2011/0218587 A1 9/2011 Jacobson
2011/0230734 A1 9/2011 Fain et al.
2011/0237967 A1 9/2011 Moore et al.
2011/0245890 A1 10/2011 Brisben et al.
2011/0251660 A1 10/2011 Griswold
2011/0251662 A1 10/2011 Griswold et al.
2011/0270099 A1 11/2011 Ruben et al.
2011/0270339 A1 11/2011 Murray, III et al.
2011/0270340 A1 11/2011 Pellegrini et al.
2011/0276102 A1 11/2011 Cohen
2011/0282423 A1 11/2011 Jacobson
2012/0004527 A1 1/2012 Thompson et al.
2012/0029323 A1 2/2012 Zhao
2012/0035685 A1 2/2012 Saha et al.
2012/0041508 A1 2/2012 Rousso et al.
2012/0059433 A1 3/2012 Cowan et al.
2012/0059436 A1 3/2012 Fontaine et al.
2012/0065500 A1 3/2012 Rogers et al.
2012/0078322 A1 3/2012 Dal Molin et al.
2012/0089198 A1 4/2012 Ostroff
2012/0089214 A1 4/2012 Kroll et al.
2012/0093245 A1 4/2012 Makdissi et al.
2012/0095521 A1 4/2012 Hintz
2012/0095539 A1 4/2012 Khairkhahan et al.
2012/0101540 A1 4/2012 O'Brien et al.
2012/0101553 A1 4/2012 Reddy
2012/0109079 A1* 5/2012 Asleson ................ A61F 2/2427 606/129
2012/0109148 A1 5/2012 Bonner et al.
2012/0109149 A1 5/2012 Bonner et al.
2012/0109235 A1 5/2012 Sheldon et al.
2012/0109236 A1 5/2012 Jacobson et al.
2012/0109259 A1 5/2012 Bond et al.
2012/0116489 A1 5/2012 Khairkhahan et al.
2012/0150251 A1 6/2012 Giftakis et al.
2012/0158111 A1 6/2012 Khairkhahan et al.
2012/0165827 A1 6/2012 Khairkhahan et al.
2012/0172690 A1 7/2012 Anderson et al.
2012/0172891 A1 7/2012 Lee
2012/0172892 A1 7/2012 Grubac et al.
2012/0172942 A1 7/2012 Berg
2012/0197350 A1 8/2012 Roberts et al.
2012/0197373 A1 8/2012 Khairkhahan et al.
2012/0215285 A1 8/2012 Tahmasian et al.
2012/0232478 A1 9/2012 Haslinger
2012/0232565 A1 9/2012 Kveen et al.
2012/0245665 A1 9/2012 Friedman et al.
2012/0263218 A1 10/2012 Dal Molin et al.
2012/0277600 A1 11/2012 Greenhut
2012/0277606 A1 11/2012 Ellingson et al.
2012/0283587 A1 11/2012 Gosh et al.
2012/0283795 A1 11/2012 Stancer et al.
2012/0283807 A1 11/2012 Deterre et al.
2012/0284003 A1 11/2012 Gosh et al.
2012/0290025 A1 11/2012 Keimel
2012/0296228 A1 11/2012 Zhang et al.
2012/0296381 A1 11/2012 Matos
2012/0303082 A1 11/2012 Dong et al.
2012/0316613 A1 12/2012 Keefe et al.
2013/0012151 A1 1/2013 Hankins
2013/0013017 A1 1/2013 Mullen et al.
2013/0023975 A1 1/2013 Locsin
2013/0035748 A1 2/2013 Bonner et al.
2013/0041422 A1 2/2013 Jacobson
2013/0053906 A1 2/2013 Ghosh et al.
2013/0053908 A1 2/2013 Smith et al.
2013/0053915 A1 2/2013 Holmstrom et al.
2013/0053921 A1 2/2013 Bonner et al.
2013/0060298 A1 3/2013 Splett et al.
2013/0066169 A1 3/2013 Rys et al.
2013/0072770 A1 3/2013 Rao et al.
2013/0079798 A1 3/2013 Tran et al.
2013/0079861 A1 3/2013 Reinert et al.
2013/0085350 A1 4/2013 Schugt et al.
2013/0085403 A1 4/2013 Gunderson et al.
2013/0085550 A1 4/2013 Polefko et al.
2013/0096649 A1 4/2013 Martin et al.
2013/0103047 A1 4/2013 Steingisser et al.
2013/0103109 A1 4/2013 Jacobson
2013/0110008 A1 5/2013 Bourg et al.
2013/0110127 A1 5/2013 Bornzin et al.
2013/0110192 A1 5/2013 Tran et al.
2013/0110219 A1 5/2013 Bornzin et al.
2013/0116529 A1 5/2013 Min et al.
2013/0116738 A1* 5/2013 Samade ............... A61N 1/3684 607/9
2013/0116739 A1 5/2013 Brada et al.
2013/0116740 A1* 5/2013 Bornzin ............... A61N 1/3684 607/9
2013/0116741 A1 5/2013 Bornzin et al.
2013/0123872 A1 5/2013 Bornzin et al.
2013/0123875 A1 5/2013 Varady et al.
2013/0131591 A1 5/2013 Berthiaume et al.
2013/0131693 A1 5/2013 Berthiaume et al.
2013/0131750 A1 5/2013 Stadler et al.
2013/0131751 A1 5/2013 Stadler et al.
2013/0138006 A1 5/2013 Bornzin et al.
2013/0150695 A1 6/2013 Biela et al.
2013/0150911 A1 6/2013 Perschbacher et al.
2013/0150912 A1 6/2013 Perschbacher et al.
2013/0184776 A1 7/2013 Shuros et al.
2013/0196703 A1 8/2013 Masoud et al.
2013/0197599 A1 8/2013 Sambelashvili et al.
2013/0197609 A1 8/2013 Moore et al.
2013/0231710 A1 9/2013 Jacobson
2013/0238072 A1 9/2013 Deterre et al.
2013/0238073 A1 9/2013 Makdissi et al.
2013/0253342 A1 9/2013 Griswold et al.
2013/0253343 A1 9/2013 Walfhauser et al.
2013/0253344 A1 9/2013 Griswold et al.
2013/0253345 A1 9/2013 Griswold et al.
2013/0253346 A1 9/2013 Griswold et al.
2013/0253347 A1 9/2013 Griswold et al.
2013/0261497 A1 10/2013 Pertijs et al.
2013/0265144 A1 10/2013 Banna et al.
2013/0268017 A1 10/2013 Zhang et al.
2013/0268042 A1 10/2013 Hastings et al.
2013/0274828 A1 10/2013 Willis
2013/0274847 A1 10/2013 Ostroff
2013/0282070 A1 10/2013 Cowan et al.
2013/0282073 A1 10/2013 Cowan et al.
2013/0296727 A1 11/2013 Sullivan et al.
2013/0303872 A1 11/2013 Taff et al.
2013/0324825 A1 12/2013 Ostroff et al.
2013/0325081 A1* 12/2013 Karst ..................... A61B 5/349 607/25
2013/0345770 A1 12/2013 Dianaty et al.
2014/0012344 A1 1/2014 Hastings et al.
2014/0018876 A1 1/2014 Ostroff
2014/0018877 A1 1/2014 Demmer et al.
2014/0031836 A1 1/2014 Ollivier
2014/0039591 A1 2/2014 Drasler et al.
2014/0043146 A1 2/2014 Makdissi et al.
2014/0046395 A1 2/2014 Regnier et al.
2014/0046420 A1 2/2014 Moore et al.

(56) References Cited

U.S. PATENT DOCUMENTS

2014/0058240 A1 2/2014 Mothilal et al.
2014/0058494 A1 2/2014 Ostroff et al.
2014/0074114 A1 3/2014 Khairkhahan et al.
2014/0074186 A1 3/2014 Faltys et al.
2014/0094891 A1 4/2014 Pare et al.
2014/0100627 A1 4/2014 Min
2014/0107723 A1* 4/2014 Hou .................... A61N 1/3756 607/9
2014/0114173 A1 4/2014 Bar-Tal et al.
2014/0114372 A1 4/2014 Ghosh et al.
2014/0121719 A1 5/2014 Bonner et al.
2014/0121720 A1 5/2014 Bonner et al.
2014/0121722 A1 5/2014 Sheldon et al.
2014/0128935 A1 5/2014 Kumar et al.
2014/0135865 A1 5/2014 Hastings et al.
2014/0142648 A1 5/2014 Smith et al.
2014/0148675 A1 5/2014 Nordstrom et al.
2014/0148815 A1 5/2014 Wenzel et al.
2014/0155950 A1 6/2014 Hastings et al.
2014/0169162 A1 6/2014 Romano et al.
2014/0172034 A1* 6/2014 Bornzin ................. A61N 1/368 607/9
2014/0172060 A1 6/2014 Bornzin et al.
2014/0180306 A1 6/2014 Grubac et al.
2014/0180366 A1 6/2014 Edlund
2014/0207149 A1 7/2014 Hastings et al.
2014/0207210 A1 7/2014 Willis et al.
2014/0214104 A1 7/2014 Greenhut et al.
2014/0222098 A1 8/2014 Baru et al.
2014/0222109 A1 8/2014 Moulder
2014/0228913 A1 8/2014 Molin et al.
2014/0236172 A1 8/2014 Hastings et al.
2014/0243848 A1* 8/2014 Auricchio .......... A61N 1/37205 607/32
2014/0255298 A1 9/2014 Cole et al.
2014/0257324 A1 9/2014 Fain
2014/0257422 A1 9/2014 Herken
2014/0257444 A1 9/2014 Cole et al.
2014/0276929 A1 9/2014 Foster et al.
2014/0303704 A1 10/2014 Suwito et al.
2014/0309706 A1 10/2014 Jacobson
2014/0323882 A1 10/2014 Ghosh et al.
2014/0323892 A1 10/2014 Ghosh et al.
2014/0330208 A1 11/2014 Christie et al.
2014/0330287 A1 11/2014 Thompson-Nauman et al.
2014/0330326 A1 11/2014 Thompson-Nauman et al.
2014/0339570 A1 11/2014 Mollard et al.
2014/0358135 A1 12/2014 Sambelashvili et al.
2014/0371832 A1 12/2014 Ghosh
2014/0371833 A1 12/2014 Ghosh et al.
2014/0379041 A1 12/2014 Foster
2015/0025612 A1 1/2015 Haasl et al.
2015/0039041 A1 2/2015 Smith et al.
2015/0051609 A1 2/2015 Schmidt et al.
2015/0051610 A1 2/2015 Schmidt et al.
2015/0051611 A1 2/2015 Schmidt et al.
2015/0051612 A1 2/2015 Schmidt et al.
2015/0051613 A1 2/2015 Schmidt et al.
2015/0051614 A1 2/2015 Schmidt et al.
2015/0051615 A1 2/2015 Schmidt et al.
2015/0051616 A1 2/2015 Haasl et al.
2015/0051682 A1 2/2015 Schmidt et al.
2015/0057520 A1 2/2015 Foster et al.
2015/0057558 A1 2/2015 Stahmann et al.
2015/0057721 A1 2/2015 Stahmann et al.
2015/0088155 A1 3/2015 Foster et al.
2015/0105836 A1 4/2015 Bonner et al.
2015/0142070 A1 5/2015 Sambelashvili
2015/0148697 A1 5/2015 Burnes et al.
2015/0149096 A1 5/2015 Soykan
2015/0157861 A1 6/2015 Aghassian
2015/0173655 A1 6/2015 Demmer et al.
2015/0190638 A1 7/2015 Smith et al.
2015/0196756 A1 7/2015 Stahmann et al.
2015/0196757 A1 7/2015 Stahmann et al.
2015/0196758 A1 7/2015 Stahmann et al.
2015/0196769 A1 7/2015 Stahmann et al.
2015/0217119 A1 8/2015 Nikolski et al.
2015/0221898 A1 8/2015 Chi et al.
2015/0224315 A1 8/2015 Stahmann
2015/0224320 A1 8/2015 Stahmann
2015/0258345 A1 9/2015 Smith et al.
2015/0290468 A1 10/2015 Zhang
2015/0297905 A1 10/2015 Greenhut et al.
2015/0297907 A1 10/2015 Zhang
2015/0305637 A1 10/2015 Greenhut et al.
2015/0305638 A1 10/2015 Zhang
2015/0305639 A1 10/2015 Greenhut et al.
2015/0305640 A1 10/2015 Reinke et al.
2015/0305641 A1 10/2015 Stadler et al.
2015/0305642 A1 10/2015 Reinke et al.
2015/0305695 A1 10/2015 Lahm et al.
2015/0306374 A1 10/2015 Seifert et al.
2015/0306375 A1 10/2015 Marshall et al.
2015/0306406 A1 10/2015 Crutchfield et al.
2015/0306407 A1 10/2015 Crutchfield et al.
2015/0306408 A1 10/2015 Greenhut et al.
2015/0321016 A1 11/2015 O'Brien et al.
2015/0328459 A1 11/2015 Chin et al.
2015/0335894 A1 11/2015 Bornzin et al.
2016/0015287 A1 1/2016 Anderson et al.
2016/0015322 A1 1/2016 Anderson et al.
2016/0023000 A1 1/2016 Cho et al.
2016/0030757 A1 2/2016 Jacobson
2016/0033177 A1 2/2016 Barot et al.
2016/0045738 A1 2/2016 Ghosh et al.
2016/0045744 A1 2/2016 Gillberg et al.
2016/0051821 A1 2/2016 Sambelashvili et al.
2016/0059002 A1 3/2016 Grubac et al.
2016/0067486 A1 3/2016 Brown et al.
2016/0067487 A1 3/2016 Demmer et al.
2016/0067490 A1 3/2016 Carney et al.
2016/0110856 A1 4/2016 Hoof et al.
2016/0114161 A1 4/2016 Amblard et al.
2016/0121127 A1 5/2016 Klimovitch et al.
2016/0121128 A1 5/2016 Fishler et al.
2016/0121129 A1 5/2016 Persson et al.
2016/0129239 A1* 5/2016 Anderson ............. A61M 25/09 606/129
2016/0213919 A1 7/2016 Suwito et al.
2016/0213937 A1 7/2016 Reinke et al.
2016/0213939 A1 7/2016 Carney et al.
2016/0228026 A1 8/2016 Jackson
2016/0228712 A1* 8/2016 Koop ..................... A61N 1/368
2016/0317825 A1 11/2016 Jacobson
2016/0367823 A1 12/2016 Cowan et al.
2017/0014629 A1 1/2017 Ghosh et al.
2017/0035315 A1 2/2017 Jackson
2017/0043173 A1 2/2017 Sharma et al.
2017/0043174 A1 2/2017 Greenhut et al.
2017/0056670 A1 3/2017 Sheldon et al.
2017/0182327 A1 6/2017 Liu
2017/0189681 A1 7/2017 Anderson
2017/0209689 A1 7/2017 Chen
2017/0216575 A1 8/2017 Asleson et al.
2017/0246461 A1 8/2017 Ghosh
2017/0304624 A1 10/2017 Friedman et al.
2017/0326369 A1 11/2017 Koop et al.
2017/0326372 A1 11/2017 Koop
2017/0340885 A1 11/2017 Sambelashvili
2018/0008829 A1 1/2018 An et al.
2018/0021567 A1 1/2018 An et al.
2018/0021581 A1 1/2018 An et al.
2018/0021582 A1 1/2018 An et al.
2018/0050208 A1 2/2018 Shuros et al.
2018/0078773 A1 3/2018 Thakur et al.
2018/0078779 A1 3/2018 An et al.
2018/0117324 A1 5/2018 Schilling et al.
2018/0140848 A1 5/2018 Stahmann
2018/0178007 A1 6/2018 Shuros et al.
2018/0212451 A1 7/2018 Schmidt et al.
2018/0264262 A1 9/2018 Haasl et al.
2018/0264272 A1 9/2018 Haasl et al.
2018/0264273 A1 9/2018 Haasl et al.

(56) References Cited

U.S. PATENT DOCUMENTS

| | | | | |
|---|---|---|---|---|
| 2018/0264274 | A1 | 9/2018 | Haasl et al. | |
| 2018/0280686 | A1 | 10/2018 | Shuros et al. | |
| 2018/0326215 | A1 | 11/2018 | Ghosh | |
| 2019/0030346 | A1 | 1/2019 | Li | |
| 2019/0038906 | A1 | 2/2019 | Koop et al. | |
| 2019/0083779 | A1 | 3/2019 | Yang et al. | |
| 2019/0083800 | A1 | 3/2019 | Yang et al. | |
| 2019/0083801 | A1 | 3/2019 | Yang et al. | |
| 2019/0143118 | A1* | 5/2019 | Bullinga | A61N 1/37512 607/17 |
| 2019/0192863 | A1* | 6/2019 | Koop | A61N 1/37516 |
| 2019/0290905 | A1 | 9/2019 | Yang et al. | |
| 2019/0290909 | A1 | 9/2019 | Ghosh | |
| 2019/0298990 | A1 | 10/2019 | De Kock et al. | |
| 2019/0314636 | A1 | 10/2019 | Shuros et al. | |
| 2019/0351236 | A1* | 11/2019 | Koop | A61N 1/3756 |
| 2020/0009380 | A1* | 1/2020 | Casavant | A61N 1/365 |

FOREIGN PATENT DOCUMENTS

| | | | |
|---|---|---|---|
| AU | 2014203793 | A1 | 7/2014 |
| CN | 202933393 | | 5/2013 |
| EP | 0362611 | A1 | 4/1990 |
| EP | 0459 239 | A2 | 12/1991 |
| EP | 0 728 497 | A2 | 8/1996 |
| EP | 1 541 191 | A1 | 6/2005 |
| EP | 1 702 648 | A1 | 9/2006 |
| EP | 1 904 166 | B1 | 6/2011 |
| EP | 2 452 721 | A1 | 5/2012 |
| EP | 2 471 452 | A1 | 7/2012 |
| EP | 2 662 113 | A2 | 11/2013 |
| EP | 1 703 944 | B1 | 7/2015 |
| JP | 2005245215 | | 9/2005 |
| WO | WO 95/00202 | | 1/1995 |
| WO | WO 96/36134 | | 11/1996 |
| WO | WO 97/24981 | | 7/1997 |
| WO | WO 02/22206 | A1 | 3/2002 |
| WO | WO 03/092800 | A1 | 11/2003 |
| WO | WO 2005/000206 | A2 | 1/2005 |
| WO | WO 2005/042089 | A1 | 5/2005 |
| WO | WO 2006/086435 | A2 | 8/2006 |
| WO | WO 2006/113659 | A1 | 10/2006 |
| WO | WO 2007/073435 | A1 | 6/2007 |
| WO | WO 2007/075974 | A2 | 7/2007 |
| WO | WO 2009/006531 | A1 | 1/2009 |
| WO | WO 2013/080038 | A2 | 6/2013 |
| WO | WO 2013/098644 | A2 | 7/2013 |
| WO | WO 2015/081221 | A1 | 6/2015 |
| WO | WO 2016/011042 | A1 | 1/2016 |
| WO | WO 2016/077099 | A1 | 5/2016 |
| WO | WO 2016/110856 | A1 | 7/2016 |
| WO | WO 2016/171891 | A1 | 10/2016 |
| WO | WO 2017/075193 | A1 | 5/2017 |
| WO | WO 2018/009569 | A1 | 1/2018 |
| WO | WO 2018/017226 | A1 | 1/2018 |
| WO | WO 2018/017361 | A1 | 1/2018 |
| WO | WO 2018/035343 | A1 | 2/2018 |
| WO | WO 2018/081519 | A1 | 5/2018 |

OTHER PUBLICATIONS

Definition of "lumen." Oxford English Dictionary. https://www.oed.com/dictionary/lumen_n.*

Extended European Search Report for Application No. 20894751.5 dated Feb. 12, 2024 (12 pages).

U.S. Appl. No. 10/039,305 B2, Asleson et al..

U.S. Appl. No. 17/070,361, filed Oct. 14, 2020, Hine et al.

U.S. Appl. No. 63/059,878, filed Jul. 31, 2020, Whitman et al.

http://www.isrctn.com/ISRCTN47824547, public posting published Aug. 2019.

Abed et al., "Obesity results in progressive atrial structural and electrical remodeling: Implications for atrial fibrillation," *Heart Rhythm Society*, Jan. 2013; 10(1):90-100.

Adragão et al., "Ablation of pulmonary vein foci for the treatment of atrial fibrillation; percutaneous electroanatomical guided approach," *Europace*, Oct. 2002; 4(4):391-9.

Aliot et al., "Arrhythmia detection by dual-chamber implantable cardioverter defibrillators: A review of current algorithms," *Europace*, Jul. 2004; 6(4):273-86.

Amirahmadi et al., "Ventricular Tachycardia Caused by Mesothelial Cyst," *Indian Pacing and Electrophysiology Journal*, 2013; 13(1):43-44.

Ammirabile et al., "Pitx2 confers left morphological, molecular, and functional identity to the sinus venosus myocardium," *Cardiovasc Res.*, Feb. 2012; 93(2):291-301.

Anderson et al., "Left bundle branch block and the evolving role of QRS morphology in selection of patients for cardiac resynchronization", Journal of Interventional Cardio Electrophysiology, vol. 52, No. 3. Aug. 20. 2018, pp. 353-374.

Anfinsen, "Non-pharmacological Treatment of Atrial Fibrillation," *Indian Pacing and Electrophysiology Journal*, Jan. 2002; 2(1):4-14.

Anné et al., "Ablation of post-surgical intra-atrial reentrant Tachycardia," *European Heart Journal*, 2002; 23:169-1616.

Arenal et al., "Dominant frequency differences in atrial fibrillation patients with and without left ventricular systolic dysfunction," *Europace*, Apr. 2009; 11(4):450-457.

Arriagada et al., "Predictors of arrhythmia recurrence in patients with lone atrial fibrillation," *Europace*, Jan. 2008; 10(1):9-14.

Asirvatham et al., "Cardiac Anatomic Considerations in Pediatric Electrophysiology," *Indian Pacing and Electrophysiology Journal*, Apr. 2008; 8(Suppl 1):S75-S91.

Asirvatham et al., "Intramyocardial Pacing and Sensing for the Enhancement of Cardiac Stimulation and Sensing Specificity," *Pacing Clin. Electrophysiol.*, Jun. 2007; 30(6):748-754.

Asirvatham et al., "Letter to the Editor," *J Cardiovasc Electrophysiol.*, Mar. 2010; 21(3): E77.

Balmer et al., "Long-term follow up of children with congenital complete atrioventricular block and the impact of pacemaker therapy," *Europace*, Oct. 2002; 4(4):345-349.

Barold et al., "Conventional and biventricular pacing in patients with first-degree atrioventricular block," *Europace*, Oct. 2012; 14(10):1414-9.

Barold et al., "The effect of hyperkalaemia on cardiac rhythm devices," *Europace*, Apr. 2014; 16(4):467-76.

Bayrak et al., "Added value of transoesophageal echocardiography during transseptal puncture performed by inexperienced operators," *Europace*, May 2012; 14(5):661-5.

Bergau et al., "Measurement of Left Atrial Pressure is a Good Predictor of Freedom From Atrial Fibrillation," *Indian Pacing and Electrophysiology Journal*, Jul. 2014; 14(4):181-93.

Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.

Bito et al., "Early exercise training after myocardial infarction prevents contractile but not electrical remodeling or hypertrophy," *Cardiovascular Research*, Apr. 2010; 86(1):72-81.

Bollmann et al., "Analysis of surface electrocardiograms in atrial fibrillation: techniques, research, and clinical applications," *Europace*, Nov. 2006; 8(11):911-926.

Bortone et al., "Evidence for an incomplete mitral isthmus block after failed ablation of a left postero-inferior concealed accessory pathway," *Europace*, Jun. 2006; 8(6):434-7.

Boulos et al., "Electroanatomical mapping and radiofrequency ablation of an accessory pathway associated with a large aneurysm of the coronary sinus," *Europace*, Nov. 2004; 6(6):608-12.

Brembilla-Perrot et al., "Incidence and prognostic significance of spontaneous and inducible antidromic tachycardia," *Europace*, Jun. 2013; 15(6):871-876.

Buber et al., "Morphological features of the P-waves at surface electrocardiogram as surrogate to mechanical function of the left atrium following a successful modified maze procedure," *Europace*, Apr. 2014; 16(4):578-86.

(56) References Cited

OTHER PUBLICATIONS

Burashnikov et al., "Late-phase 3 Ead. A unique mechanism contributing to initiation of atrial fibrillation," *Pacing Clin Electrophysiol.*, Mar. 2006; 29(3):290-5.
Burashnikov et al., "Atrial-selective inhibition of sodium-channel current by Wenxin Keli is effective in suppressing atrial fibrillation," *Heart Rhythm*, Jan. 2012; 9(1):125-31.
Calvo et al., "Efficacy of circumferential pulmonary vein ablation of atrial fibrillation in endurance athletes," *Europace*, Jan. 2010; 12(1):30-6.
Can et al., ""Atrial torsades de pointes" Induced by Low-Energy Shock From Implantable-Cardioverter Defibrillator," *Indian Pacing and Electrophysiology Journal*, Sep. 2013; 13(5):194-199.
Carroz et al., "Pseudo-pacemaker syndrome in a young woman with first-degree atrio-ventricular block," *Europace*, Apr. 2010; 12(4):594-596.
Catanchin et al., "Wolff-Parkinson-White syndrome with an unroofed coronary sinus without persistent left superior vena cava treated with catheter cryoablation," *Indian Pacing and Electrophysiology Journal*, Aug. 2008; 8(3):227-233.
Cazeau et al., "Cardiac resynchronization therapy," *Europace*, Sep. 2004; 5 Suppl 1:S42-8.
Cerqueira et al., "Standardized myocardial segmentation and nomenclature for tomographic imaging of the heart. A statement for healthcare professionals from the Cardiac Imaging Committee of the Council on Clinical Cardiology of the American Heart Association," *Circulation*, Jan. 29, 2002; 105(4):539-42.
Chandra et al., "Evaluation of KCB-328, a new IKr blocking antiarrhythmic agent in pacing induced canine atrial fibrillation," *Europace*, Sep. 2004; 6(5):384-91.
Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.
Charron et al., "A familial form of conduction defect related to a mutation in the PRKAG2 gene," *Europace*, Aug. 2007; 9(8):597-600.
Chou et al., "Effects of SEA0400 on Arrhythmogenicity in a Langendorff-Perfused 1-Month Myocardial Infarction Rabbit Model," *Pacing Clin Electrophysiol.*, May 2013; 36(5):596-606.
Ciploetta et al., "Posterior Coronary Vein as the Substrate for an Epicardial Accessory Pathway," *Indian Pacing and Electrophysiology Journal*, Aug. 2013; 13(4):142-7.
Climent et al., "Effects of endocardial microwave energy ablation," *Indian Pacing and Electrophysiology Journal*, Jul. 2005; 5(3):233-43.
Comtois et al., "Of circles and spirals: bridging the gap between the leading circle and spiral wave concepts of cardiac reentry," *Europace*, Sep. 2005; 7 Suppl 2:10-20.
Crick et al., "Anatomy of the pig heart: comparisons with normal human cardiac structure," *J. Anat.*, 1998, 193: 105-119.
Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.
De Mattia et al., "Paroxysmal atrial fibrillation triggered by a monomorphic ventricular couplet in a patient with acute coronary syndrome," *Indian Pacing and Electrophysiology Journal*, Jan. 2012; 12(1):19-23.
DeSimone et al., "New approach to cardiac resynchronization therapy: CRT without left ventricular lead," Apr. 25, 2014, 2 pages.
De Sisti et al., "Electrophysiological determinants of atrial fibrillation in sinus node dysfunction despite atrial pacing," *Europace*, Oct. 2000; 2(4):304-11.
De Voogt et al., "Electrical characteristics of low atrial septum pacing compared with right atrial appendage pacing," *Europace*, Jan. 2005; 7(1):60-6.
De Voogt et al., "A technique of lead insertion for low atrial septal pacing," *Pacing Clin Electrophysiol.*, Jul. 2005; 28(7):639-46.
Dizon et al. "Real-time stroke volume measurements for the optimization of cardiac resynchronization therapy parameters," *Europace*, Sep. 2010; 12(9):1270-1274.
Duckett et al., "Relationship between endocardial activation sequences defined by high-density mapping to early septal contraction (septal flash) in patients with left bundle branch block undergoing cardiac resynchronization therapy," *Europace*, Jan. 2012; 14(1):99-106.
Eksik et al., "Influence of atrioventricular nodal reentrant tachycardia ablation on right to left inter-atrial conduction," *Indian Pacing and Electrophysiology Journal*, Oct. 2005; 5(4):279-88.
Fiala et al., "Left Atrial Voltage during Atrial Fibrillation in Paroxysmal and Persistent Atrial Fibrillation Patients," *PACE*, May 2010; 33(5):541-548.
Fragakis et al., "Acute beta-adrenoceptor blockade improves efficacy of ibutilide in conversion of atrial fibrillation with a rapid ventricular rate," *Europace*, Jan. 2009; 11(1): 70-4.
Frogoudaki et al., "Pacing for adult patients with left atrial isomerism: efficacy and technical considerations," *Europace*, Apr. 2003; 5(2):189-193.
Ganapathy et al., "Implantable Device to Monitor Cardiac Activity with Sternal Wires," *Pacing Clin. Electrophysiol.*, Dec. 2014; Epub Aug. 24, 2014; 37(12):1630-40.
Geddes, "Accuracy limitations of chronaxie values," *IEEE Trans Biomed Eng.*, Jan. 2004; 51(1):176-81.
Gertz et al., "The impact of mitral regurgitation on patients undergoing catheter ablation of atrial fibrillation," *Europace*, Aug. 2011; 13(8):1127-32.
Girmatsion et al., "Changes in microRNA-1 expression and IK1 up-regulation in human atrial fibrillation," *Heart Rhythm*, Dec. 2009; 6(12):1802-9.
Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.
Goette et al., "Electrophysiological effects of angiotensin II. Part I: signal transduction and basic electrophysiological mechanisms," *Europace*, Feb. 2008; 10(2):238-41.
Gómez et al., "Nitric oxide inhibits Kv4.3 and human cardiac transient outward potassium current (Ito1)," *Cardiovasc Res.*, Dec. 2008; 80(3):375-84.
Gros et al., "Connexin 30 is expressed in the mouse sino-atrial node and modulates heart rate," *Cardiovascular Research*, Jan. 2010; 85(1):45-55.
Guenther et al., "Substernal Lead Implantation: A Novel Option to Manage OFT Failure in S-ICD patients," *Clinical Research Cardiology*, Feb. 2015; Epub Oct. 2, 2014; 104(2): 189-91.
Guillem et al., "Noninvasive mapping of human atrial fibrillation," *J Cardiovasc Electrophysiol.*, May 2009; 20(5):507-513.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Hakacova et al., "Septal atrial pacing for the prevention of atrial fibrillation," *Europace*, 2007; 9:1124-1128.
Hasan et al., "Safety, efficacy, and performance of implanted recycled cardiac rhythm management (CRM) devices in underprivileged patients," *Pacing Clin Electrophysiol.*, Jun. 2011; 34(6):653-8.
Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.
He et al., "Three-dimensional cardiac electrical imaging from intracavity recordings," *IEEE Trans Biomed Eng.*, Aug. 2007; 54(8):1454-60.
Heist et al., "Direct visualization of epicardial structures and ablation utilizing a visually guided laser balloon catheter: preliminary findings," *J Cardiovasc Electrophysiol.*, Jul. 2011; 22(7):808-12.
Henz et al., "Synchronous Ventricular Pacing without Crossing the Tricuspid Valve or Entering the Coronary Sinus-Preliminary Results," *J Cardiovasc Electrophysiol.*, Dec. 2009; 20(12):1391-1397.

(56) References Cited

OTHER PUBLICATIONS

Hiippala et al., "Automatic Atrial Threshold Measurement and Adjustment in Pediatric Patients," *Pacing Clin Electrophysiol.*, Mar. 2010; 33(3):309-13.
Ho, "Letter to the Editor" *J Cardiovasc Electrophysiol.*, Mar. 2010; 21(3): E76.
Höijer et al., "Improved cardiac function and quality of life following upgrade to dual chamber pacing after long-term ventricular stimulation," *European Heart Journal*, Mar. 2002; 23(6):490-497.
Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.e1-1736.e.
Inter-Office Memo, Model 6426-85 Canine Feasibility AV Septal 8 mm Screw-In Right Single Pass DDD Lead Final Report (AR # 0120A0207).
Ishigaki et al., "Prevention of immediate recurrence of atrial fibrillation with low-dose landiolol after radiofrequency catheter ablation," *Journal of Arrhythmia*, Oct. 2015; 31(5):279-285.
Israel, "The role of pacing mode in the development of atrial fibrillation," *Europace*, Feb. 2006; 8(2):89-95.
Janion et al., "Dispersion of P wave duration and P wave vector in patients with atrial septal aneurysm," *Europace*, Jul. 2007; 9(7):471-4.
Kabra et al., "Recent Trends in Imaging for Atrial Fibrillation Ablation," *Indian Pacing and Electrophysiology Journal*, 2010; 10(5):215-227.
Kalbfleisch et al., "Catheter Ablation with Radiofrequency Energy: Biophysical Aspects and Clinical Applications," *Journal of Cardiovascular Electrophysiology*, Oct. 2008; 3(2):173-186.
Katritsis et al., "Classification and differential diagnosis of atrioventricular nodal re- entrant tachycardia," *Europace*, Jan. 2006; 8(1):29-36.
Katritsis et al., "Anatomically left-sided septal slow pathway ablation in dextrocardia and situs inversus totalis," *Europace*, Aug. 2008; 10(8):1004-5.
Khairy et al., "Cardiac Arrhythmias In Congenital Heart Diseases," *Indian Pacing and Electrophysiology Journal*, Nov.-Dec. 2009; 9(6):299-317.
Kimmel et al., "Single-site ventricular and biventricular pacing: investigation of latest depolarization strategy," *Europace*, Dec. 2007; 9(12):1163-1170.
Knackstedt et al., "Electro-anatomic mapping systems in arrhythmias," *Europace*, Nov. 2008; 10 Suppl 3:iii28-ili34.
Kobayashi et al., "Successful Ablation of Antero-septal Accessory Pathway in the Non-Coronary Cusp in a Child," *Indian Pacing and Electrophysiology Journal*, 2012; 12(3):124-130.
Kojodjojo et al., "4:2:1 conduction of an AF initiating trigger," *Indian Pacing and Electrophysiology Journal*, Nov. 2015; 15(5):255-8.
Kołodzińska et al., "Differences in encapsulating lead tissue in patients who underwent transvenous lead removal," *Europace*, Jul. 2012; 14(7):994-1001.
Konecny et al., "Synchronous intra-myocardial ventricular pacing without crossing the tricuspid valve or entering the coronary sinus," *Cardiovascular Revascularization Medicine*, 2013; 14:137-138.
Kriatselis et al., "Ectopic atrial tachycardias with early activation at His site: radiofrequency ablation through a retrograde approach," *Europace*, Jun. 2008; 10(6):698-704.
Lalu et al., "Ischaemia-reperfusion injury activates matrix metalloproteinases in the human heart," *Eur Heart J.*, Jan. 2005; 26(1):27-35.
Laske et al., "Excitation of the Intrinsic Conduction System Through His and Interventricular Septal Pacing," *Pacing Clin. Electrophysiol.*, Apr. 2006; 29(4):397-405.
Leclercq, "Problems and troubleshooting in regular follow-up of patients with cardiac resynchronization therapy," *Europace*, Nov. 2009; 11 Suppl 5:v66-71.
Lee et al., "An unusual atrial tachycardia in a patient with Friedreich ataxia," *Europace*, Nov. 2011; 13(11):1660-1.
Lee et al., "Blunted Proarrhythmic Effect of Nicorandil in a Langendorff-Perfused Phase-2 Myocardial Infarction Rabbit Model," *Pacing Clin Electrophysiol.*, Feb. 2013; 36(2):142-51.
Lemay et al., "Spatial dynamics of atrial activity assessed by the vectorcardiogram: from sinus rhythm to atrial fibrillation," *Europace*, Nov. 2007; 9 Suppl 6:vi109-18.
Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.
Lewalter et al., "Comparison of spontaneous atrial fibrillation electrogram potentials to the P wave electrogram amplitude in dual chamber pacing with unipolar atrial sensing," *Europace*, Apr. 2000; 2(2):136-40.
Liakopoulos et al., "Sequential deformation and physiological considerations in unipolar right and left ventricular pacing," *European Journal of Cardio-thoracic Surgery*, Apr. 1, 2006; 29S1:S188-197.
Lian et al., "Computer modeling of ventricular rhythm during atrial fibrillation and ventricular pacing," *IEEE Transactions on Biomedical Engineering*, Aug. 2006; 53(8):1512-1520.
Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.
Lim et al., "Coupled pacing improves left ventricular function during simulated atrial fibrillation without mechanical dyssynchrony," *Europace*, Mar. 2010; 12(3):430-6.
Lou et al., "Tachy-brady arrhythmias: The critical role of adenosine-induced sinoatrial conduction block in post-tachycardia pauses," *Heart Rhythm.*, Jan. 2013; 10(1):110-8.
Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.
Macedo et al., "Septal accessory pathway: anatomy, causes for difficulty, and an approach to ablation," *Indian Pacing and Electrophysiology Journal*, Jul. 2010; 10(7):292-309.
Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3):e003344.
Mani et al., "Dual Atrioventricular Nodal Pathways Physiology: A Review of Relevant Anatomy, Electrophysiology, and Electrocardiogramanifestations," *Indian Pacing and Electrophysiology Journal*, Jan. 2014; 14(1):12-25.
Manios et al., "Effects of successful cardioversion of persistent atrial fibrillation on right ventricular refractoriness and repolarization," *Europace*, Jan. 2005; 7(1):34-9.
Manolis et al., "Prevention of atrial fibrillation by inter-atrial septum pacing guided by electrophysiological testing, in patients with delayed interatrial conduction," *Europace*, Apr. 2002; 4(2):165-174.
Marino et al., "Inappropriate mode switching clarified by using a chest radiograph," *Journal of Arrhythmia*, Aug. 2015; 31(4):246-248.
Markowitz et al., "Time course and predictors of autonomic dysfunction after ablation of the slow atrioventricular nodal pathway," *Pacing Clin Electrophysiol.*, Dec. 2004; 27(12):1638-43.
Marshall et al., "The effects of temperature on cardiac pacing thresholds," *Pacing Clin Electrophysiol.*, Jul. 2010; 33(7):826-833.
Mcsharry et al., "A Dynamical Model for Generating Synthetic Electrocardiogram Signals," *IEEE Transactions on Biomedical Engineering*, Mar. 2003; 50(3):289-294.
Meijler et al., "Scaling of Atrioventricular Transmission in Mammalian Species: An Evolutionary Riddle!," *Journal of Cfardiovascular Electrophysiology*, Aug. 2002; 13(8):826-830.
Meiltz et al., "Permanent form of junctional reciprocating tachycardia in adults: peculiar features and results of radiofrequency catheter ablation," *Europace*, Jan. 2006; 8(1):21-8.
Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.

(56) References Cited

OTHER PUBLICATIONS

Mestan et al., "The influence of fluid and diuretic administration on the index of atrial contribution in sequentially paced patients," *Europace*, Apr. 2006; 8(4):273-8.
Metin et al., "Assessment of the P Wave Dispersion and Duration in Elite Women Basketball Players," *Indian Pacing and Electrophysiology Journal*, 2010; 10(1):11-20.
Mills et al., "Left Ventricular Septal and Left Ventricular Apical Pacing Chronically Maintain Cardiac Contractile Coordination, Pump Function and Efficiency," *Circ Arrhythm Electrophysoil.*, Oct. 2009; 2(5):571-579.
Mitchell et al., "How do atrial pacing algorithms prevent atrial arrhythmias?" *Europace*, Jul. 2004; 6(4):351-62.
Mirzoyev et al., "Embryology of the Conduction System for the Electrophysiologist," *Indian Pacing and Electrophysiology Journal*, 2010; 10(8):329-338.
Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.
Montgomery et al., "Measurement of diffuse ventricular fibrosis with myocardial T1 in patients with atrial fibrillation," *J Arrhythm.*, Feb. 2016; 32(1):51-6.
Mulpuru et al., "Synchronous ventricular pacing with direct capture of the atrioventricular conduction system: Functional anatomy, terminology, and challenges," *Heart Rhythm*, Nov. 2016; Epub Aug. 3, 2016; 13(11):2237-2246.
Musa et al., "Inhibition of Platelet-Derived Growth Factor-AB Signaling Prevents Electromechanical Remodeling of Adult Atrial Myocytes that Contact Myofibroblasts," *Heart Rhythm*, Jul. 2013; 10(7):1044-1051.
Nagy et al., "Wnt-11 signalling controls ventricular myocardium development by patterning N-cadherin and B-catenin expression," *Cardiovascular Research*, Jan. 2010; 85(1):100-9.
Namboodiri et al., "Electrophysiological features of atrial flutter in cardiac sarcoidosis: a report of two cases," *Indian Pacing and Electrophysiology Journal*, Nov. 2012; 12(6):284-9.
Nanthakumar et al., "Assessment of accessory pathway and atrial refractoriness by transesophageal and intracardiac atrial stimulation: An analysis of methodological agreement," *Europace*, Jan. 1999; 1(1):55-62.
Neto et al., "Temporary atrial pacing in the prevention of postoperative atrial fibrillation," *Pacing Clin Electrophysiol.*, Jan. 2007; 30(Suppl 1):S79-83.
Nishijima et al., "Tetrahydrobiopterin depletion and Nos. 2 uncoupling contribute to heart failure-induced alterations in atrial electrophysiology," *Cardiovasc Res.*, Jul. 2011; 91(1):71-9.
Niwano et al., "Effect of oral L-type calcium channel blocker on repetitive paroxysmal atrial fibrillation: spectral analysis of fibrillation waves in the Holter monitoring," *Europace*, Dec. 2007; 9(12):1209-1215.
Okumura et al., "Effects of a high-fat diet on the electrical properties of porcine atria," *Journal of Arrhythmia*, Dec. 2015; 31(6):352-358.
Olesen et al., "Mutations in sodium channel β-subunit SCN3B are associated with early-onset lone atrial fibrillation," *Cardiovascular Research*, Mar. 2011; 89(4):786-93.
Ozmen et al., "P wave dispersion is increased in pulmonary stenosis," *Indian Pacing and Electrophysiology Journal*, Jan. 2006; 6(1):25-30.
Packer et al., "New generation of electro-anatomic mapping: Full intracardiac image integration," *Europace*, Nov. 2008; 10 Suppl 3:iii35-41.
Page et al., "Ischemic ventricular tachycardia presenting as a narrow complex tachycardia," *Indian Pacing and Electrophysiology Journal*, Jul. 2014; 14(4):203-210.
Pakarinen et al., "Pre-implant determinants of adequate long-term function of single lead VDD pacemakers," *Europace*, Apr. 2002; 4:137-141.
Patel et al., "Atrial Fibrillation after Cardiac Surgery: Where are we now?" *Indian Pacing and Electrophysiology Journal*, Oct.-Dec. 2008; 8(4):281-291.
Patel et al., "Successful ablation of a left-sided accessory pathway in a patient with coronary sinus atresia and arteriovenous fistula: clinical and developmental insights," *Indian Pacing and Electrophysiology Journal*, Mar. 2011; 11(2):43-49.
Peschar et al., "Left Ventricular Septal and Apex Pacing for Optimal Pump Function in Canine Hearts," *J Am Coll Cardiol.*, Apr. 2, 2003; 41(7):1218-1226.
Physiological Research Laboratories, Final Report for an Acute Study for Model 6426-85 AV Septal Leads, Feb. 1996.
Porciani et al., "Interatrial septum pacing avoids the adverse effect of interatrial delay in biventricular pacing: an echo-Doppler evaluation," *Europace*, Jul. 2002; 4(3):317-324.
Potse et al., "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.
Prystowsky et al., "Case studies with the experts: management decisions in atrial fibrillation," *J Cardiovasc Electrophysiol.*, Feb. 2008; 19(Suppl. 1):S1-12.
Prystowsky, "The history of atrial fibrillation: the last 100 years," *J Cardiovasc Electrophysiol*, Jun. 2008; 19(6):575-582.
Pytkowski et al., "Paroxysmal atrial fibrillation is associated with increased intra-atrial conduction delay," *Europace*, Dec. 2008; 10(12):1415-20.
Qu et al., "Dynamics and cardiac arrhythmias," *J Cardiovasc Electrophysiol.*, Sep. 2006; 17(9):1042-9.
Ravens et al., "Role of potassium currents in cardiac arrhythmias," *Europace*, Oct. 2008; 10(10):1133-7.
Ricci et al., Efficacy of a dual chamber defibrillator with atrial antitachycardia functions in treating spontaneous atrial tachyarrhythmias in patients with life-threatening ventricular tachyarrhythmias, *European Heart Journal*, Sep. 2002; 23(18):1471-9.
Roberts-Thomson et al., "Focal atrial tachycardia II: management," *Pacing Clin Electrophysiol.*, Jul. 2006; 29(7):769-78.
Rossi et al., "Endocardial vagal atrioventricular node stimulation in humans: reproducibility on 18-month follow-up," *Europace*, Dec. 2010; 12(12):1719-24.
Rouzet et al., "Contraction delay of the RV outflow tract in patients with Brugada syndrome is dependent on the spontaneous ST-segment elevation pattern," *Heart Rhythm*, Dec. 2011; 8(12):1905-12.
Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010, 21(2): 219-22.
Sairaku et al., "Prediction of sinus node dysfunction in patients with persistent atrial flutter using the flutter cycle length," *Europace*, Mar. 2012; 14(3):380-7.
Santini et al., "Immediate and long-term atrial sensing stability in single-lead VDD pacing depends on right atrial dimensions," *Europace*, Oct. 2001; 3(4):324-31.
Saremi et al., "Cardiac Conduction System: Delineation of Anatomic Landmarks With Multidetector CT," *Indian Pacing and Electrophysiology Journal*, Nov. 2009; 9(6):318-33.
Savelieva et al., "Anti-arrhythmic drug therapy for atrial fibrillation: current anti-arrhythmic drugs, investigational agents, and innovative approaches," *Europace*, Jun. 2008; 10(6):647-665.
Schmidt et al., "Navigated DENSE strain imaging for post-radiofrequency ablation lesion assessment in the swine left atria," *Europace*, Jan. 2014; 16(1):133-41.
Schoonderwoerd et al., "Rapid Pacing Results in Changes in Atrial but not in Ventricular Refractoriness," *Pacing Clin Electrophysiol.*, Mar. 2002; 25(3):287-90.
Schoonderwoerd et al., "Atrial natriuretic peptides during experimental atrial tachycardia: role of developing tachycardiomyopathy," *J Cardiovasc Electrophysiol.*, Aug. 2004; 15(8):927-32.

(56) References Cited

OTHER PUBLICATIONS

Schoonderwoerd et al., "Atrial ultrastructural changes during experimental atrial tachycardia depend on high ventricular rate," *J Cardiovasc Electrophysiol.*, Oct. 2004; 15(10):1167-74.
Sedmera, "Function and form in the developing cardiovascular system," *Cardiovasc Res.*, Jul. 2011; 91(2):252-9.
Severi et al., "Alterations of atrial electrophysiology induced by electrolyte variations: combined computational and P-wave analysis," *Europace*, Jun. 2010; 12(6):842-9.
Seyedi et al., "A Survey on Intrabody Communications for Body Area Network Application," IEEE Transactions on Biomedical Engineering, vol. 60(8): 2067-2079, 2013.
Shah et al., "Stable atrial sensing on long-term follow up of VDD pacemakers," *Indian Pacing and Electrophysiology Journal*, Oct. 2006; 6(4):189-93.
Shenthar et al., "Permanent pacemaker implantation in a patient with situs solitus, dextrocardia, and corrected transposition of the great arteries using a novel angiographic technique," *Journal of Arrhythmia*, Apr. 2014; 30(2):134-138.
Shenthar et al., "Transvenous permanent pacemaker implantation in dextrocardia: technique, challenges, outcome, and a brief review of literature," *Europace*, Sep. 2014; 16(9):1327-33.
Shirayama, "Role of atrial fibrillation threshold evaluation on guiding treatment," *Indian Pacing and Electrophysiology Journal*, Oct. 2003; 3(4):224-230.
Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.
Spickler et al., "Totally Self-Contained Intracardiac Pacemaker," Journal of Electrocardiology, vol. 3(3&4): 324-331, 1970.
Sreeram et al., "Indications for Electrophysiology Study in children," *Indian Pacing and Electrophysiology Journal*, Apr.-Jun. 2008; 8(Suppl. 1):S36-S54.
Stockburger et al., "Optimization of cardiac resynchronization guided by Doppler echocardiography: haemodynamic improvement and intraindividual variability with different pacing configurations and atrioventricular delays," *Europace*, Oct. 2006; 8(10):881-6.
Stroobandt et al., "Prediction of Wenckebach Behavior and Block Response in DDD Pacemakers," *Pacing Clin Electrophysiol.*, Jun. 2006; 9(6):1040-6.
Suenari et al., "Idiopathic left ventricular tachycardia with dual electrocardiogram morphologies in a single patient," *Europace*, Apr. 2010; 12(4):592-4.
Sweeney et al., "Analysis of Ventricular Activation Using Surface Electrocardiogramadict Left Ventricular Reverse Volumetric Remodeling During Cardiac Resynchronization Therapy," Circulation, Feb. 9, 2010, 121(5): 626-34.
Tan et al., "Electrocardiogramance of ventricular repolarization remodelling during atrial fibrillation," *Europace*, Jan. 2008; 10(1):99-104.
Taramasco et al., "Internal low-energy cardioversion: a therapeutic option for restoring sinus rhythm in chronic atrial fibrillation after failure of external cardioversion," *Europace*, Jul. 1999; 1(3):179-82.
Testa et al., "Rate-control or rhythm-control: where do we stand?" *Indian Pacing and Electrophysiology Journal*, Oct. 2005; 5(4):296-304.
Thejus et al., "N-terminal Pro-Brain Natriuretic Peptide And Atrial Fibrillation," *Indian Pacing and Electrophysiology Journal*, Jan. 2009; 9(1):1-4.
Thornton et al., "Magnetic Assisted Navigation in Electrophysiology and Cardiac Resynchronisation: A Review," *Indian Pacing and Electrophysiology Journal*, Oct. 2006; 6(4):202-13.
Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.
Tomaske et al., "Do daily threshold trend fluctuations of epicardial leads correlate with pacing and sensing characteristics in paediatric patients?" *Europace*, Aug. 2007; 9(8):662-668.
Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.
Tournoux et al., "A 'Regularly Irregular' tachycardia: What is the diagnosis?" *Europace*, Dec. 2008; 10(12):1445-6.
Traykov et al., "Electrogram analysis at the His bundle region and the proximal coronary sinus as a tool to predict left atrial origin of focal atrial tachycardias," *Europace*, Jul. 2011; 13(7):1022-7.
Trudel et al., "Simulation of QRST integral maps with a membrane-based computer heart model employing parallel processing," *IEEE Trans Biomed Eng.*, Aug. 2004; 51(8):1319-29.
Tse et al., "Cardiac dynamics: Alternans and arrhythmogenesis," *Journal of Arrhythmia*, Oct. 2016; 32(5):411-417.
Tse, "Mechanisms of cardiac arrhythmias," *Journal of Arrhythmia*, Apr. 2016; 32(2):75-81.
Ueda et al., "Outcomes of single- or dual-chamber implantable cardioverter defibrillator systems in Japanese patients," *Journal of Arrhythmia*, Apr. 2016; 32(2):89-94.
Van Dam et al., "Volume conductor effects involved in the genesis of the P wave," *Europace*, Sep. 2005; 7 Suppl 2:30-8.
Van den Berg et al., "Depletion of atrial natriuretic peptide during longstanding atrial fibrillation," *Europace*, Sep. 2004; 6(5):433-7.
Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.
Van Opstal et al., "Paradoxical increase of stimulus to atrium interval despite His- bundle capture during para-Hisian pacing," *Europace*, Dec. 2009; 11(12):1702-4.
Veenhuyzen et al., "Diagnostic pacing maneuvers for supraventricular tachycardia: part 1," *Pacing Clin Electrophysiol.*, Jun. 2011; 34(6):767-82.
Veenhuyzen et al., "Diagnostic pacing maneuvers for supraventricular tachycardias: part 2," *Pacing Clin Electrophysiol.*, Jun. 2012; 35(6):757-69.
Veenhuyzen et al., "Principles of Entrainment: Diagnostic Utility for Supraventricular Tachycardia," *Indian Pacing and Electrophysiology Journal*, 2008; 8(1):51-65.
Verbrugge et al., "Revisiting diastolic filling time as mechanistic insight for response to cardiac resynchronization therapy," *Europace*, Dec. 2013; 15(12):1747-56.
Verrier et al., "Mechanisms of ranolazine's dual protection against atrial and ventricular fibrillation," *Europace*, Mar. 2013; 15(3):317-324.
Verrijcken et al., "Pacemaker-mediated tachycardia with varying cycle length: what is the mechanism?" *Europace*, Oct. 2009; 11(10):1400-2.
Villani et al., "Reproducibility of internal atrial defibrillation threshold in paroxysmal and persistent atrial fibrillation," *Europace*, Jul. 2004; 6(4):267-72.
Violi et al., "Antioxidants for prevention of atrial fibrillation: a potentially useful future therapeutic approach? A review of the literature and meta-analysis," *Europace*, Aug. 2014; 16(8):1107-1116.
Weber et al., "Adenosine sensitive focal atrial tachycardia originating from the non- coronary aortic cusp," *Europace*, Jun. 2009; 11(6):823-6.
Weber et al., "Open-irrigated laser catheter ablation: relationship between the level of energy, myocardial thickness, and collateral damages in a dog model," *Europace*, Jan. 2014; 16(1):142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," *IEEE Trans Biomed Eng.*, Apr. 1995; 42(4):343-57.
Weijs et al., "Clinical and echocardiographic correlates of intra-atrial conduction delay," *Europace*, Dec. 2011; 13(12):1681-7.

(56) References Cited

OTHER PUBLICATIONS

Weiss et al., "The influence of fibre orientation, extracted from different segments of the human left ventricle, on the activation and repolarization sequence: a simulation study," *Europace*, Nov. 2007; 9(Suppl. 6):vi96-vi104.
Wetzel et al., "A stepwise mapping approach for localization and ablation of ectopic right, left, and septal atrial foci using electroanatomic mapping," *European Heart Journal*, Sep. 2002; 23(17):1387-1393.
Wlodarska et al., "Thromboembolic complications in patients with arrhythmogenic right ventricular dysplasia/cardiomyopathy," *Europace*, Aug. 2006; 8(8):596-600.
Wong et al., "A review of mitral isthmus ablation," *Indian Pacing and Electrophysiology Journal*, 2012; 12(4):152-170.
Wu et al., "Acute and long-term outcome after catheter ablation of supraventricular tachycardia in patients after the Mustard or Senning operation for D-transposition of the great arteries," *Europace*, Jun. 2013; 15(6):886-91.
Xia et al., "Asymmetric dimethylarginine concentration and early recurrence of atrial fibrillation after electrical cardioversion," *Pacing Clin Electrophysiol.*, Aug. 2008; 31(8):1036-40.
Yamazaki et al., "Acute Regional Left Atrial Ischemia Causes Acceleration of Atrial Drivers during Atrial Fibrillation," *Heart Rhythm*, Jun. 2013; 10(6):901-9.
Yang et al., "Focal atrial tachycardia originating from the distal portion of the left atrial appendage: Characteristics and long-term outcomes of radiofrequency ablation," *Europace*, Feb. 2012; 14(2):254-60.
Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.
Yoon et al., "Measurement of thoracic current flow in pigs for the study of defibrillation and cardioversion," *IEEE Transactions on Biomedical Engineering*, Oct. 2003; 50(10):1167-1773.
Yuan et al., "Recording monophasic action potentials using a platinum-electrode ablation catheter," *Europace*, Oct. 2000; 2(4):312-9.
Yusuf et al., "5-Hydroxytryptamine and Atrial Fibrillation: How Significant is This Piece in the Puzzle?" *J Cardiovasc Electrophysiol.*, Feb. 2003; 14(2):209-14.
Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.
Zhang et al., "Acute atrial arrhythmogenicity and altered Ca(2+) homeostasis in murine RyR2-P2328S hearts," *Cardiovascular Research*, Mar. 2011; 89(4):794-804.
Zoghi et al., "Electrical stunning and hibernation: suggestion of new terms for short- and long-term cardiac memory," *Europace*, Sep. 2004; 6(5):418-24.
Zografos et al., "Inhibition of the renin-angiotensin system for prevention of atrial fibrillation," *Pacing Clin Electrophysiol.*, Oct. 2010; 33(10):1270-85.
(PCT/US2014/066792) PCT Notification of Transmittal of the International Search Report and the Written Opinion of the International Searching Authority.
(PCT/US2014/013601) PCT Notification of Transmittal of the International Search Report and the Written Opinion of the International Searching Authority.
(PCT/US2014/036782) PCT Notification of Transmittal of the International Search Report and the Written Opinion of the International Searching Authority, Mailed Aug. 22, 2014, 11 pages.
International Search Report and Written Opinion for Application No. PCT/US2017/047378, 8 pages, date mailed Dec. 6, 2017.
(PCT/US2018/050988) PCT Notification of Transmittal of the International Search Report and the Written Opinion of the International Searching Authority, Mailed Nov. 14, 2018, 11 pages.
(PCT/US2018/050993) PCT Notification of Transmittal of the International Search Report and the Written Opinion of the International Searching Authority, mailed Nov. 16, 2018, 7 pages.
(PCT/US2019/023642) PCT Notification of Transmittal of the International Search Report and the Written Opinion of the International Searching Authority, mailed Jun. 28, 2019, 14 pages.
(PCT/US2019/023645) PCT Notification of Transmittal of the International Search Report and the Written Opinion of the International Searching Authority, mailed Sep. 4, 2019, 14 pages.
(PCT/US2019/023646) PCT Notification of Transmittal of the International Search Report and the Written Opinion of the International Searching Authority, mailed Aug. 19, 2019, 15 pages.
(PCT/IB2019/057352) PCT Notification of Transmittal of the International Search Report and the Written Opinion of the International Searching Authority, mailed Nov. 27, 2019, 123 pages.
International Search Report and Written Opinion for Application No. PCT/US2020/023525, 10 pages, date mailed Jul. 9, 2020.
International Search Report and Written Opinion for PCT/US2020/062466 dated Jan. 27, 2021 (11 pages).

* cited by examiner

IMPLANTABLE MEDICAL DEVICES FOR MULTI-CHAMBER PACING

This application is a divisional of U.S. patent application Ser. No. 17/105,603 filed Nov. 26, 2020, which claims the benefit of U.S. Provisional Patent Application Ser. No. 62/940,711 entitled "Implantable Medical Devices For Multi-Chamber Pacing" filed on Nov. 26, 2019, which are is incorporated herein by reference in their entirety.

The present technology is generally related to implantable medical devices and, in particular, leadless implantable medical devices and related uses.

SUMMARY

In one illustrative implantable medical device, the device includes a plurality of electrodes. The plurality of electrodes may include a right atrial electrode positionable within the right atrium to deliver cardiac therapy to or sense electrical activity of the right atrium of the patient's heart and at least one left ventricular electrode positionable proximate the left ventricle of the patient's heart. The device may further include a housing extending from a proximal end region to a distal end region and the right atrial electrode may be leadlessly coupled to the proximal end region. The device may further include a leadlet extending from a proximal region to a distal region, where the proximal region is coupled to the distal end region of the housing and the at least one ventricular electrode is coupled to the distal region of the leadlet. Further, the leadlet may be configured to extend through the coronary sinus ostium and into the coronary sinus or a coronary vein of the patient's heart to position the least one left ventricular electrode proximate the left ventricle of the patient's heart. The device may further include a therapy delivery circuit within the housing and operably coupled to the plurality of electrodes to deliver cardiac therapy to the patient's heart and a sensing circuit within the housing and operably coupled to the plurality of electrodes to sense electrical activity of the patient's heart. The device may further include a controller within the housing and comprising processing circuitry operably coupled to the therapy delivery circuit and the sensing circuit. The controller may be configured to monitor electrical activity using the processing circuitry and one or more of the plurality of electrodes and delivering pacing therapy using the processing circuitry and one or more of the plurality of electrodes.

In one illustrative method, the method may include implanting a right atrial electrode in the right atrial endocardium or in the right atrial myocardium of a patient's heart, the right atrial electrode being leadlessly coupled to a proximal end region of an implantable housing. The method may further include implanting at least one left ventricular electrode through the coronary sinus ostium and into the coronary sinus or a coronary vein of the patient's heart, where the at least one left ventricular electrode being coupled to a distal region of a leadlet and a proximal region of the leadlet being coupled to a distal end region of the implantable housing. Processing circuitry may be located, positioned, or disposed, in the housing and operably coupled to the right atrial electrode and the at least one left ventricular electrode. The method may further include monitoring electrical activity using the processing circuitry and one or more of the right atrial electrode and the at least one left ventricular electrode and delivering pacing therapy using the processing circuitry and at one or more of the right atrial electrode and the at least one left ventricular electrode.

In one illustrative method, the method may include delivering a delivery catheter and a penetration element located, positioned, or disposed, in the delivery catheter to the right ventricular endocardium of the interventricular septal wall of a patient's heart, puncturing the right ventricular endocardium using the penetration element to form an opening through the right ventricular endocardium and into the interventricular septal wall, and retracting the penetration element. The method may further include advancing a distal portion of a guide element through the delivery catheter and the opening and into the interventricular septal wall to extend along the left ventricular endocardial wall and delivering a distal portion of an implantable medical lead over the guide element to the left ventricular myocardium to extend along the left ventricular endocardial wall to position at least one left ventricular electrode on the distal portion in the left ventricular myocardium.

In one illustrative system for delivering an implantable medical lead into the interventricular septal wall and proximate the left ventricular myocardium, the system may include a delivery catheter extending from a proximal end region to a distal end region, where the distal end region positionable adjacent to the right ventricular endocardium of the interventricular septal wall of a patient's heart. The system may further include a penetration element locatable, positionable, or disposable, in the delivery catheter to form an opening through the right ventricular endocardium and into the interventricular septal wall and a guide element extending from a proximal end region to a distal end region. The guide element may be locatable, positionable, or disposable, in the delivery catheter to enter the interventricular septal wall through the opening and to extend along the left ventricular endocardial wall.

The above summary is not intended to describe each embodiment or every implementation of the present disclosure. A more complete understanding will become apparent and appreciated by referring to the following detailed description and claims taken in conjunction with the accompanying drawings. In other words, these and various other features and advantages will be apparent from a reading of the following detailed description.

DETAILED DESCRIPTION

The present disclosure makes reference to a leadless implantable medical device (LIMD). Examples LIMDs having a leadlet that may be used are described in U.S. Pat. No. 10,463,853, granted Nov. 5, 2019, which is incorporated by reference in its entirety.

The present disclosure also makes reference to the triangle of Koch region. Examples of uses of the triangle of Koch region are described U.S. Patent Application Publication No. 2019/0290905 published on Sep. 26, 2019, which is incorporated by reference in its entirety.

In general, any suitable type of IMD (or LIMD) including a lead or leadlet may be used. Non-limiting examples of suitable IMDs include an implantable transvenous pacemaker, a transvenous cardiac resynchronization therapy (CRT) device, a transvenous CRT pacemaker (CRT-P), a transvenous CRT defibrillator (CRT-D), an implantable transvenous cardioverter defibrillator (ICD), a subcutaneous ICD (S-ICD), and a subcutaneous medical device.

Figure 1:
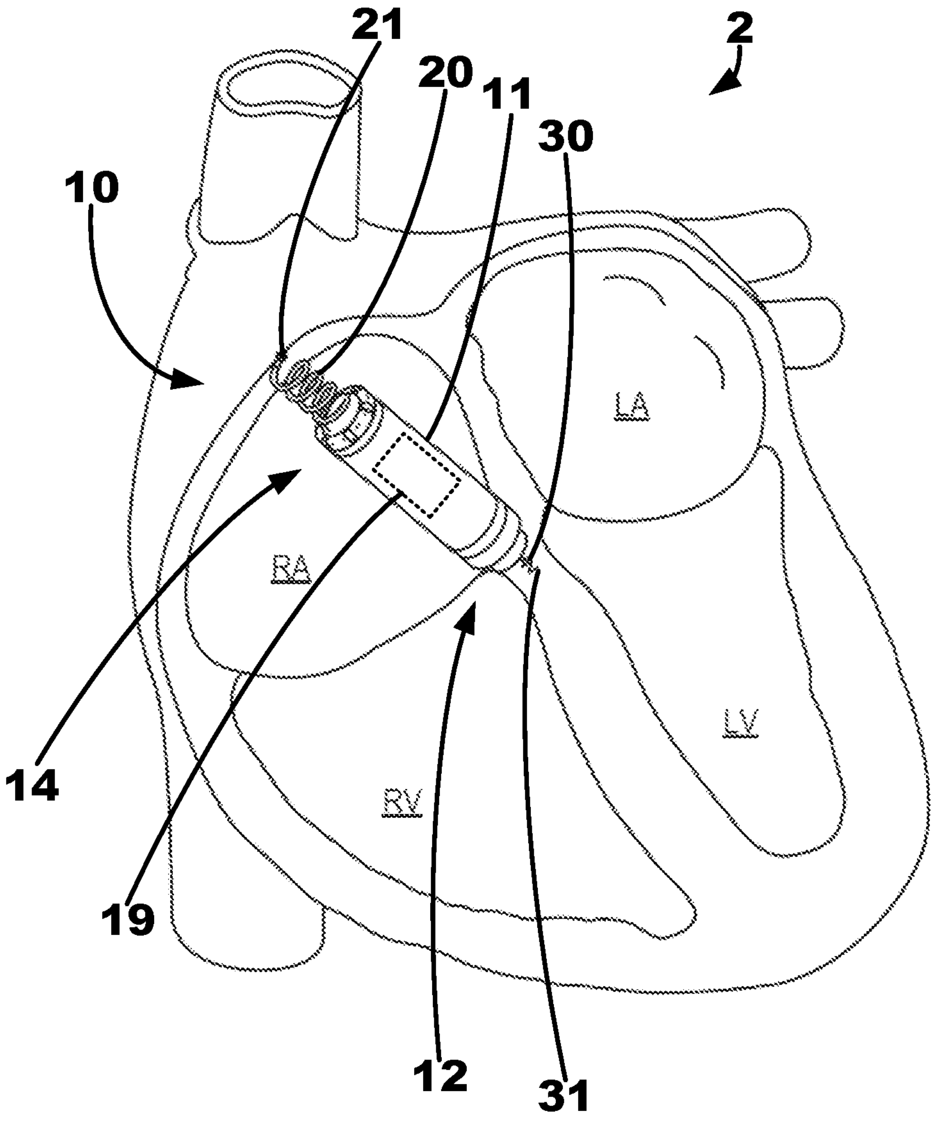
FIG. 1 is a conceptual diagram of one example of a leadless implantable medical device (LIMD) positioned in the right atrium (RA) of a patient's heart including a leadlet positioned in the RA of the patient's heart.

One example of a LIMD 10 positioned in the right atrium (RA) of a patient's heart 2 including a leadlet 20 positioned in the RA of the patient's heart 2 is depicted in FIG. 1. The LIMD 10 may include a housing 11 extending from a distal end region 12 to a proximal end region 14. The leadlet 20 may be physically and operably coupled to the proximal end region 14 of the housing 11 of LIMD 10.

The LIMD 10 may be used to sense electrical activity of the patient's heart or to deliver cardiac therapy to the patient's heart. In general, a first electrode 21 operably and physically coupled to the leadlet 20 may be implanted in the RA endocardium or myocardium. And, a second electrode 31 may be operably and physically coupled to a fixation element 30 extending from the distal end region 12 of the LIMD 10 and may be implanted in the left ventricular (LV) myocardium. More specifically, the second electrode 31 may be coupled to a distal end region 12 of an implantable housing 11 of the LIMD 10, such as disposed on a fixation element 30 (e.g., helical or screw-like structure) extending away from the housing 11 of the LIMD 10 to facilitate fixation. The first electrode 21 may be coupled to a leadlet 20 extending from a proximal end region 14 of the housing 11 of the LIMD 10. The LIMD 10 may be described as a ventricular LIMD implanted in the atrium that paces the ventricle that also includes a leadlet, or "pig tail," that paces the atrium.

The LIMD 10 may be used in any suitable manner. In some embodiments, a method of using the LIMD 10 may include implanting the first, or right atrial, electrode 21 on the right atrial endocardium or in the right atrial myocardium of the patient's heart 2. It may be described that the leadlet 20 extends from a distal end, or first portion, to a proximal end, or second portion. The first, or right atrial, electrode 21 may be coupled to the distal end, or first portion, of the leadlet 20. The proximal end, or second portion, of the leadlet 20 may be coupled to the proximal end region 14 of the housing 11 of the LIMD 10. Processing circuitry 19 may be disposed in the housing 11 and operably coupled to the electrodes 21, 31.

An illustrative method may include implanting a left ventricular electrode through or proximate to the triangle of Koch region of the right atrium, such as in the coronary sinus (CS) ostium, through the right atrial endocardium, and through central fibrous body and into the basal, septal, or basal-septal region in the left ventricular myocardium of the patient's heart. The left ventricular electrode may be leadlessly coupled to a distal portion of the implantable housing. The processing circuitry may be operably coupled to the left ventricular electrode. The method may further include monitoring electrical activity using the processing circuitry and at least one of the right atrial electrode and the left ventricular electrode. Further, the method may include delivering pacing therapy using the processing circuitry and at least one of the right atrial electrode and the left ventricular electrode.

In another embodiment, an LIMD similar to the LIMD 10 of FIG. 1 may be utilized in a different configuration or method. For example, the LIMD may include a right atrial electrode for implantation on the right atrial endocardium or in the right atrial myocardium of the patient's heart, and the right atrial electrode may be leadlessly coupled to a distal end region, or distal portion, of an implantable housing of the LIMD. Further, a left ventricular electrode may be implanted through or proximate to the triangle of Koch region of the right atrium, such as in the CS ostium, through the right atrial endocardium, and through central fibrous body and into the basal, septal, or basal-septal region in the left ventricular myocardium of the patient's heart. The left ventricular electrode may be coupled to a distal end region, or a first portion, of a leadlet. A proximal end region, or a second portion, of the leadlet may be coupled to a proximal end region, or proximal portion, of the implantable housing of the LIMD. The processing circuitry located in the housing may be operably coupled to both of the right and the left ventricular electrode. The LIMD may monitor electrical activity using the processing circuitry and at least one of the right atrial electrode and the left ventricular electrode. Further, the LIMD may deliver pacing therapy using the processing circuitry and at least one of the right atrial electrode and the left ventricular electrode.

Figures 2A, 2B:
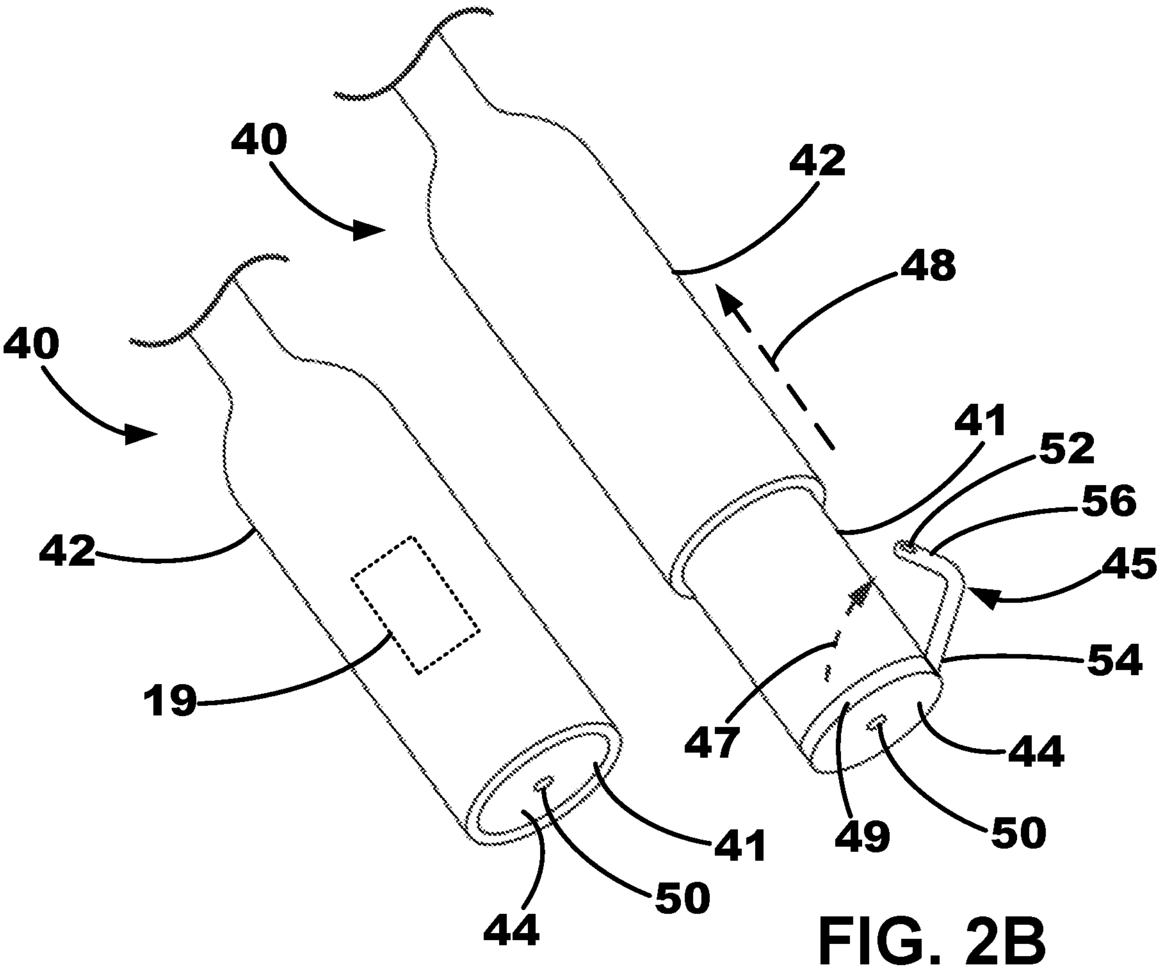
FIGS. 2A-2B depicts examples of a LIMD including a deployable leadlet.

An illustrative LIMD 40 including a deployable leadlet is depicted in FIGS. 2A-2B. The LIMD 40 may include one or more fixation elements (although not shown), a deployable leadlet 45, a first electrode 50, and a second electrode 52 coupled to the leadlet 45. The leadlet 45 extends from a proximal end region 54 to a distal end region 56, and the second electrode is located proximate (or within) the distal end region 56.

The LIMD 40 may include a body portion 41 and a sheath portion 42 moveable with respect to the body portion 41. The sheath portion 42 may define an opening or aperture within which the body portion 41 is located. The LIMD 40 may define a stowed configuration or position as shown in FIG. 2A and a deployed configuration as shown in FIG. 2B. When in the stowed configuration, the body portion 41 may be located substantially completely within the opening of the sheath portion 42 such that, e.g., the deployable leadlet 45 is also in a stowed configuration where the leadlet 45 does not extend beyond or outside of the sheath portion 42. More specifically, when in the stowed configuration, the leadlet 45 may reside within a recess, or groove, 49. The leadlet 45 may include (e.g., be formed of) resilient materials such that, e.g., when the sheath portion 42 is retracted 48 away exposed a distal end region 44 of the body portion 41, the leadlet 45 may move 47 away from (e.g., pivot or partially rotate away from) the body portion 41 in at least partially radial manner to position the distal end region 56, and consequently, the second electrode 52, of the leadlet 45, away from the body portion 41.

Although not shown in FIGS. 2A-2B, one or more fixation elements may be disposed on the distal end region 44 of the body portion 41 of the LIMD 40 and extend distally from the body portion 41. The one or more fixation elements may be electrically active or passive. The first electrode 50 may be positioned on the distal end region 44 of the body portion 41 of the LIMD 40 to engage the endocardial wall of the patient's heart. The second electrode 52 may be coupled to the leadlet 45 extending at least partially in a radial direction away from the body portion 41 in a deployed position. As described herein, the body portion 41 may define, or include, a recess 49 to at least partially receive the leadlet 45 in the stowed position. In other words, it may be described that the body portion 41 may be delivered in a "cup" (e.g., defined by the sheath portion 42) and protracted to deploy the body portion 41 for implantation. In some embodiments, the endocardial wall is the right atrial endocardial wall. Additionally, as can be seen in FIG. 2B, the leadlet 45 may described as defining a shape have two sections or portions. The first section, which is closest to the proximal end region 54, may extend tangentially and in a straight line away from the outside (e.g., circumference) of the body portion 41. The second section, which is closer to the distal end region 56, may then curve or bend away from the tangentially straight line defined by the first section back towards a path somewhat or partially parallel to the outside (e.g., circumference) of the body portion 41.

Figure 3A:
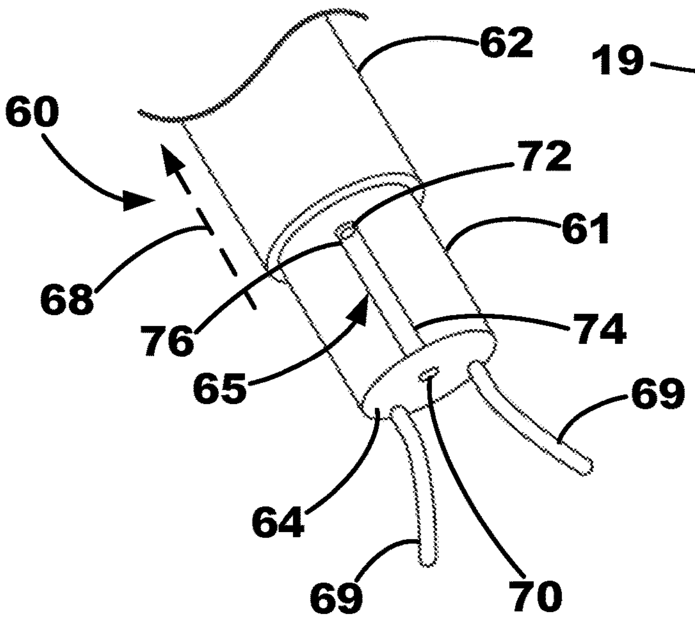
FIGS. 3A-3C depicts examples of a LIMD including a deployable leadlet.
Figure 3B:
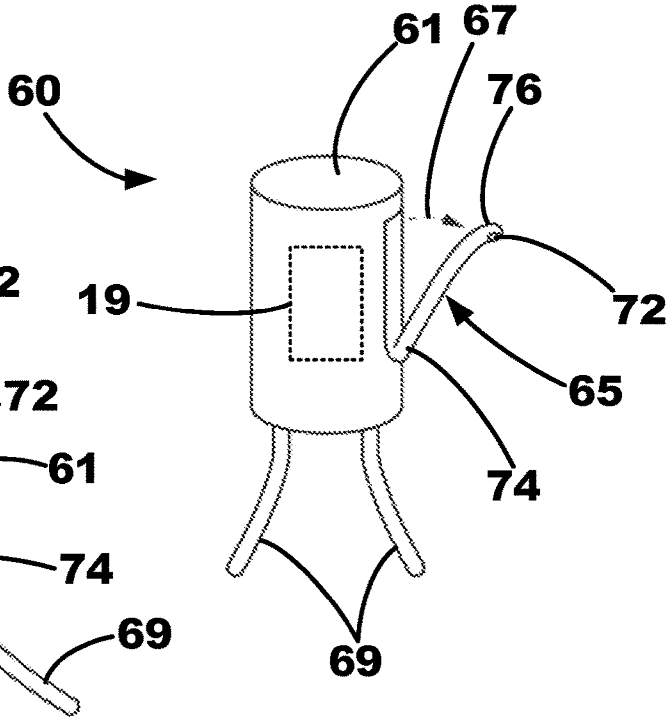

An illustrative LIMD 60 including a deployable leadlet 65 is depicted in FIGS. 3A-3B. The LIMD 60 may include one or more fixation elements 69 (e.g., curved tines), a deployable leadlet 65, a first electrode 70, and a second electrode 72 coupled to the leadlet 65. The leadlet 65 extends from a proximal end region 74 to a distal end region 76, and the second electrode 72 is located proximate (or within) the distal end region 76.

The LIMD 60 may include a body portion 61 and a sheath portion 62 moveable with respect to the body portion 61. The sheath portion 62 may define an opening or aperture within which the body portion 61 is located. The LIMD 60 may define a stowed configuration or position when the body portion 61 is substantially completely within the opening of the sheath portion 62 such that, e.g., the deployable leadlet 65 is also in a stowed configuration or position where the leadlet 65 does not extend beyond or outside of the sheath portion 62. The LIMD 60 may further define a deployed configuration as shown in FIGS. 3A-3B. More specifically, when in the stowed configuration, the leadlet 65 may reside within a recess or groove. The leadlet 65 may include (e.g., be formed of) resilient materials such that, e.g., when the sheath portion 62 is retracted 68 away exposed a distal end region 64 of the body portion 61, the leadlet 65 may move 67 (e.g., pivot or partially rotate) away from the body portion 61 in at least partially radial manner to position the distal end region 76, and consequently, the second electrode 72, of the leadlet 65, away from the body portion 61.

One or more fixation elements 69 may be disposed on the distal end region 64 of the body portion 61 of the LIMD 60 and extend distally from the body portion 61. The one or more fixation elements 69 may be electrically active or passive. The first electrode 70 may be positioned on the distal end region 64 of the body portion 61 of the LIMD 40 to engage the endocardial wall of the patient's heart. The second electrode 72 may be coupled to the leadlet 65 extending at least partially in a radial direction away from the body portion 61 in a deployed position as shown. As described herein, the body portion 61 may define, or include, a recess to at least partially receive the leadlet 65 in the stowed position. In other words, it may be described that the body portion 61 may be delivered in a "cup" (e.g., defined by the sheath portion 62) and protracted to deploy the body portion 61 for implantation. In some embodiments, the endocardial wall is the right atrial endocardial wall.

Figure 3C:
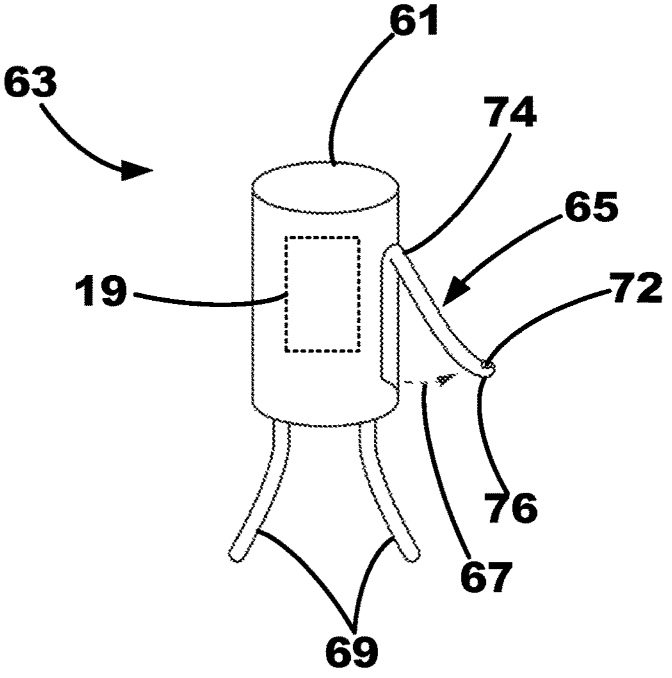

Another illustrative LIMD 63 including a deployable leadlet 65 is depicted in FIG. 3C. The LIMD 63 may be substantially similar to the LIMD 60 except for the movement of the leadlet 65. As shown, the leadlet 65 of LIMD 63 swings, or rotates, away from the body portion 61 in an opposite direction than the leadlet 65 of LIMD 60 to, e.g., provide ease of re-sheathing the body portion 61 into the sheath portion 62. More specifically, the sheath portion 62 may contact and "fold down" the leadlet 65 when the body portion 61 is moved with respect to the sheath portion 62 of the LIMD 63 to position the body portion 61 within the aperture or opening of the sheath portion 62 (i.e., the body portion 61 being retracted into the sheath portion 62). In other words, the LIMD 63 may be provide "easy" retraction of the body portion 61 within the sheath portion 62.

The LIMDs 40, 60, 63 may be used in any suitable manner. In some embodiments, a method of using the LIMDs 40, 60, 63 may include attaching one or more fixation elements 69 thereof to the endocardial wall of the patient's heart. The fixation elements 69 may be coupled to the distal end region, or distal portion, 44, 64 of the body portion 41, 61. Processing circuitry 19 may be disposed in the body portion 41, 61. The method of using the LIMDs 40, 60, 63 may also include implanting the first electrode 50, 70 to engage the endocardial wall of the patient's heart when the fixation element is attached. The first electrode 50, 70 may be leadlessly coupled to the distal end region, or distal portion, 44, 64 of the body portion 41, 61. The processing circuitry 19 may be operably coupled to each of the first and second electrodes 50, 52, 70, 72.

The method of using the LIMDs 40, 60, 63 may further include implanting the second electrode 52, 72 to engage the endocardial wall of the patient's heart when the LIMD 40, 60, 63 is in the deployed configuration placing the leadlet 45, 65 in the deployed position. More specifically, it may be described that the second electrode 52, 72 is coupled to the distal end region, or a first portion, 56, 76 of the leadlet 45, 65 and the proximal end region, or a second portion, 54, 74 of the leadlet 45, 65 may be coupled to the distal end region 44, 64 of the body portion 41, 61. As described herein, the leadlet 45, 65 may extend at least partially in a radial direction away from the body portion 41, 61 in the deployed configuration/position so as to, e.g., engage cardiac tissue with the second electrode 52, 72.

The method of using the LIMDs 40, 60, 63 may further include monitoring electrical activity using the processing circuitry 19 and at least one of the first electrode 50, 70 and the second electrode 52, 72. Further, the method of using the LIMDs 40, 60, 63 may further include delivering pacing therapy using the processing circuitry 19 and at least one of the first electrode 50, 70 and the second electrode 52, 72.

Although no fixation element is depicted on the LIMD 40 in FIGS. 2A-2B and tines 69 are depicted on the LIMD 60 of FIGS. 3A-3C, it is to be understood that any suitable fixation element may be used. In some embodiments, the fixation elements may include one or more helix structures or screw-like structures. In some embodiments, the fixation elements may include one or more adhesives (which may be used in conjunction with other fixation elements such as a helix structure).

Figure 4:
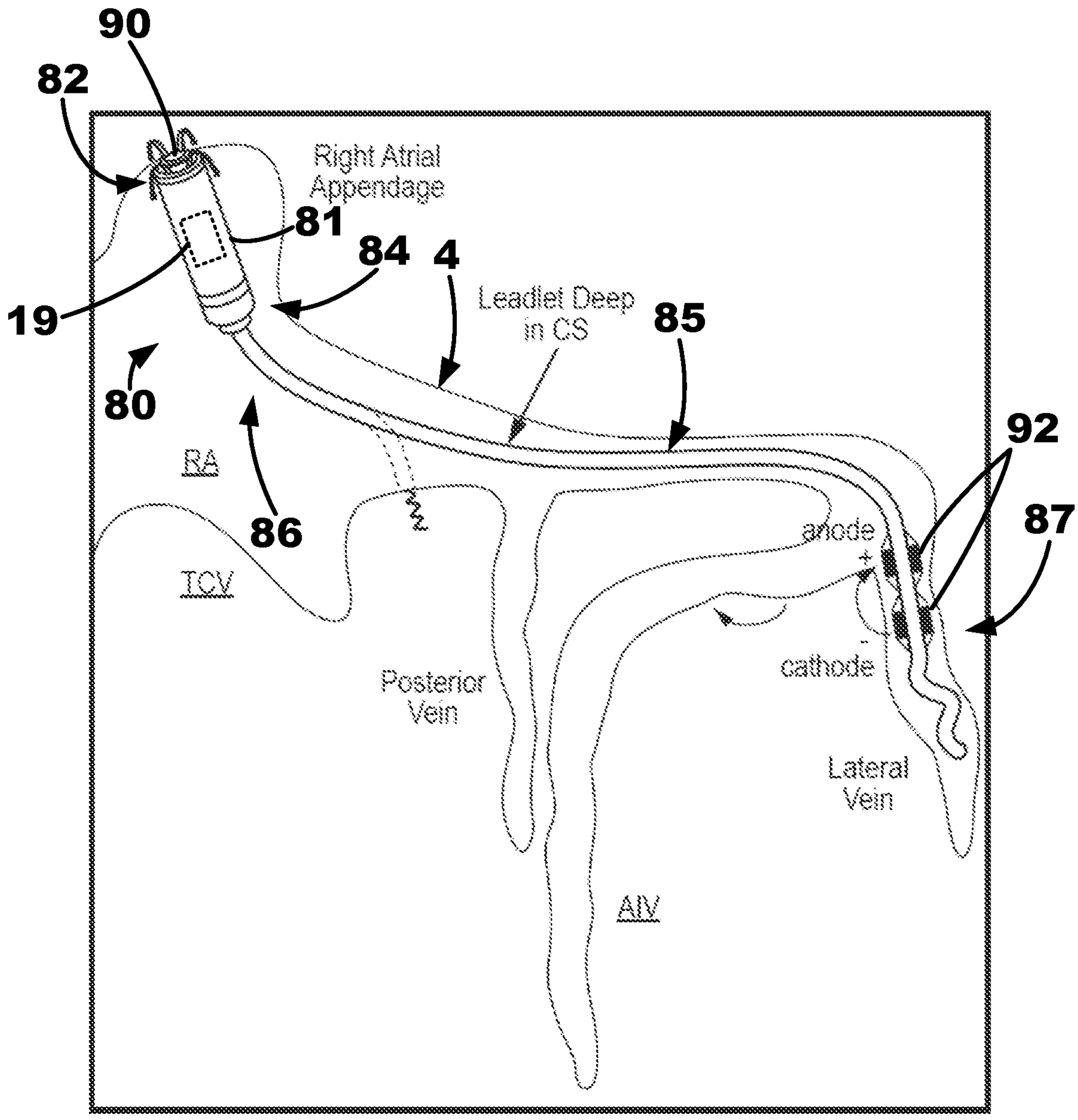
FIG. 4 is a conceptual diagram of an LIMD positioned in the RA of a patient's heart including a leadlet extending through the coronary sinus (CS) ostium of the patient's heart.

A conceptual diagram of an LIMD 80 positioned in the right atrium of a patient's heart including a leadlet 85 extending through the coronary sinus (CS) ostium of the patient's heart is depicted in FIG. 4. The LIMD 80 may include an implantable housing 81 extending from a proximal end region 82 to a distal end region 84. The LIMD 80 may include a plurality of electrodes. The plurality of electrodes may include one or more right atrial electrodes configured to sense and/or pace right atrial tissue and one or more left ventricular electrodes configured to sense and/or pace left ventricular tissue. For example, as shown, the LIMD 80 includes a right atrial electrode 90 positioned on the proximal end region 82 of the implantable housing 81 of the LIMD 80. The right atrial electrode 90 may be implanted in the right atrial endocardium or in the right atrial myocardium of the patient's heart. In some embodiments, the right atrial electrode 90 may be positioned proximate to (e.g., in contact with, adjacent, partially within, within, etc.) the right atrial appendage.

The LIMD 80 in FIG. 4 also includes a pair of left ventricular electrodes 92 coupled to the leadlet 85 extending distally from the housing 81. The leadlet 85 may be described as extending from a proximal region 86 to a distal region 87. The proximal region 86 is coupled to the distal end region 84 of the housing 81. The electrodes 92 are positioned on or proximate the distal region 87 of the leadlet 85. When implanted, the leadlet 85 may extend through the coronary sinus ostium and into the coronary sinus or a coronary vein of the patient's heart to position the left ventricular electrodes 92 proximate the left ventricle of the patient's heart. Thus, in some embodiments, the left ventricular electrodes 92 may be implanted in the coronary sinus or a coronary vein, and in other embodiments, the left ventricular electrodes may be implanted in the left ventricular myocardium of the patient's heart, for example, using a helical structure or screw-like structure. In the embodiment depicted in FIG. 4, it may be described that a plurality of left ventricular electrodes 92 are coupled to the leadlet 85, for example, including an anode and a cathode. In some embodiments, the plurality of left ventricular electrodes 92 may be used for field steering, for example, to avoid capture of the left atrium (LA) of the patient's heart.

The LIMD 80 may be described as being implanted in the atrium to sense or pace the atrium. The leadlet 85, which may be advanced a relatively long way down the coronary sinus, anterior interventricular vein (AIV) or great cardiac vein (GCV), or lateral vein, to pace the left ventricle or may be advanced a short way into the coronary sinus and then fixated "down" into left ventricular myocardium to pace the left ventricle. In some embodiments, the leadlets described herein may be quadripolar leadlets including four electrodes. Further, any of the leadlets described herein may also use active fixation, which may allow for adjustment of electrode depth, for example, into the left ventricular myocardium.

The LIMD 80 of FIG. 4 may be used in any suitable manner. In some embodiments, a method of using the LIMD 80 may include implanting the right atrial electrode 90 on the right atrial endocardium or in the right atrial myocardium of the patient's heart. The right atrial electrode 90 may be leadlessly coupled to a proximal end region, or portion, 82 of the implantable housing 81. Processing circuitry 19 may be disposed in the housing 81 and may be operably coupled to the right atrial electrode 90.

The method of using the LIMD 80 may also include implanting the left ventricular electrodes 92 through the coronary sinus ostium and into the coronary sinus or a coronary vein of the patient's heart. The left ventricular electrodes 92 may be coupled to the distal region, or first portion, 87 of the leadlet 85. The proximal region, or second portion, 86 of the leadlet 85 may be coupled to the distal end region 84 of the implantable housing 81. The processing circuitry 19 may also be operably coupled to the left ventricular electrodes 92.

The method of using the LIMD 80 may further include monitoring electrical activity using the processing circuitry 19 and at least one of the right atrial electrode 90 and the left ventricular electrodes 92 and may include delivering pacing therapy using the processing circuitry 19 and at least one of the right atrial electrode 90 and the left ventricular electrodes 92. In some embodiments, implanting the left ventricular electrodes 92 may include implanting the left ventricular electrodes 92 into the left ventricular myocardium from the coronary sinus proximal to the posterior vein of the patient's heart. In some embodiments, implanting the left ventricular electrodes 92 may include implanting the left ventricular electrodes 92 into the anterior interventricular vein (AIV) of the patient's heart. In some embodiments, implanting the left ventricular electrodes 92 may include implanting the left ventricular electrodes 92 into the lateral vein of the patient's heart. Further, in some embodiments, delivering pacing therapy may include utilizing field steering to avoid left atrial capture by the left ventricular electrodes 92.

Conceptual diagrams showing one example of implantation of an implantable medical device (IMD) 100 including an implantable medical lead or leadlet 150 extending through the right ventricular (RV) endocardium are depicted in FIGS. 5A-5D. Although a lead is described herein, a leadlet extending from an intracardiac implantable housing of an LIMD may also be used. In other words, the lead 150 could be either a lead extending from an IMD located, or positioned, outside of the heart or a leadlet extending from a LIMD located, or positioned, inside of the heart.

The lead 150 may extend from a proximal portion coupled to the a control portion of the IMD 100 (e.g., a housing, battery, controller, processing circuitry, etc.) to a distal portion 154 that is positioned in or proximate the left ventricular myocardium extending along the left ventricular endocardial wall 8, for example, toward the apex of the patient's heart. The distal portion 154 may be proximate to the left bundle branch (LBB) of the patient's heart. Although any suitable delivery system may be used to deliver the lead 150, a delivery system and method of implantation using such delivery system are shown and described with respect to FIGS. 5A-5D. Generally, the delivery system may be described as puncturing the right ventricular endocardium 6 to allow a lead 150 to be simply pushed into the septal myocardium 7, or interventricular septal wall, and tunneled up or down the septum. The lead 150 may be tunneled into the basal-septal, mid-septal, or even apical septal region with the septal myocardium 7.

Figure 14:
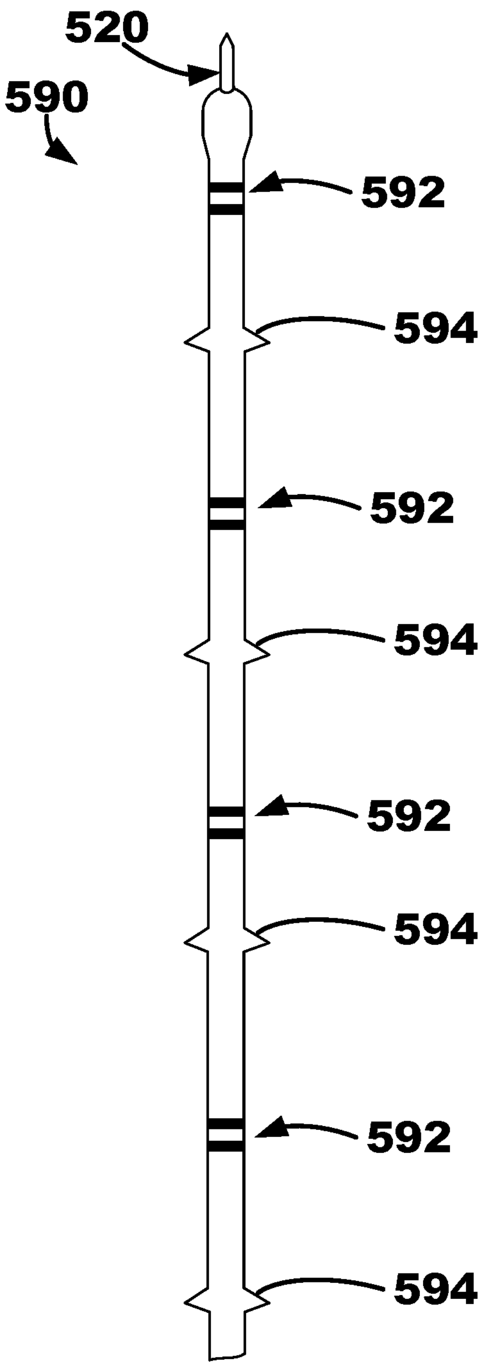
FIG. 14 depicts of an illustrative quadripolar lead.

The lead 150 may be a multipolar lead such as, e.g., the quadripolar lead 590 described herein with respect to FIG. 14. More specifically, a distal portion 154 of the lead 150 may have a quadripolar configuration, which may be the same or similar to an ATTAIN STABILITY™ or ATTAIN STABILITY QUAD™ or ATTAIN PERFORMA™ leads available from Medtronic plc of Dublin, Ireland. A side helix or hook usable for fixation that may be disposed on the distal portion, which may be selectively electrically active or passive and may be mechanically active or adjustable. Another exemplary lead that may be employed is described in U.S. Pat. No. 9,901,732 to Sommer et al., granted Feb. 27, 2018, which is incorporated by reference in its entirety, in which electrodes are jumpered in a diagonal configuration in order to increase the opportunity to capture cardiac tissue.

A guide element 130, such as a guidewire, a steerable stylet or wire, or a hybrid of stylet guidewire that is a part of the ATTAIN family, may be used to guide 130 the lead 150 into the septum 7. With multiple electrodes and different spacing, one lead 150 may be used to pace the atrium and multiple locations down the septum 7. One example of a guiding element that may be used is described in U.S. Pat. No. 7,881,806 to Sommer et al., granted Feb. 1, 2011, which is incorporated by reference in its entirety.

Figure 5A:
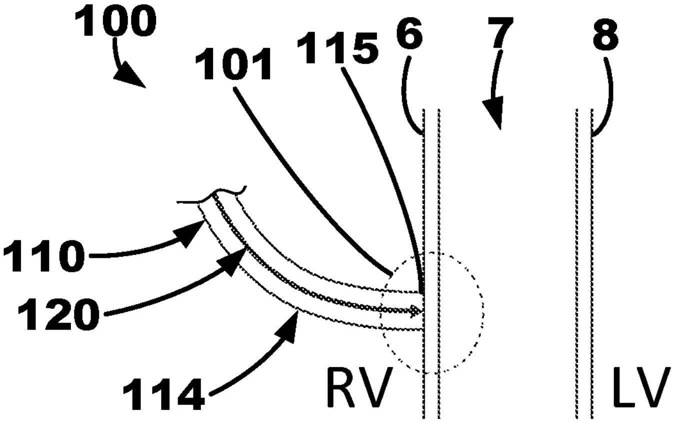
FIGS. 5A-5D are conceptual diagrams showing one example of an implantable medical device (IMD) including an implantable medical lead or leadlet extending through the right ventricular (RV) endocardium into the ventricular septum.

The IMD 100 including the lead 150 may be used in any suitable manner. In some embodiments, a method of delivering and using the IMD 100 may include delivering a delivery catheter 110 and a penetration element 120 disposed in the delivery catheter 110 to the right ventricular endocardium 6 of the interventricular septal wall of a patient's heart as shown in FIG. 5A. The delivery catheter 110 may be configured to provide positioning of the distal end 115 of the delivery catheter to target implantation location 101 such that the distal end 115 is positioned adjacent to (e.g., substantially flush or in contact with) the right ventricular endocardium 6. For example, in one embodiment, the delivery catheter 110 extends from a proximal portion to a distal portion 114, and the distal portion 114 defines a curvature to position the distal end 115 of the catheter 110 substantially flush to the right ventricular endocardium 6.

Figure 5B:
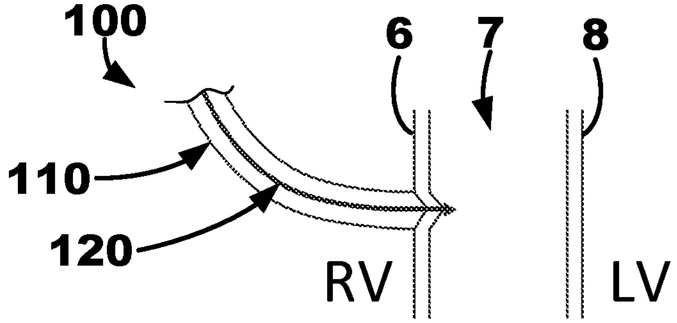
Figure 5C:
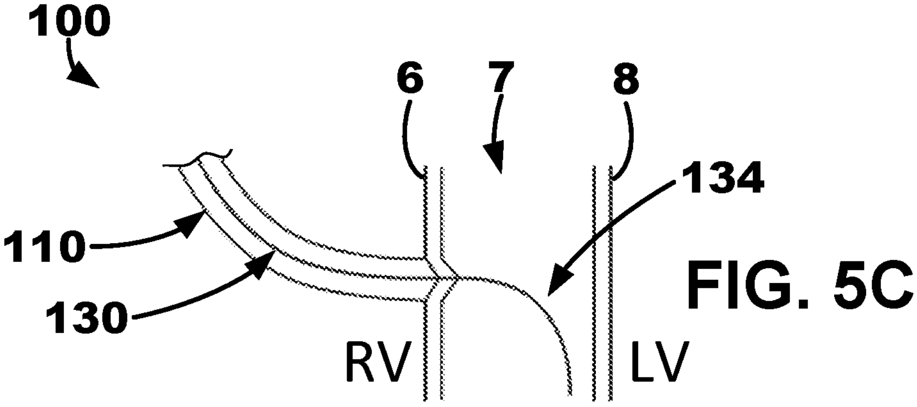
Figure 5D:
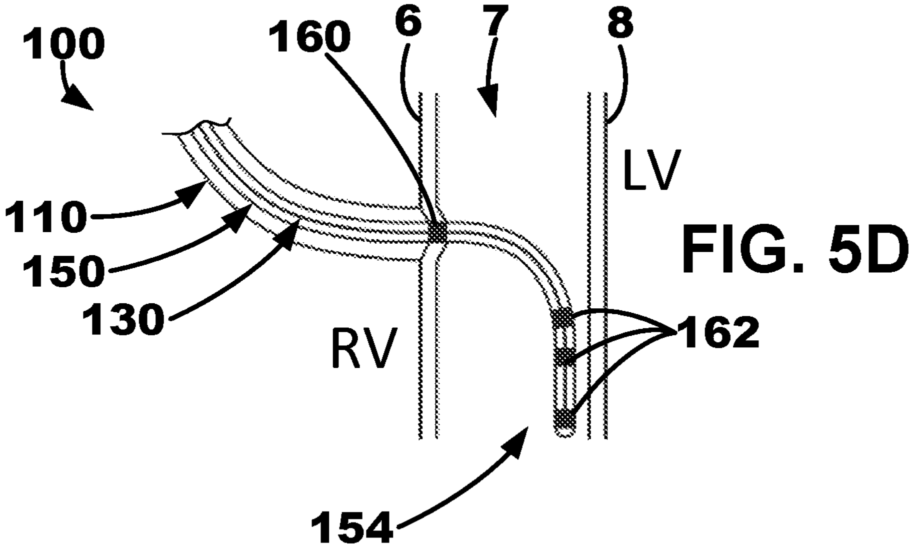

The method may include puncturing the right ventricular endocardium 6 using the penetration element 120 to form an opening through the right ventricular endocardium 6 and into the interventricular septal wall 7 as shown in FIG. 5B. The penetration element 120 may then be retracted through the delivery catheter 110. Then, a distal portion of a guide element 130 may be advanced through the delivery catheter 110 and the opening and into the interventricular septal wall 7 to extend along the left ventricular endocardial wall 8. The guide element 130 may extend from a proximal region to a distal region 134 and the distal region 134 may be configured to be positioned into the interventricular septal wall 7 to extend along the left ventricular endocardial wall 8. In at least one embodiment, the distal region 134 may define or include a distal curvature portion that curves when exiting the delivery catheter 110 into the interventricular septal wall 7 so as to deliver at least a region of a distal portion 154 of an implantable medical lead 150 substantially parallel to the interventricular septal wall 7 in the left ventricular myocardium.

In addition, a distal portion of the implantable medical lead 150 of the device 100 may be advanced or delivered over the guide element 130 to the left ventricular myocardium to extend along the left ventricular endocardial wall 8 to position one or more left ventricular electrodes 162 on the distal portion in the left ventricular myocardium. In one or more embodiments, the guide element 130 does not extend beyond the tip of the lead 150, and instead, may remain a selected distance away from the tip (e.g., about 1 centimeter) to allow tip to flex during blunt dissection/tunneling of the lead 150. Further, Examples of the guide element 130 may include a steerable stylet, shaped stylets, etc. In some embodiments, one or more left ventricular electrodes 162 may be positioned proximate to the left bundle branch (LBB) of the conduction system of the patient's heart.

In some embodiments, a right ventricular electrode 160 on the lead 150 may be positioned/implanted proximate to the right ventricular endocardium 6. The right ventricular electrode 160 may be positioned proximal to the left ventricular electrode on the distal portion 154 of the implantable medical lead 150.

Further, the method of using IMD 100 may include monitoring electrical activity of at least one of the right ventricular electrode 160 and one or more of the left ventricular electrodes 162, and delivering pacing therapy using at least one of the right ventricular electrode 160 and the left ventricular electrodes 162. In some embodiments, delivering pacing therapy may include delivering pacing pulses to the left ventricular electrodes 162 configured to pace the left bundle branch of the conduction system of the patient's heart. In some embodiments, the implantable medical lead 150 may include a plurality of left ventricular electrodes, a plurality of right ventricular electrodes, or both.

Figure 6:
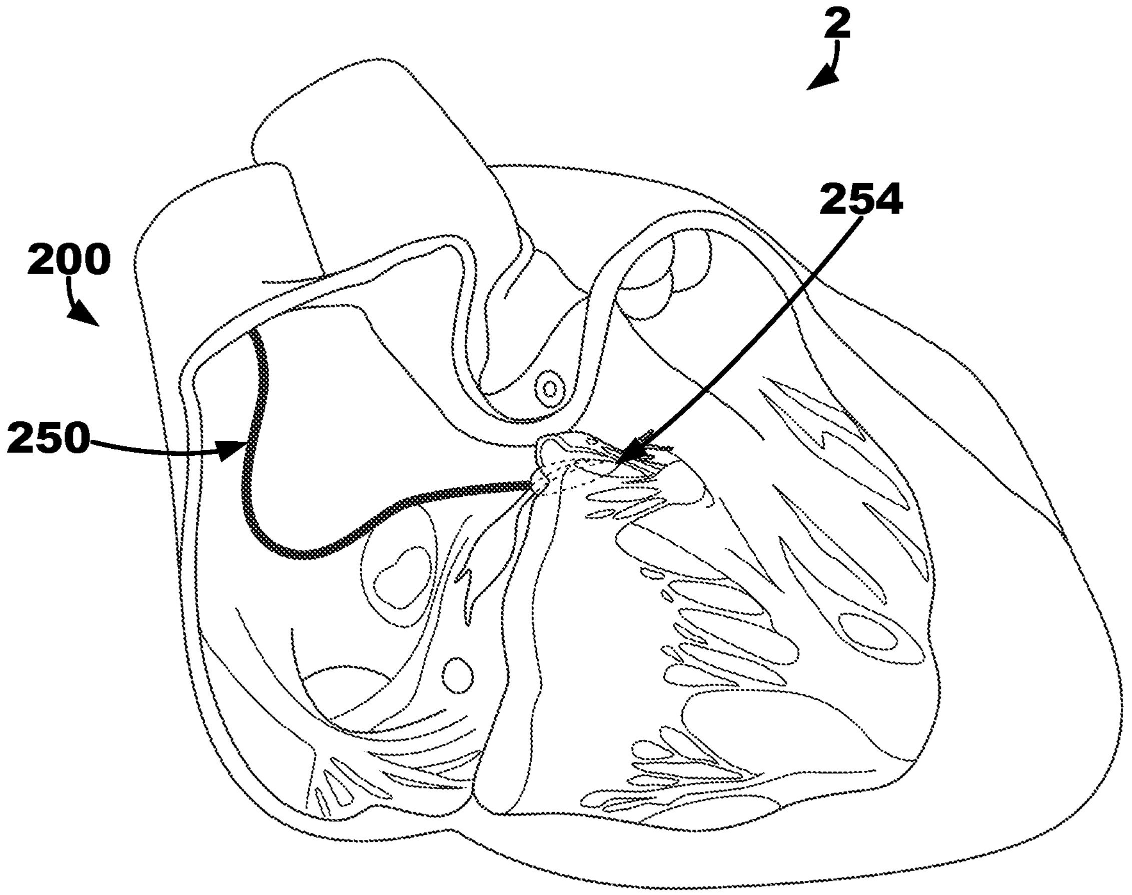
FIGS. 6-7 are conceptual diagrams showing one example of an implantable medical device (IMD) including an implantable medical lead or leadlet extending through the RA endocardium.
Figure 7:
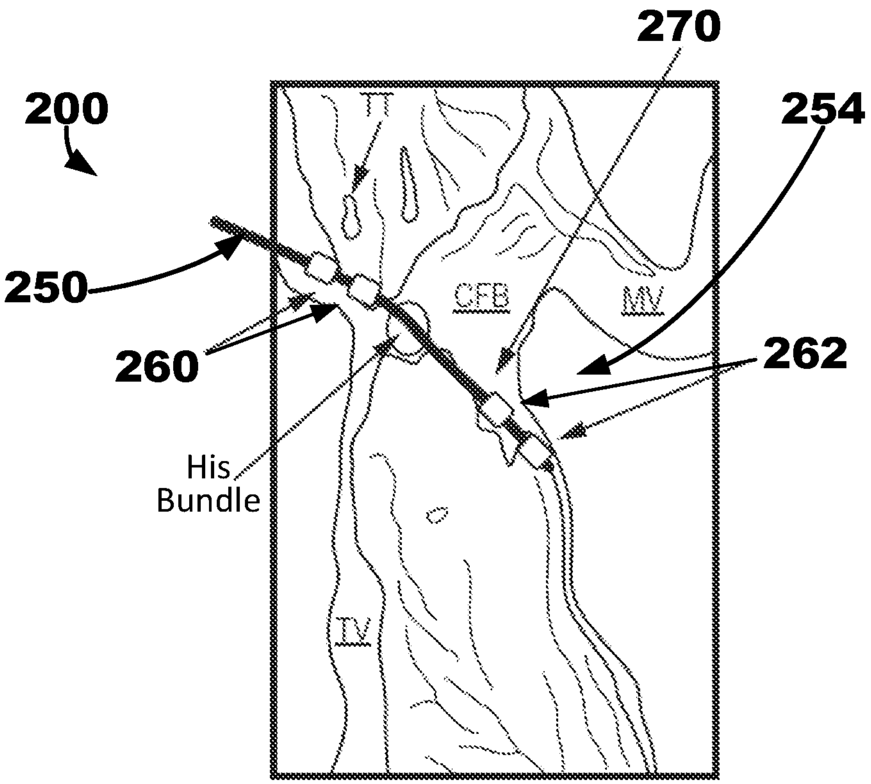

FIGS. 6-7 are conceptual diagrams showing one example of an implantable medical device (IMD) 200 including an implantable medical lead or leadlet 250 extending through the right atrial endocardium. Although a lead 250 is described herein, a leadlet extending from an intracardiac implantable housing may also be used. A distal portion 254 of the lead 250 may be positioned in the left ventricular myocardium extending along the left ventricular endocardial wall, for example, toward the apex of the patient's heart. The distal portion 254 may be proximate to the left bundle branch (LBB) of the patient's heart 2. Any suitable delivery system and method may be used to deliver the lead 250. In at least one embodiment, the delivery systems described herein with respect to FIG. 5 and FIGS. 10-14 may be utilized. For example, a delivery system may be configured to puncture the right atrial endocardium and central fibrous body (CFB) to allow the lead 250 to be simply pushed into the septal myocardium, or interventricular septal wall, and tunneled up or down the septum as shown by the trajectory 270 in FIG. 7. The lead 250 may be tunneled into the basal-septal, mid-septal, or even apical septal region.

A multipolar lead may be used such as, e.g., the quadripolar lead 590 described herein with respect to FIG. 14. The distal portion 254 of the lead 250 may have a quadripolar configuration, which may be the same or similar to an ATTAIN STABILITY™ or ATTAIN STABILITY QUAD™ or ATTAIN PERFORMA™ leads available from Medtronic plc of Dublin, Ireland. A side helix or hook usable for fixation that may be disposed on the distal portion, which may be selectively electrically active or passive and may be mechanically active or adjustable. Another exemplary lead that may be employed is described in U.S. Pat. No. 9,901,732 to Sommer et al., granted Feb. 27, 2018, which is incorporated by reference in its entirety, in which electrodes are jumpered in a diagonal configuration in order to increase the opportunity to capture cardiac tissue.

The guiding element may be a guidewire, a steerable stylet or wire, or a hybrid of stylet guidewire that is a part of the ATTAIN family, may be used to guide the lead into the septum. With multiple electrodes and different spacing, one lead may be used to pace the atrium and multiple locations down the septum. One example of a guiding element that may be used is described in U.S. Pat. No. 7,881,806 to Sommer et al., granted Feb. 1, 2011, which is incorporated by reference in its entirety.

The IMD 200 may be used in any suitable manner. In some embodiments, a method of implanting and using the IMD 200 may include delivering the delivery catheter and a penetration element disposed in the delivery catheter to the right atrial endocardium in or proximate to the triangle of Koch region of a patient's heart, such as in the coronary sinus ostium. The method of implanting and using the IMD 200 may also include puncturing the right atrial endocardium and the central fibrous body using the penetration element to form an opening through the right ventricular endocardium and the central fibrous body and into the interventricular septal wall. Then, the penetration element may be retracted. Then, a distal portion of a guide element may be advanced through the delivery catheter and the opening and into the interventricular septal wall to extend along the left ventricular endocardial wall.

In addition, the method of implanting and using the IMD 200 may include delivering a distal portion 254 of an implantable medical lead 250 over the guide element to the left ventricular myocardium to extend along the left ventricular endocardial wall to position one or more left ventricular electrodes 262 on the distal portion 254 in the left ventricular myocardium. In some embodiments, the left ventricular electrodes 262 may be positioned proximate to the left bundle branch of the conduction system of the patient's heart. In some embodiments, the method of implanting and using the IMD 200 may also include implanting one or more right atrial electrodes 260 proximate to the right atrial endocardium. The right atrial electrodes 260 may be positioned proximally along the lead 250 to the left ventricular electrodes 262 on the distal portion 254 of the implantable medical lead 250.

In some embodiments, the method of using the IMD 100 may further include monitoring electrical activity of at least one of the right atrial electrodes 260 and the left ventricular electrodes 262, and delivering pacing therapy using at least one of the right atrial electrodes 260 and the left ventricular electrodes 262. In some embodiments, delivering pacing therapy may include delivering pacing pulses to the left ventricular electrodes 262 configured to pace the left bundle branch of the conduction system of the patient's heart. Further, In some embodiments, the implantable medical lead may include a plurality of left ventricular electrodes, a plurality of right atrial electrodes, or both.

Figure 8:
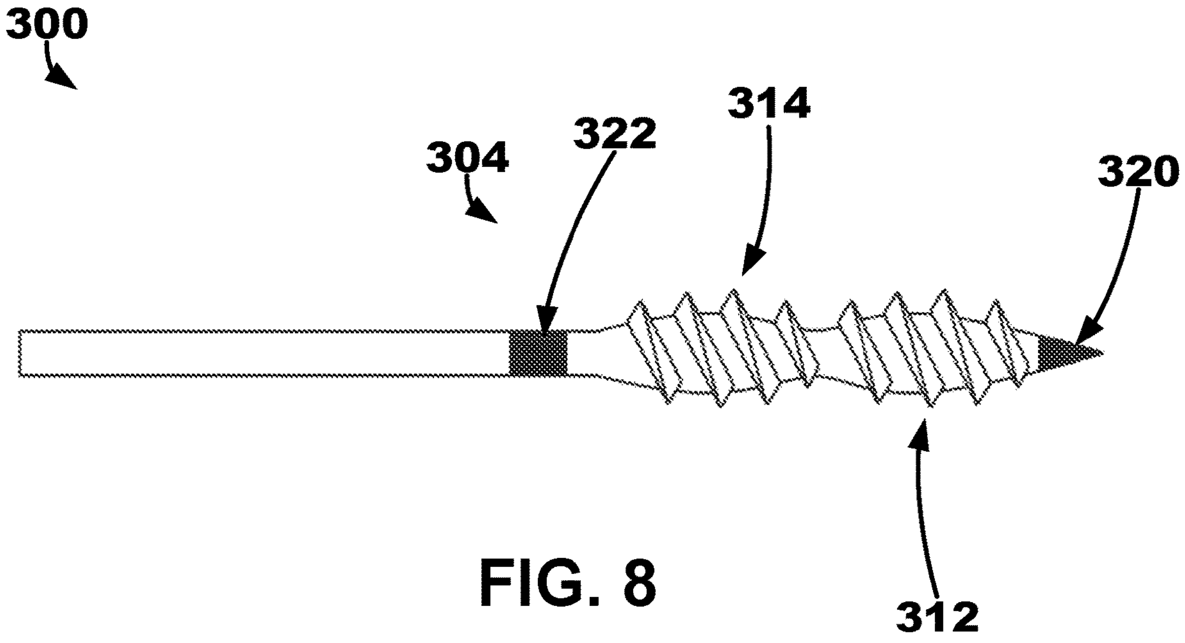
FIG. 8 is a conceptual diagram showing one example of a "screw-like" structure that may be used to support and fixate one or more electrodes in myocardial tissue.

A conceptual diagram showing one example of a "screw-like" structure that may be used to support and fixate one or more electrodes in myocardial tissue is depicted in FIG. 8. In some embodiments, IMD or LIMD may include an elongate member 300 extending between a proximal portion and a distal portion 304. A first electrode 320 may be disposed on the distal portion 304 of the elongate member. A second electrode 322 may be disposed proximal to the first electrode 320 on the distal portion 304 of the elongate member 300. A first threaded bulb region 312 may be disposed between the first and second electrodes 320, 322 on the distal portion 304 of the elongate member 300. A second threaded bulb region 314 disposed between the first threaded bulb region 312 and the second electrode 322 on the distal portion 304 of the elongate member 300. In some embodiments, the threaded bulb regions 312, 314 may share a similar threaded pattern or spacing.

Figure 9:
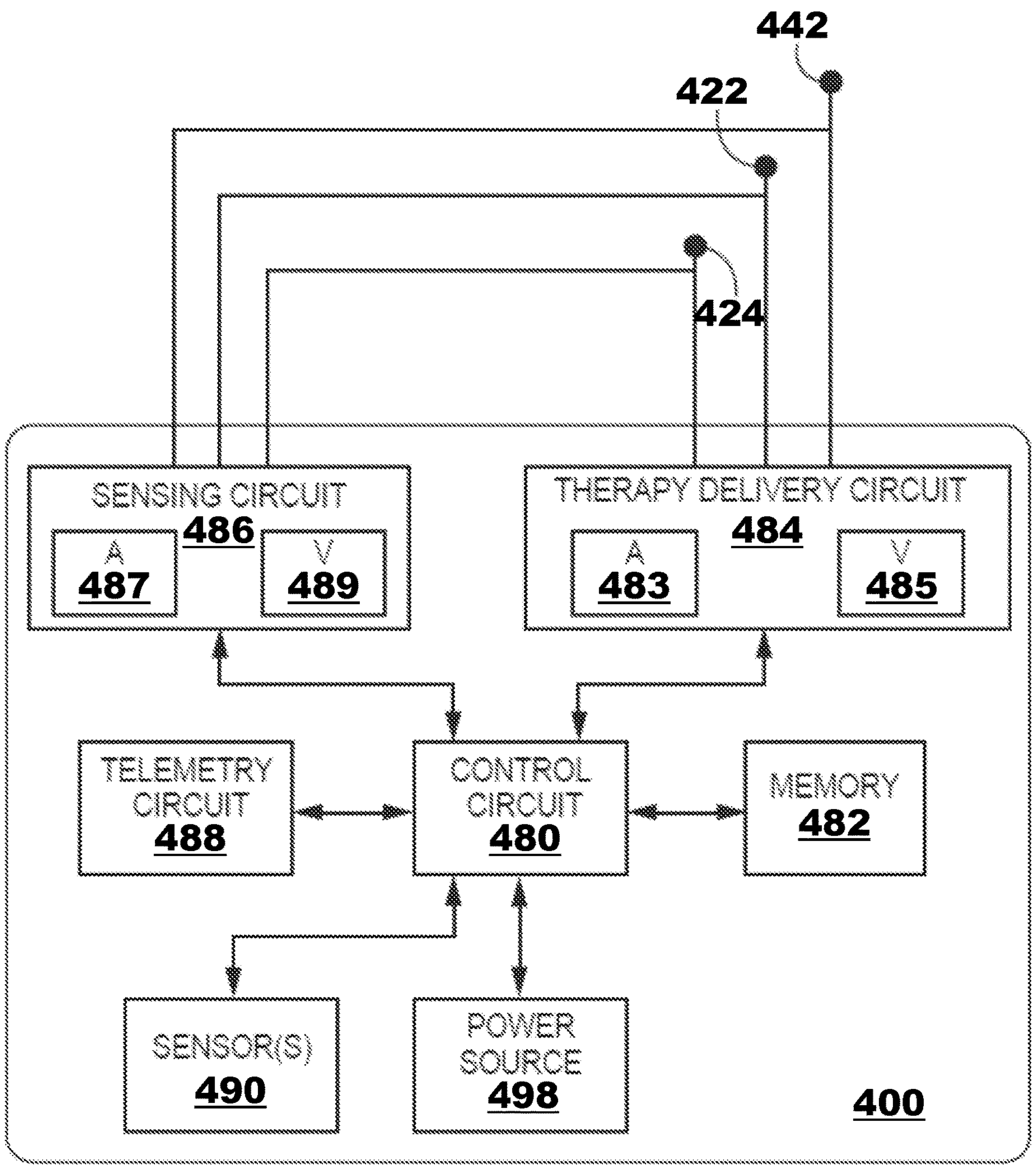
FIG. 9 is a block diagram of illustrative circuitry that may be enclosed within a housing of the devices and systems of FIGS. 1-8, for example, to provide the functionality and therapy described herein.
Figure 10:
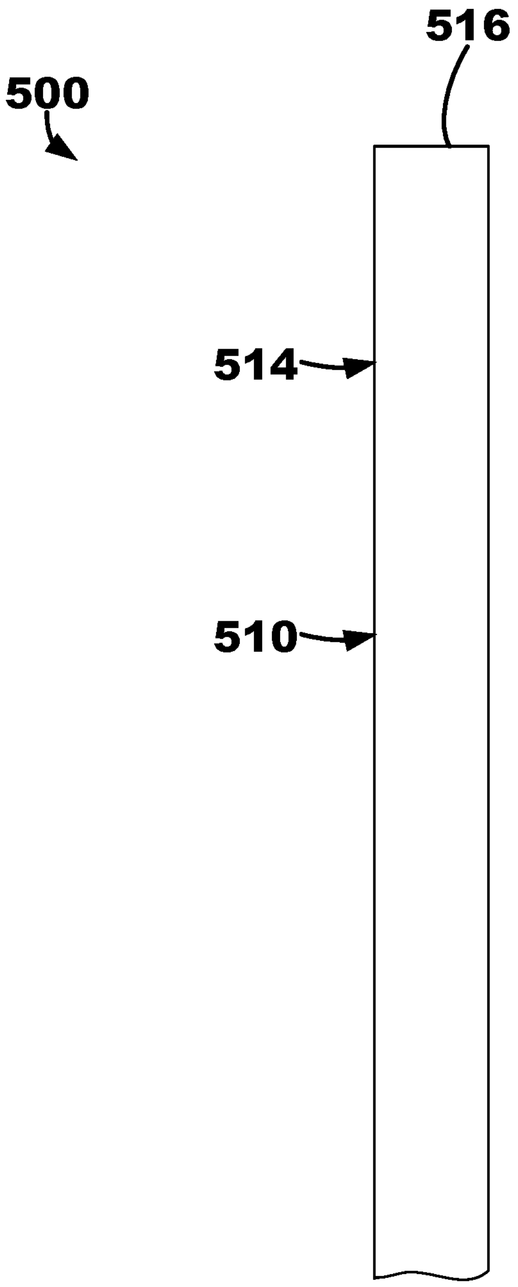
FIG. 10 depicts an illustrative ventricular septum lead and delivery system with components all located with the delivery catheter.

FIG. 9 is a block diagram of circuitry that may be enclosed within the housings of an illustrative IMD 400 to provide the functions of cardiac therapy described herein with respect to FIGS. 1-8. In other words, the IMD 400 may be used with any one or more of the embodiments described with respect to FIGS. 1-8. The electronic circuitry of the device 400 may include software, firmware, and hardware that cooperatively monitor atrial and ventricular electrical cardiac signals, determine when a cardiac therapy is necessary, and/or deliver electrical pulses to the patient's heart according to programmed therapy mode and pulse control parameters. The electronic circuitry may include a control circuit 480 (e.g., including processing circuitry), a memory 482, a therapy delivery circuit 484, a sensing circuit 486, and/or a telemetry circuit 488. In some examples, the device 400 includes one or more sensors 490 for producing a signal that is correlated to a physiological function, state, or condition of the patient, such as a patient activity sensor, for use in determining a need for pacing therapy and/or controlling a pacing rate.

The power source 498 may provide power to the circuitry of the device 400 including each of the components 480, 482, 484, 486, 488, and 490, as needed. The power source 498 may include one or more energy storage devices, such as one or more rechargeable or non-rechargeable batteries. The connections between the power source 498 and each of the components 480, 482, 484, 486, 488, and 490 are to be understood from the general block diagram illustrated but are not shown for the sake of clarity. For example, the power source 498 may be coupled to one or more charging circuits included in the therapy delivery circuit 484 for providing the power needed to charge holding capacitors included in the therapy delivery circuit 484 that are discharged at appropriate times under the control of the control circuit 480 for delivering pacing pulses, e.g., according to a dual chamber pacing mode such as DDI(R). The power source 498 may also be coupled to components of the sensing circuit 486, such as sense amplifiers, analog-to-digital converters, switching circuitry, etc., sensors 490, the telemetry circuit 488, and the memory 482 to provide power to the various circuits.

Any suitable technique may be used to recharge a rechargeable power source 498. In some embodiments, the device 400 may include an antenna, inductive coils, or other inductive coupling structures configured to couple to another device, such as an external charger or programmer, to receive power in situ. Various examples of charging a leadless implantable medical device are described in U.S. Patent Pub. No. 2018/0212451 (Schmidt et al.), filed Jan. 26, 2017, entitled "Recharge of Implanted Medical Devices," which is incorporated herein by reference in its entirety. The device 400 may also be configured to use various techniques to extend the life of the power source 498, such as a low-power mode.

Various examples of power sources and techniques related to power sources may be used, such as those found in, for example, U.S. Pat. No. 8,383,269 (Scott et al.), granted Feb. 26, 2013, U.S. Pat. No. 8,105,714 (Schmidt et al.), granted Jan. 31, 2012, and U.S. Pat. No. 7,635,541 (Scott et al.), granted Dec. 22, 2009, each of which is incorporated herein by reference in its entirety.

The functional blocks shown represent functionality included in the device 400 and may include any discrete and/or integrated electronic circuit components that implement analog, and/or digital circuits capable of producing the functions attributed to the device 400 herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device. Providing software, hardware, and/or firmware to accomplish the described functionality in the context of any modern cardiac medical device system, given the disclosure herein, is within the abilities of one of skill in the art.

The memory 482 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 482 may include a non-transitory computer readable media storing instructions that, when executed by one or more processing circuits, cause the control circuit 480 and/or other processing circuitry to perform a single, dual, or triple chamber pacing (e.g., single or multiple chamber pacing) function or other sensing and therapy delivery functions attributed to the device 400. The non-transitory computer-readable media storing the instructions may include any of the media listed above.

The control circuit 480 may communicate, e.g., via a data bus, with the therapy delivery circuit 484 and the sensing circuit 486 for sensing cardiac electrical signals and controlling delivery of cardiac electrical stimulation therapies in response to sensed cardiac events, e.g., P-waves and R-waves, or the absence thereof. The electrodes 422, 424, 442 (e.g., left ventricular electrodes, right ventricular electrodes, right atrial electrodes, housing electrodes, etc.) may be electrically coupled to the therapy delivery circuit 484 for delivering electrical stimulation pulses to the patient's heart and to the sensing circuit 486 and for sensing cardiac electrical signals.

The sensing circuit 486 may include an atrial (A) sensing channel 487 and a ventricular (V) sensing channel 489. For example, the electrodes 422, 424 may be coupled to the atrial sensing channel 487 for sensing atrial signals, e.g., P-waves attendant to the depolarization of the atrial myocardium. Further, in some examples, the sensing circuit 486 may include switching circuitry for selectively coupling one or more of the available electrodes to cardiac event detection circuitry included in the atrial sensing channel 487. Switching circuitry may include a switch array, switch matrix, multiplexer, or any other type of switching device suitable to selectively couple components of the sensing circuit 486 to selected electrodes. Further, for example, electrodes 424, 442 may be coupled to the ventricular sensing channel 489 for sensing ventricular signals, e.g., R-waves attendant to the depolarization of the ventricular myocardium.

Each of the atrial sensing channel 487 and the ventricular sensing channel 489 may include cardiac event detection circuitry for detecting P-waves and R-waves, respectively, from the cardiac electrical signals received by the respective sensing channels. The cardiac event detection circuitry included in each of the channels 487 and 489 may be configured to amplify, filter, digitize, and rectify the cardiac electrical signal received from the selected electrodes to improve the signal quality for detecting cardiac electrical events. The cardiac event detection circuitry within each channel 487 and 489 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 487 and 489 under the control of the control circuit 480, e.g., based on timing intervals and sensing threshold values determined by the control circuit 480, stored in the memory 482, and/or controlled by hardware, firmware, and/or software of the control circuit 480 and/or the sensing circuit 486.

Upon detecting a cardiac electrical event based on a sensing threshold crossing, the sensing circuit 486 may produce a sensed event signal that is passed to the control circuit 480. For example, the atrial sensing channel 487 may produce a P-wave sensed event signal in response to a P-wave sensing threshold crossing. The ventricular sensing channel 489 may produce an R-wave sensed event signal in response to an R-wave sensing threshold crossing. The sensed event signals may be used by the control circuit 480 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 487 may cause the control circuit 480 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the control circuit 480 receives an R-wave sensed event signal from the ventricular sensing channel 489, the control circuit 480 may use the therapy delivery circuit 484 to deliver the scheduled ventricular pacing pulse synchronized to the sensed P-wave.

In some examples, the device 400 may be configured to deliver a variety of pacing therapies including bradycardia pacing, cardiac resynchronization therapy, post-shock pacing, and/or tachycardia-related therapy, such as ATP, among others. For example, the device 40 may be configured to detect non-sinus tachycardia and deliver ATP. The control circuit 480 may determine cardiac event time intervals, e.g., P-P intervals between consecutive P-wave sensed event signals received from the atrial sensing channel 487, RR intervals between consecutive R-wave sensed event signals received from the ventricular sensing channel 489, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 484 may include atrial pacing circuit 483 and ventricular pacing circuit 485. Each pacing circuit 483 and 485 may include charging circuitry, one or more charge storage devices such as one or more low voltage holding capacitors, an output capacitor, and/or switching circuitry that controls when the holding capacitor (s) are charged and discharged across the output capacitor to deliver a pacing pulse to the pacing electrode vector coupled to respective pacing circuits 483 or 485. The electrodes 424, 442 may be coupled to the ventricular pacing circuit 485 as a bipolar cathode and anode pair for delivering ventricular pacing pulses, e.g., upon expiration of an AV or VV pacing interval set by the control circuit 480 for providing atrial-synchronized ventricular pacing and a basic lower ventricular pacing rate.

The atrial pacing circuit 483 may be coupled to, for example, the electrodes 422, 424 to deliver atrial pacing pulses. The control circuit 480 may set atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 487. The control circuit 480 starts an AV pacing interval in response to a delivered atrial pacing pulse to provide synchronized multiple chamber pacing (e.g., dual or triple chamber pacing).

Charging of a holding capacitor of the atrial or ventricular pacing circuit 483 or 485 to a programmed pacing voltage amplitude and discharging of the capacitor for a programmed pacing pulse width may be performed by the therapy delivery circuit 484 according to control signals received from the control circuit 480. For example, a pace timing circuit included in the control circuit 480 may include programmable digital counters set by a microprocessor of the control circuit 480 for controlling the basic pacing time intervals associated with various single chamber or multiple chamber pacing (e.g., dual or triple chamber pacing) modes or anti-tachycardia pacing sequences. The microprocessor of the control circuit 480 may also set the amplitude, pulse width, polarity, or other characteristics of the cardiac pacing pulses, which may be based on programmed values stored in the memory 482.

The device 400 may include other sensors 490 for sensing signals from the patient for use in determining a need for and/or controlling electrical stimulation therapies delivered by the therapy delivery circuit 484. In some examples, a sensor indicative of a need for increased cardiac output may include a patient activity sensor, such as an accelerometer. An increase in the metabolic demand of the patient due to increased activity as indicated by the patient activity sensor may be determined by the control circuit 480 for use in determining a sensor-indicated pacing rate.

Control parameters utilized by the control circuit 480 for sensing cardiac events and controlling pacing therapy delivery may be programmed into the memory 482 via the telemetry circuit 488, which may also be described as a communication interface. The telemetry circuit 488 includes a transceiver and antenna for communicating with an external device such as a programmer or home monitor, using radio frequency communication or other communication protocols. The control circuit 480 may use the telemetry circuit 488 to receive downlink telemetry from and send uplink telemetry to the external device. In some cases, the telemetry circuit 488 may be used to transmit and receive communication signals to/from another medical device implanted in the patient.

An illustrative ventricular septum lead and delivery system 500 is depicted in FIGS. 10-14 that may be used in a similar manner as the illustrative method and system described herein with respect to FIG. 4 The lead and delivery system 500 may include a delivery catheter 510 that extends from a proximal end region (not depicted) to a distal end region 514. The delivery catheter 510 may define an opening, or aperture, extending from a proximal end to a distal end 516. The other components of the lead and delivery system 500 may be located, or positioned, within the opening of the delivery catheter 510 for delivery to a target location such as right ventricular endocardium, the ventricular septum, etc.

Figure 11:
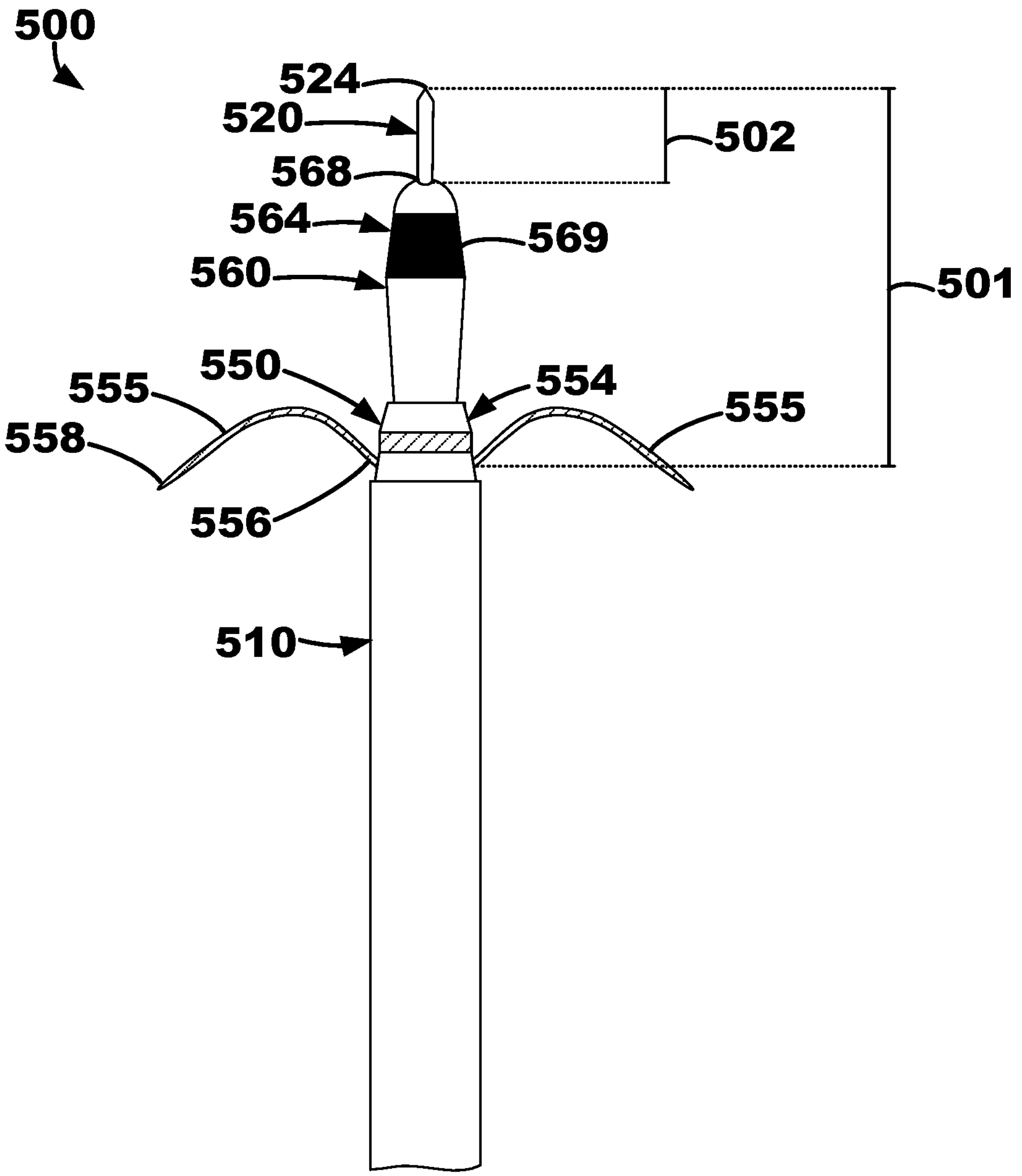
FIG. 11 depicts the ventricular septum lead and delivery system of FIG. 10 with the delivery catheter partially retracted thereby releasing the fixation tines of the outer lead body.

The delivery catheter 510 may be manipulable by a clinician to locate, or position, the distal end 516 proximate (e.g., adjacent, in close contact with, substantially flush to, etc.) a target location such as, e.g., the right ventricular endocardium of the interventricular septal wall of a patient's heart, the right atrial endocardium and central fibrous body (CFB), etc. When the delivery catheter 510 is positioned proximate the target location, the delivery catheter 510 may be retracted thereby exposing an penetration element 520 located within an inner lead body 560, which is located in an outer lead body 550, as shown in FIG. 11. In other words, the delivery catheter 510 may be moved relative to the remaining components of the system 500. In at least one embodiment, the remaining components of the system 500 may be held, or kept, secure and stationary while the delivery catheter 510 is pulled proximally away from the target location.

Figure 12:
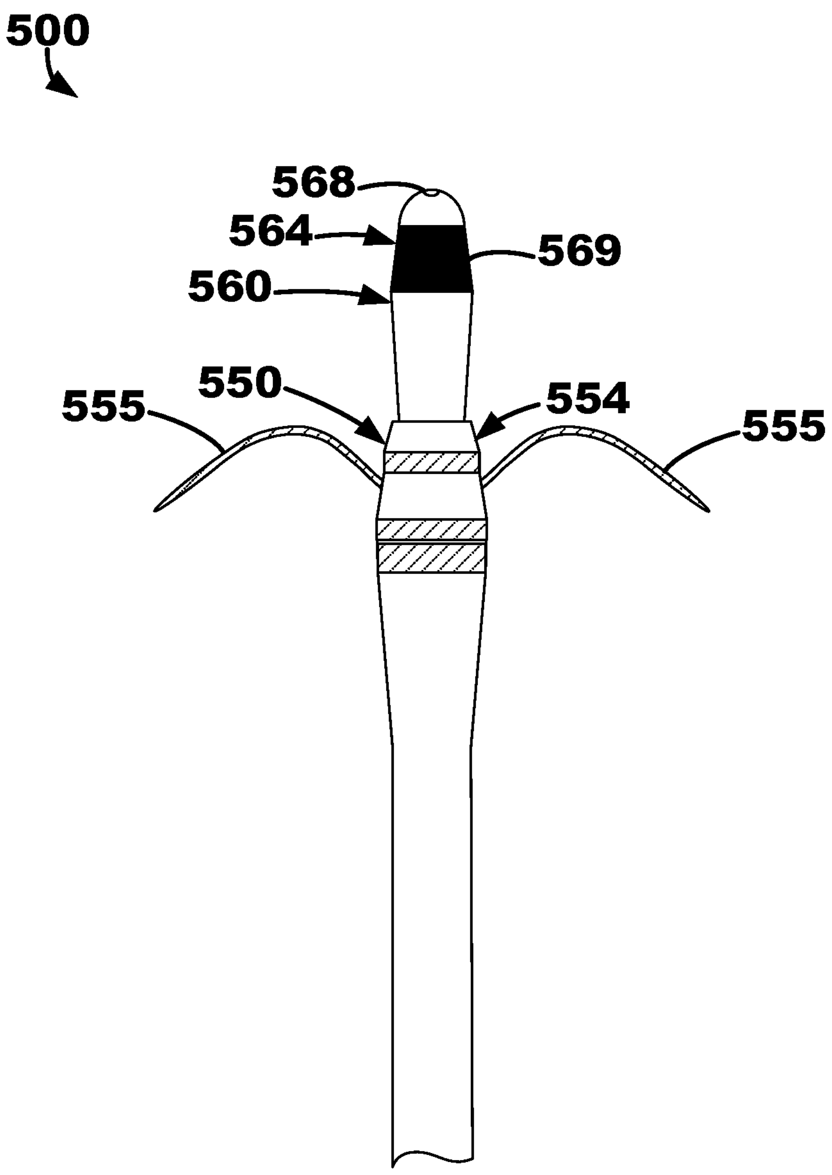
FIG. 12 depicts the ventricular septum lead and delivery system of FIGS. 10-11 with the delivery catheter and the penetrator element both completed removed.
Figure 13:
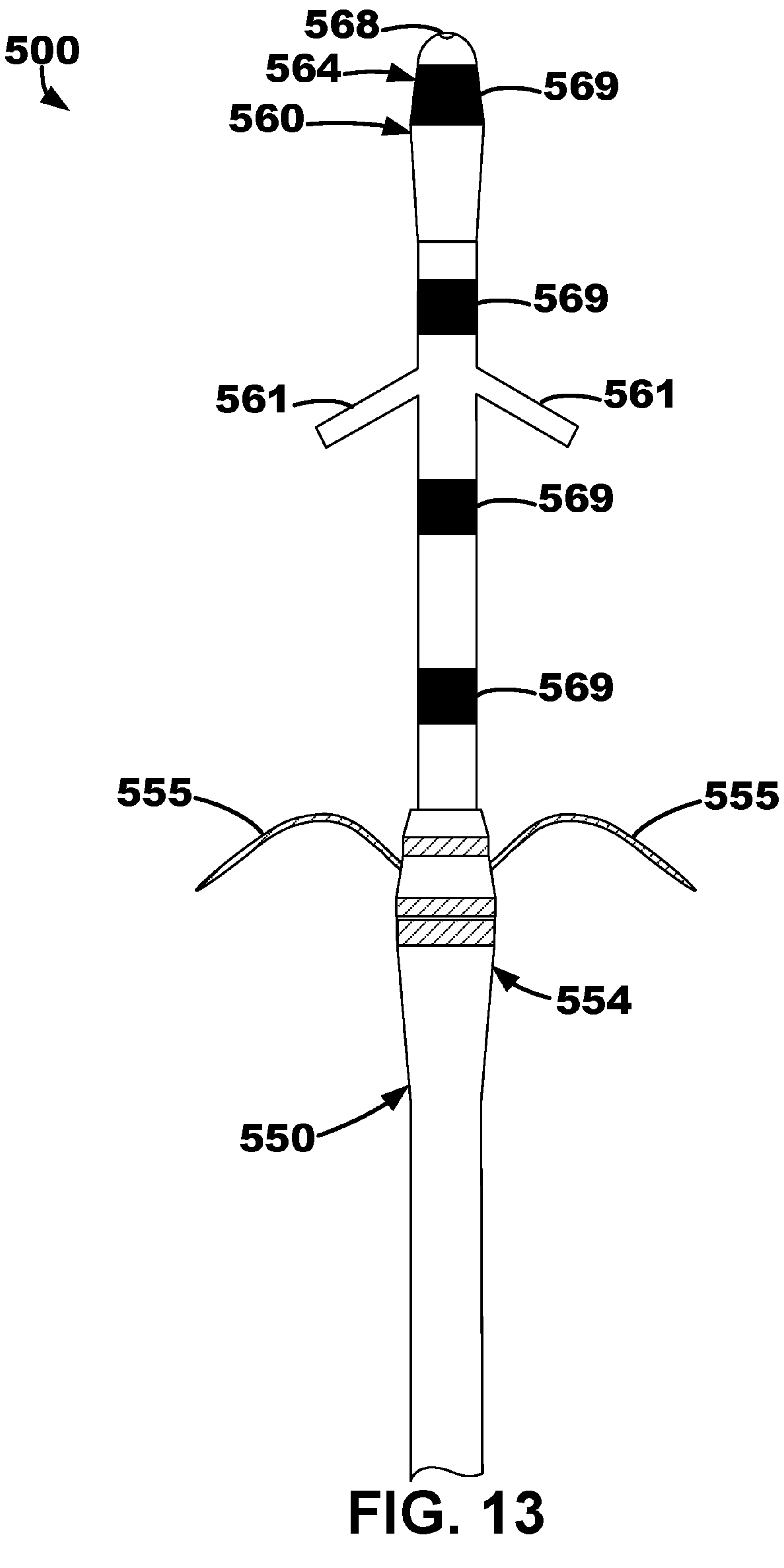
FIG. 13 depicts the ventricular septum lead and delivery system of FIGS. 10-11 with the inner lead body extended from the outer lead body.

The outer lead body 550 extends from a proximal end region to a distal end region 554 and includes, among other things, fixation elements 555 located proximate the distal end region 554. The fixation elements 555 may be resilient such that, e.g., they may be "folded up" within the delivery catheter 510 and may move, or "spring," to a deployed state as shown in FIG. 11. In other words, the fixation elements 555 may be configured in a stowed configuration and a deployed configuration. The fixation elements 555 may be predisposed in the deployed configuration and configured to move back to the deployed configuration without application of an outside force. Thus, the delivery catheter 510 may provide an outside force by contacting the fixation elements 555 to hold (e.g., "fold down," restrict, etc.) the fixation elements 555 in the stowed configuration when the distal end region 554 is located within the opening of the delivery catheter 510. More specifically, each of the fixation elements extends from a proximal end 556 attached to the distal end region 554 to a distal end 558, and when the stowed configuration, the distal end 558 may extend and point to the distal end 516 of the delivery catheter 510. When the distal end 516 of the delivery catheter 510 is adjacent tissue at a target location and the delivery catheter 510 is moved to release the fixation elements 555 of the outer lead body 550, the fixation elements 555 may pierce the tissue at the target location and "pull" the outer lead body 550 (and inner lead body 560 and penetration element 520) into the tissue. Such fixation element configuration is described further in U.S. Pat. App. Pub. No. 2019/0076646 A1 entitled "Securing an Implantable Medical Device In Position while Reducing Perforations" published on Mar. 14, 2019, which is incorporated by reference herein in its entirety. Although two fixation elements 555 are depicted in FIGS. 11-13, it is be understood that one fixation element or more than two fixation elements may be used with the illustrative systems and methods described herein.

A distance 501 may be defined between where the proximal end 556 of the fixation element 555 is coupled to (e.g., extends from) the outer lead body 550 and a distal penetration end 524 of the penetration element 520. The distance 501 may be between about 2 millimeters (mm) and about 15 mm. In one embodiment, the distance 501 may be 4 mm. In one or more embodiments, the distance 501 may be greater than or equal to 2 mm, greater than or equal to 5 mm, greater than or equal to 8 mm, etc. and/or less than or equal to 4 mm, less than or equal to 7 mm, less than or equal to 10 mm, less than or equal to 12 mm etc.

In some embodiments, the distance 501 may be referred to as an initial penetration distance because, for example, the force applied to the inner lead body 560 and penetration element 520 by the fixation elements 555 being released in the deployed positioned and "grabbing" tissue may be sufficient to drive the inner lead body 560 and penetration element 520 into the target location up to the distal end region 554 of the outer lead body 550. In other words, the fixation elements 555 may "drive" the inner lead body 560 and penetration element 520 into the tissue across the distance 501.

Further, a relationship between the distance 501 and the length and shape of the fixation element 555 (i.e., from the proximal end 556 to the distal end 558) may be defined to provide effective penetration to a particular target location. For example, the length of the fixation elements 555 may be less than the distance 501 by about 20% or mm to, e.g., allow the penetration element 530 and the inner lead body 560 (e.g., at least the distal end 568) to contact and/or penetrate the endocardium prior the fixation elements 555 contacting the endocardium.

The outer lead body 550 may include one or more electrodes within the distal end region 554. In at least one embodiment, the fixation elements 555 may function as electrodes to, e.g., sense and or pace right ventricular tissue when the fixation elements 555 are located in the right ventricular endocardium.

The outer lead body 550 defines an opening extending from the proximal end region to the distal end region 554, and as shown in FIGS. 11-13, the inner lead body 560 may be located therein. The inner lead body 560 may also extend from a proximal end region to a distal end region 564 and may define an opening extending from the proximal end region to the distal region 564, within which the penetration element 520, a guide wire, or stylet may be inserted (e.g., located therethrough). As shown in FIG. 11, a penetration element 520 extends from a proximal end to the distal penetration end 524 and is located in the opening of the inner lead body 560 extending distally from a distal end 568 of the inner lead body 560.

The system 500 may be configured to restrict, or limit, the distance 502 that the penetration element 520 may extend beyond the distal end 568 of the inner lead body 560. The distance 502 may be defined between the distal end 568 of the inner lead body 560 and the distal penetration end 524 of the penetration element 520 (e.g., a sharpened point configured for penetration for the right ventricular endocardium). The distance 502 may be between about 1 millimeter (mm) and about 5 mm. In one embodiment, the distance 502 may be 2 mm. In one or more embodiments, the distance 502 may be greater than or equal to 1 mm, greater than or equal to 1.5 mm, greater than or equal to 2.5 mm, etc. and/or less than or equal to 5 mm, less than or equal to 4 mm, less than or equal to 3.5 mm, less than or equal to 3 mm etc.

The inner lead body 560 may further include one or more electrodes 569 that may be configured to be positioned within the intraventricular septum to sense cardiac electrical activity and deliver pacing therapy (e.g., cardiac conduction system pacing therapy, left bundle branch pacing therapy, etc.). Only one of the electrodes 569 is exposed on FIG. 11.

Once the outer lead body 550 is fixated to the target location such as, e.g., the right ventricular endocardial wall, the inner lead body 560 may be moved relative to the outer lead body 550 to implant the distal end region 564 of the inner lead body 560 within the ventricular septum. More specifically, the outer lead body 550 may remain relatively stationary as being fixated, or anchored, to tissue at the target location. The penetration element 520 will have been used to penetrate the target location (e.g., the right ventricular endocardium), and thus, the inner lead body 560 may then follow the opening made by the penetration element 520 (e.g., tunnel into the opening). First, the penetration element may be removed (e.g., retracted proximally) from the inner lead body 560. In some embodiments, the inner lead body 560 may then be moved relative the outer lead body 550 to position to the distal end region 564 in the desired location for sensing and/or pacing (e.g., with the intraventricular septum proximate the left ventricular endocardium with puncturing or penetrating the left ventricular endocardium). In other embodiments, a guide wire or stylet may be inserted through the opening of the inner lead body 560, which may then be used to position the distal end region 564 of the inner lead body 560 in the desired location. Additionally, the distal end region 564 and distal end 568 of the inner lead body 560 may define a curvature or taper configured to provide tunneling functionality into tissue and to effectively expand the opening made by the penetration element 520.

The inner lead body 560 and the outer lead body 550 are depicted in FIG. 12 with the penetration element 520 and the delivery catheter 510 completely removed therefrom. The inner lead body 560 moved distally away from the outer lead body 550, e.g., after the outer lead body 550 is fixated to a target location, is depicted in FIG. 13. As shown, the inner lead body 560 may also include, or define, fixation elements 561 configured to fixate, or fix, the inner lead body 560 within the desired location. In this embodiment, the fixation elements 561 are configured to provide "one-way" fixation. Thus, the fixation elements 561 restrict the inner lead body 560 from moving proximally towards (e.g., back towards) the outer lead body 550 after the inner lead body 560 has been moved away (e.g., distally) from the outer lead body 550. Further, as the inner lead body 560 becomes more exposed, more of the electrodes 569 along the inner lead body 560 are shown.

In brief, the lead and delivery system 500 of FIGS. 10-13 may provide for mechanical injection into the intraseptal space. It may be described that the lead is loaded into a delivery system, a perforating element is extended out of the distal of the lead and is shrouded by the catheter. After lead has been positioned in desired implant location, the lead may be extended out of catheter. As the lead extends out of catheter, the fixation elements (e.g., nitinol tines) may engage the endocardium. Further, as the fixation elements actuate, they extend the lead out of the delivery system. Still further, as the lead tip/needle is actuated forward, the lead is injected into the septum and simultaneously fixated. Then, the needle may be retracted, and the inner assembly of the lead may then be tunneled to desired location. In at least one example, to guide the lead during tunneling, the lead/catheter can be shifted, and shaped/steerable stylets can be used. Further, the inner and outer lead assemblies may then be secured.

An illustrative quadripolar lead 590 that may be used with the systems and methods described herein is depicted FIG. 14. As shown, the lead 590 includes four di-pole electrodes 592 spaced along the length of the lead 590. The electrodes 592 may be spaced apart between about 1 millimeters (mm) and about 5 mm. Additionally, the lead 590 includes a plurality of small fixation elements 594 located between each of the electrodes 592. In one embodiment, the fixation elements 594 may be flexible, polymer tines that can fold down in a delivery catheter and can deploy into to muscle fiber when deployed. Also, when enough force is applied, the fixation elements 594 will flex and allow removal chronically (e.g., pulled out of an implant location, moved proximally away from an implant location).

In another embodiment, the lead 590 may include a helix or helical fixation element as opposed to the fixation elements 594 shown in FIG. 14. A helix may allow the lead 590 to be fixated, and then the inner lead body to be advanced after outer lead body is fixated.

In another embodiment, similar to the fixation elements 561 of the inner lead body 560, the fixation elements 594 may be configured to be predominantly "one-way." In other words, the fixation elements 594 may restrict proximal movement of the lead 590 more than distal movement of the lead 590 to, e.g., allow for implantation but restrict dislodgment in the proximal direction.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

Terms related to orientation, such as "proximal," "distal," or "end," are used to describe relative positions of components and are not meant to limit the absolute orientation of the embodiments contemplated.

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out functionality.

The singular forms "a," "an," and "the" encompass embodiments having plural referents unless its context clearly dictates otherwise.

The term "or" is generally employed in its inclusive sense, for example, to mean "and/or" unless the context clearly dictates otherwise. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

ILLUSTRATIVE EXAMPLES

Example 1: An implantable medical device comprising:

a plurality of electrodes comprising:
  - a right atrial electrode positionable within the right atrium to deliver cardiac therapy to or sense electrical activity of the right atrium of the patient's heart; and
  - at least one left ventricular electrode positionable proximate the left ventricle of the patient's heart;

a housing extending from a proximal end region to a distal end region, wherein the right atrial electrode is leadlessly coupled to the proximal end region;

a leadlet extending from a proximal region to a distal region, wherein the proximal region is coupled to the distal end region of the housing and the at least one ventricular electrode is coupled to the distal region of the leadlet, wherein the leadlet is configured to extend through the coronary sinus ostium and into the coronary sinus or a coronary vein of the patient's heart to position the least one left ventricular electrode proximate the left ventricle of the patient's heart;

a therapy delivery circuit within the housing and operably coupled to the plurality of electrodes to deliver cardiac therapy to the patient's heart;

a sensing circuit within the housing and operably coupled to the plurality of electrodes to sense electrical activity of the patient's heart; and a controller within the housing and comprising processing circuitry operably coupled to the therapy delivery circuit and the sensing circuit, the controller configured to:
  - monitor electrical activity using the processing circuitry and one or more of the plurality of electrodes; and
  - delivering pacing therapy using the processing circuitry and one or more of the plurality of electrodes.

Example 2. The device as in Example 1, wherein the at least one left ventricular electrode is implantable into the left ventricular myocardium from the coronary sinus proximal to the posterior vein of the patient's heart.

Example 3. The device as in Example 1, wherein the at least one left ventricular electrode is implantable into the anterior interventricular vein of the patient's heart.

Example 4. The device as in Example 1, wherein the at least one left ventricular electrode is implantable into the lateral vein of the patient's heart.

Example 5. The device as in any one of Examples 1-4, wherein delivering pacing therapy comprises utilizing field steering to avoid left atrial capture by the at least one left ventricular electrode.

Example 6: A method comprising:

implanting a right atrial electrode in the right atrial endocardium or in the right atrial myocardium of a patient's heart, the right atrial electrode being leadlessly coupled to a proximal end region of an implantable housing, wherein processing circuitry is disposed in the housing and operably coupled to the right atrial electrode;

implanting at least one left ventricular electrode through the coronary sinus ostium and into the coronary sinus or a coronary vein of the patient's heart, the at least one left ventricular electrode being coupled to a distal region of a leadlet, a proximal region of the leadlet being coupled to a distal end region of the implantable housing, wherein the processing circuitry is operably coupled to the at least one left ventricular electrode;

monitoring electrical activity using the processing circuitry and one or more of the right atrial electrode and the at least one left ventricular electrode; and delivering pacing therapy using the processing circuitry and at one or more of the right atrial electrode and the at least one left ventricular electrode.

Example 7: The method as in Example 6, wherein implanting the left ventricular electrode comprises implanting the left ventricular electrode into the left ventricular myocardium from the coronary sinus proximal to the posterior vein of the patient's heart.

Example 8: The method as in Example 6, wherein implanting the left ventricular electrode comprises implanting the left ventricular electrode into the anterior interventricular vein of the patient's heart.

Example 9: The method as in Example 6, wherein implanting the left ventricular electrode comprises implanting the left ventricular electrode into the lateral vein of the patient's heart.

Example 10: The method as in any one of Examples 6-9, wherein delivering pacing therapy comprises utilizing field steering to avoid left atrial capture by the left ventricular electrode.

Example 11: A method comprising:

delivering a delivery catheter and a penetration element disposed in the delivery catheter to the right ventricular endocardium of the interventricular septal wall of a patient's heart;

puncturing the right ventricular endocardium using the penetration element to form an opening through the right ventricular endocardium and into the interventricular septal wall;

retracting the penetration element;

advancing a distal portion of a guide element through the delivery catheter and the opening and into the interventricular septal wall to extend along the left ventricular endocardial wall; and delivering a distal portion of an implantable medical lead over the guide element to the left ventricular myocardium to extend along the left ventricular endocardial wall to position at least one left ventricular electrode on the distal portion in the left ventricular myocardium.

Example 12: The method as in Example 11, wherein the at least one left ventricular electrode is positioned proximate to the left bundle branch of the conduction system of the patient's heart.

Example 13: The method as in any one of Examples 11-12, further comprising implanting at least one right ventricular electrode proximate to the right ventricular endocardium, the at least one right ventricular electrode being positioned proximal to the at least one left ventricular electrode on the distal portion of the implantable medical lead.

Example 14: The method as in Example 13, further comprising:

monitoring electrical activity of at least one of the at least one right ventricular electrode and the at least one left ventricular electrode; and delivering pacing therapy using at least one of the at least one right ventricular electrode and the at least one left ventricular electrode.

Example 15: The method as in Example 14, wherein delivering pacing therapy comprises delivering pacing pulses using the at least one left ventricular electrode to the left bundle branch of the conduction system of the patient's heart.

Example 16: The method as in any one of Examples 13-15, wherein the at least one left ventricular electrode comprises a plurality of left ventricular electrodes, wherein the at least one right ventricular electrode comprises a plurality of right ventricular electrodes.

Example 17: The method as in any one of Examples 11-16, wherein the delivery catheter extends from a proximal portion to a distal portion, wherein the distal portion defines a curvature to position a distal end of the catheter substantially flush to the right ventricular endocardium.

Example 18: The method as in any one of Examples 11-17, wherein the guide element extends from a proximal region to the distal region, wherein the distal region comprises a distal curvature portion that curves when exiting the delivery catheter into the interventricular septal wall so as to deliver at least a region of the distal portion of the implantable medical lead substantially parallel to the interventricular septal wall in the left ventricular myocardium.

Example 19: A system for delivering an implantable medical lead into the interventricular septal wall and proximate the left ventricular myocardium, the system comprising:

a delivery catheter extending from a proximal end region to a distal end region, the distal end region positionable adjacent to the right ventricular endocardium of the interventricular septal wall of a patient's heart;

a penetration element disposable in the delivery catheter to form an opening through the right ventricular endocardium and into the interventricular septal wall; and a guide element extending from a proximal end region to a distal end region, the guide element disposable in the delivery catheter to enter the interventricular septal wall through the opening and to extend along the left ventricular endocardial wall.

Example 20: The system as in Example 19, wherein the system further comprises an implantable medical lead comprising at least one left ventricular electrode and deliverable over the guide element to the left ventricular myocardium to extend along the left ventricular endocardial wall to position the at least one left ventricular electrode in the left ventricular myocardium of the patient's heart.

Example 21: The system as in Example 20, wherein the at least on left ventricular electrode is positioned proximate to the left bundle branch of the conduction system of the patient's heart.

Example 22: The system as in any one of Examples 20-21, where the implantable medical lead further comprises at least one right ventricular electrode positionable proximate to the right ventricular endocardium.

Example 23: The system as in Example 22, wherein the at least one left ventricular electrode comprises a plurality of left ventricular electrodes, wherein the at least one right ventricular electrode comprises a plurality of right ventricular electrodes.

Example 24: The system as in any one of Examples 19-23, wherein the distal end region of the delivery catheter defines a curvature to position a distal end of the catheter substantially flush to the right ventricular endocardium.

Example 25: The system as in any one of Examples 19-24, wherein the distal end region of the guide element comprises a distal curvature portion that curves when exiting the delivery catheter into the interventricular septal wall so as to deliver at least a region of the distal portion of the implantable medical lead substantially parallel to the interventricular septal wall in the left ventricular myocardium.

Thus, various embodiments of implantable medical devices for multi-chamber pacing are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method comprising:

delivering a delivery catheter extending from a proximal portion to a distal portion and a penetration element disposed in the delivery catheter to the right ventricular endocardium of the interventricular septal wall of a patient's heart, wherein the distal portion of the delivery catheter terminates in a distal end, wherein the distal end is a distal-most surface of the delivery catheter, wherein the distal portion defines a curvature to position the distal end of the delivery catheter substantially flush to the right ventricular endocardium;

puncturing the right ventricular endocardium using the penetration element to form an opening through the right ventricular endocardium and into the interventricular septal wall;

retracting the penetration element;

advancing a distal portion of a guide element through the delivery catheter and the opening and into the interventricular septal wall to extend along the left ventricular endocardial wall; and delivering a distal portion of an implantable medical lead over the guide element to the left ventricular myocardium to extend along the left ventricular endocardial wall to position at least one left ventricular electrode on the distal portion in the left ventricular myocardium.

2. The method of claim 1, wherein the at least one left ventricular electrode is positioned proximate to the left bundle branch of the conduction system of the patient's heart.

3. The method of claim 1, further comprising implanting at least one right ventricular electrode proximate to the right ventricular endocardium, the at least one right ventricular electrode being positioned proximal to the at least one left ventricular electrode on the distal portion of the implantable medical lead.

4. The method of claim 3, further comprising:

monitoring electrical activity of at least one of the at least one right ventricular electrode and the at least one left ventricular electrode; and delivering pacing therapy using at least one of the at least one right ventricular electrode and the at least one left ventricular electrode.

5. The method of claim 4, wherein delivering pacing therapy comprises delivering pacing pulses using the at least one left ventricular electrode to the left bundle branch of the conduction system of the patient's heart.

6. The method of claim 3, wherein the at least one left ventricular electrode comprises a plurality of left ventricular electrodes, wherein the at least one right ventricular electrode comprises a plurality of right ventricular electrodes.

7. The method of claim 1, wherein the guide element extends from a proximal region to the distal region, wherein the distal region comprises a distal curvature portion that curves when exiting the delivery catheter into the interventricular septal wall so as to deliver at least a region of the distal portion of the implantable medical lead substantially parallel to the interventricular septal wall in the left ventricular myocardium.

* * * * *